(12) United States Patent
Pettit et al.

(10) Patent No.: US 9,914,755 B2
(45) Date of Patent: Mar. 13, 2018

(54) CYCLOSPORIN DERIVATIVES WHEREIN THE MEBMT SIDECHAIN HAS BEEN CYCLIZED

(71) Applicant: Allergan, Inc., Irvine, CA (US)

(72) Inventors: Simon N. Pettit, Colchester (GB); Andrew D. Jones, Saffron Walden (GB); Catherine Simone V. Frydrych, Sawbridgeworth (GB); Alex J. Thomas, London (GB); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/991,009

(22) Filed: Jan. 8, 2016

(65) Prior Publication Data
US 2016/0200767 A1 Jul. 14, 2016

Related U.S. Application Data

(60) Provisional application No. 62/101,061, filed on Jan. 8, 2015, provisional application No. 62/101,079, filed on Jan. 8, 2015.

(51) Int. Cl.
*A61K 38/00* (2006.01)
*A61P 39/06* (2006.01)
*C07K 7/64* (2006.01)

(52) U.S. Cl.
CPC .............. *C07K 7/645* (2013.01); *A61K 38/00* (2013.01)

(58) Field of Classification Search
CPC ........... A61K 38/00; A61K 38/12; C07K 7/64
See application file for complete search history.

(56) References Cited

U.S. PATENT DOCUMENTS

| | | | |
|---|---|---|---|
| 4,288,431 A * | 9/1981 | Traber | C07K 7/645 |
| | | | 435/71.1 |
| 4,798,823 A | 1/1989 | Witzel | |
| 4,839,342 A | 6/1989 | Kaswan | |
| 4,885,276 A | 12/1989 | Witzel | |
| 5,214,130 A | 5/1993 | Patchett et al. | |
| 5,227,467 A | 7/1993 | Durette et al. | |
| 5,474,979 A | 12/1995 | Ding et al. | |
| 6,254,860 B1 | 7/2001 | Garst | |
| 6,350,442 B2 | 2/2002 | Garst | |
| 6,790,935 B1 | 9/2004 | Mutter et al. | |
| 7,297,679 B2 | 11/2007 | Chang | |
| 7,511,013 B2 | 3/2009 | Molino et al. | |
| 7,538,084 B2 | 5/2009 | Molino et al. | |
| 7,696,166 B2 | 4/2010 | Molino et al. | |
| 7,718,767 B2 | 5/2010 | Fliri et al. | |
| 7,968,518 B2 | 6/2011 | Hijikata et al. | |
| 8,524,671 B2 | 9/2013 | Garst et al. | |
| 8,716,238 B2 | 5/2014 | Garst et al. | |
| 9,175,042 B2 | 11/2015 | Garst et al. | |
| 9,266,927 B2 | 2/2016 | Pettit et al. | |
| 2001/0036449 A1 | 11/2001 | Garst | |
| 2003/0165545 A1 | 9/2003 | Huth et al. | |
| 2003/0186855 A1 | 10/2003 | Or et al. | |
| 2003/0212249 A1 | 11/2003 | Naicker et al. | |
| 2004/0110666 A1 | 6/2004 | Or et al. | |
| 2005/0059583 A1 | 3/2005 | Acheampong | |
| 2005/0277584 A1 | 12/2005 | Tien | |
| 2006/0069015 A1 | 3/2006 | Molino et al. | |
| 2006/0105944 A1 | 5/2006 | Stern et al. | |
| 2006/0105945 A1 | 5/2006 | Stern et al. | |
| 2007/0015694 A1 | 1/2007 | Chang et al. | |
| 2007/0027072 A1 | 2/2007 | Tien et al. | |
| 2007/0087962 A1 | 4/2007 | Tien et al. | |
| 2007/0191266 A1 | 8/2007 | Brin | |
| 2007/0207951 A1 | 9/2007 | Schiffman | |
| 2007/0299004 A1 | 12/2007 | Acheampong et al. | |
| 2008/0146497 A1 | 6/2008 | Graham et al. | |
| 2008/0207494 A1 | 8/2008 | Chang et al. | |
| 2009/0312300 A1 | 12/2009 | Li et al. | |
| 2010/0009953 A1 | 1/2010 | Garst | |
| 2010/0167996 A1 | 7/2010 | Fliri et al. | |
| 2010/0209390 A1 | 8/2010 | Or et al. | |
| 2010/0305037 A1 | 12/2010 | Garst et al. | |
| 2011/0008284 A1 | 1/2011 | Gao et al. | |
| 2011/0008285 A1 | 1/2011 | Long et al. | |

(Continued)

FOREIGN PATENT DOCUMENTS

| CA | 2086267 A1 * | 6/1994 | ............. C07K 7/645 |
|---|---|---|---|
| EP | 0194972 A2 | 9/1986 | |

(Continued)

OTHER PUBLICATIONS

"Blepharitis", www.eyesite.org/cornea-and-eye-surface/blepharitis, 2000-2013, downloaded on May 28, 2013, 6 pages.
Aebi, Johannes et al, Synthesis, conformation and immunosuppressive activity of a conformationally restricted cyclosporine lactam analogue, J Med Chem, 1988, 1805-1815, 31.
Anderson et al, The Practice of Medicinal Chemistry, 1996, 32 Pages, 3rd Edition.
Berge, Stephen M., Pharmaceutical Salts, Journal of Pharmaceutical Sciences, Jan. 1977, 1-19, 66 (1), US.
Bingham, Ann et al, Over One Hundred Solvates of Sulfathiazole, Chem. Commun., 2001, 603-604.
Bron, Anthony et al, Methodologies to Diagnose and Monitor Dry Eye Disease:Report of the Diagnostic Methodology Subcommittee of the International Dry Eye WorkShop, Ocul. Surf., 2007, 108-152, 5(2).
Caira, Mino et al, Preparation and Crystal Characterization of a Polymorph, a Monohydrate, and an Ethyl Acetate Solvate of the Antifungal Fluconazole, Journal of Pharmaceutical Sciences, Mar. 2004, 601-611, 93(3).
Chen, Peilin et al, A sensitive enzyme immunoassay for cyclosporin A using antibodies generated against a novel hapten, Research Communications in Molecular Pathology and Pharmacology, 1995, 317-26, 88(3).
Cross, L.C. et al, Rules for the Nomenclature of Organic Chemistry, Section E: Stereochemistry, Pure & Appl. Chem., 1976, 11-30, 45.
Eberle, Marcel et al, Preparation and in Vitro Activities of Ethers of [D-Serine]8-cyclosporin, Journal of Medicinal Chemistry, 1995, 1853-1864, 38.

(Continued)

*Primary Examiner* — Kaipeen Yang
(74) *Attorney, Agent, or Firm* — Barbara C. Potts

(57) ABSTRACT

The present invention relates to cyclosporin analogs that are potent inhibitors of cyclophilin D and have low immunosuppressive activity; processes for preparing them; pharmaceutical compositions containing them; and methods for using these analogs and compositions containing them for the treatment of medical conditions, including but not limited to ischemic conditions, such as ischemia-reperfusion (I/R) injury, including myocardial FR injury, cerebral I/R injury, and ocular or retinal I/R injury.

8 Claims, 1 Drawing Sheet

(56) References Cited

U.S. PATENT DOCUMENTS

| | | |
|---|---|---|
| 2011/0008286 A1 | 1/2011 | Wang et al. |
| 2011/0063295 A1 | 3/2011 | Kuo |
| 2012/0088734 A1 | 4/2012 | Frydrych et al. |
| 2012/0135939 A1 | 5/2012 | Garst et al. |
| 2012/0190661 A1 | 7/2012 | Trogden et al. |
| 2013/0122059 A1 | 5/2013 | Gore et al. |
| 2013/0123193 A1 | 5/2013 | Wu et al. |
| 2013/0123194 A1 | 5/2013 | Blanda et al. |
| 2013/0123195 A1 | 5/2013 | Blanda et al. |
| 2013/0210704 A1 | 8/2013 | Su et al. |
| 2014/0005124 A1 | 1/2014 | Garst et al. |
| 2014/0200185 A1 | 7/2014 | Garst |
| 2015/0065433 A1 | 3/2015 | Frydrych et al. |
| 2016/0022765 A1 | 1/2016 | Garst et al. |

FOREIGN PATENT DOCUMENTS

| | | |
|---|---|---|
| WO | 1992-013545 A1 | 8/1992 |
| WO | 2000-061168 A1 | 10/2000 |
| WO | 2002-083143 A1 | 10/2002 |
| WO | 2003-033010 A1 | 4/2003 |
| WO | 2003-033526 A2 | 4/2003 |
| WO | 2004-082629 A2 | 9/2004 |
| WO | 2006-039668 A2 | 4/2006 |
| WO | 2007-008894 A2 | 1/2007 |
| WO | 2007-047334 A1 | 4/2007 |
| WO | 2007-136759 A2 | 11/2007 |
| WO | 2008-014200 A2 | 1/2008 |
| WO | 2008-137617 A1 | 11/2008 |
| WO | 2008-143996 A1 | 11/2008 |
| WO | 2009-099467 A2 | 8/2009 |
| WO | 2009-148615 A1 | 12/2009 |
| WO | 2010-006117 A2 | 1/2010 |
| WO | 2010-012073 A1 | 2/2010 |
| WO | 2010-076329 A1 | 7/2010 |
| WO | 2010-080913 A1 | 7/2010 |
| WO | 2010-080915 A1 | 7/2010 |
| WO | 2010-088573 A1 | 8/2010 |
| WO | 2010-120838 A1 | 10/2010 |
| WO | 2010-127301 A1 | 11/2010 |
| WO | 2010-138422 A1 | 12/2010 |
| WO | 2010-138423 A1 | 12/2010 |
| WO | 2011-020596 A2 | 2/2011 |
| WO | 2011-150102 A1 | 12/2011 |
| WO | 2012-009715 A2 | 1/2012 |
| WO | 2012-021796 A2 | 2/2012 |
| WO | 2012-051193 A1 | 4/2012 |
| WO | 2012-051194 A1 | 4/2012 |
| WO | 2012-075494 A1 | 6/2012 |
| WO | 2012-079172 A1 | 6/2012 |
| WO | 2012-166610 A1 | 12/2012 |
| WO | 2013-052424 A1 | 4/2013 |
| WO | 2013-181339 A2 | 12/2013 |
| WO | 2014-049540 A2 | 4/2014 |
| WO | 2014-053834 | 4/2014 |
| WO | 2014-145686 A2 | 9/2014 |

OTHER PUBLICATIONS

Eberle, Marcel et al, Synthesis of the Main Metabolite (OL-17) of Cyclosporin A, J. Org. Chem., 1992, 2689-2691, 57.

Elrod, John et al, Physiologic Functions of Cyclophilin D and the Mitochondrial Permeability Transition Pore, Circulation Journal, 2013, 12 Pages.

Enzo Life Sciences, Calcineurin Phosphatase Assay Kit, A complete colorimetric assay kit for measuring calcineurin phosphatase activity, Instruction Manual BML-AK804, Feb. 16, 2012, 8 pages.

Evers, Michel et al, Synthesis of non-immunosuppressive cyclophilin-cyclosporin A derivatives as potential anti-HIV-1 drugs, Bioorganic & Medicinal Chemistry Letters, 2003, 4415-4419, 13.

Fliri, Hans et al, Cyclosporins Structure-Activity Relationships, Anals New York Academy of Sciences, Nov. 30, 1993, 47-53.

Fu, Jiping et al, Potent Nonimmunosuppressive Cyclophilin Inhibitors With Improved Pharmaceutical Properties and Decreased Transporter Inhibition, J Med Chem, 2014, 8503-8516, 57.

Gould, Philip, Salt Selection for Basic Drugs, International Journal of Pharmaceutics, 1986, 201-217, 33.

Greene, Theodora, Protective Groups in organic Synthesis, 1984, 9 Pages (Table of Contents Only).

Greene, Theodora, Protective Groups in Organic Synthesis, 1991, 52 Pages, 3rd Edition.

Handbook of Pharmaceutical Salts, P.Heinrich Stahal& Camille G. Wermuth (Eds), Verlag Helvetica Chemica Acta—Zürich, 2002, 329-345.

Heinrich Stahl, Pharmaceutical Salts, Handbook of Pharmaceutical Salts, 2002, 329-345, International Union of Pure and Applied Chemistry, Verlag Helvetica Chemica Acta—Zürich.

Hubler, Francis et al, Synthetic routes to NetXaa4-cyclosporin A derivatives as potential anti-HIV 2 drugs, Tet. Lett., 2000, 7193-7196, 41.

Kim, Sy et al, Inhibition of Cyclophilin D by Cyclosporin A Promotes Retinal Ganglion Cell Survival by Preventing Mitochondrial Alteration in Ischemic Injury, Cell Death and Disease, 2014, e1105, 5.

Kitahara, Takeshi et al, Synthesis of the Enantiomers of Sclerosporin and Sclerosporal to Determine the Absolute Configuration of the Natural Products, Tetrahedron Letters, 1984, 4685-4688, 41.

Lawen, A. et al, Enzymatic biosynthesis of cyclosporine A and analogues, Biochimie, 1992, 511-516, 74.

Lee, Jinhwa et al, Current Implications of Cyclophilins in Human Cancers, Journal of Experimental & Clinical Cancer Research, 2010, 6 Pages, 29(97).

Lemp, Michael et al, The Definition and Classification of Dry Eye Disease: Report of the Definition and Classification Subcommittee of the International Dry Eye Workshop, Ocular Surface, Apr. 2007, 75-92, 5(2).

Levitsky, Konstantin et al, Exo-Mechanism Proximity-Accelerated Alkylations: Investigations of Linkers, Electrophiles and Surface Mutations in Engineered Cyclophilin-Cyclosporin Systems, ChemBioChem, 2005, 890-899, vol. 6.

Pflegfelder, Stephen C., Antiinflammatory Therapy for Dry Eye, American Journal of Ophthalmology, Feb. 2004, 337-342, 137 (2), US.

Piot, Christophe et al, Effect of Cyclosporine on Reperfusion Injury in Acute Myocardial Infarction, New England Journal of Medicine, Jul. 2008, 473-481, 359.

Quesniaux, Valerie et al, Cyclophilin binds to the region of cyclosporine involved in its immunosuppressive activity, Eur. J. Immunology, 1987, 1359-1365, 17.

Rao, G. Venkateswara et al, Synthesis of 2-(N-disubstituted amino)ethyltriphenylphosphonium bromides, Tetrahedron Letters, 2008, 824-826, 49.

Riss, Bernard et al, Development of a Practical Process for the Opening of Macrocyclic Cyclosporin A and Amino Acid Deletion, Org Process Dev, 2014, 1763-1770, 18.

Seebach, Dieter, Modification of Cyclosporin A (CS): Generation of an Enolate at Thesarcosine Residue and Reactions with Electrophiles, Helvetica Chimica, 1993, 1564-1590, 76 (4).

Sigal, Nolan et al, Is cyclophilin involved in the immunosuppressive and nephrotoxic mechanism of action of cyclosporine A?, Exp. Med., Mar. 1991, 619-628, 173.

Survase, Shrikant et al, Cyclosporin A—A review on fermentative production, downstream processing and pharmacological applications, Biotechnology Advances, 2011, 418-435, 29.

Sweeney, Zachary et al, From Chemical Tools to Clinical Medicines: Nonimmunosuppressive Cyclophilin Inhibitors Derived from the Cyclosporin and Sanglifehrin Scaffolds, J Med Chem, 2014, 7145-7159, 57(17).

Traber, Rene et al, Cyclosporins—New Analogues by Precursor Directed Biosynthesis, The Journal of Antibiotics, Apr. 1989, 591-597.

Van Tonder, Elsa et al, Preparation and Physicochemical Characterization of 5 Niclosamide Solvates and 1 Hemisolvate, AAPS PharmSciTech, 2004, 1-10, 5(1).

(56) References Cited

OTHER PUBLICATIONS

Zucker, K. et al, Augmentation of mycophenolate mofetil in renal transplant patients receiving Prograf and Cellceptin combination therapy, Transplantation Proceedings, 1997, 334-336, 29.

Eberle, M.K. et al, Modifications of the MeBmt Side Chain of Cyclosporin A, Bioorganic & Medicinal Chemistry Letters, Aug. 1995, 1725-1728, 5(15).

He, QL et al, Stimultaneous Identification of Multiple Receptors of Natural Product Using an Optimized cDNA Phage Display Cloning, Bioorganic & Medicinal Chemistry Letters, Jul. 2008, 3995-3998, 18(14).

Patent Cooperation Treaty, Notification of Transmittal of the International Search Report and the Written Opinion of the International Searching Authority, or the Declaration, PCT/US2016/012695, Apr. 6, 2016, pp. 1-12.

Yang, Zhicai et al, Novel Oxidation of Cyclosporin A: Preparation of Cyclosporin Methyl Vinyl Keton (Cs-MVK), Synlett, Oct. 2009, 2935-2938, 2009(18).

* cited by examiner

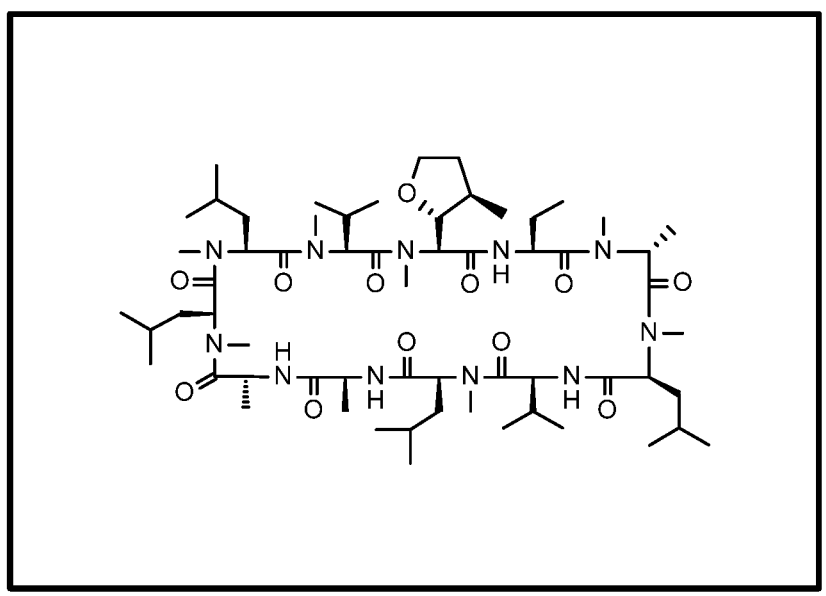

CYCLOSPORIN DERIVATIVES WHEREIN THE MEBMT SIDECHAIN HAS BEEN CYCLIZED

CROSS-REFERENCE TO RELATED APPLICATIONS

This application claims the benefit of U.S. Provisional Application Ser. No. 62/101,061, filed Jan. 8, 2015, and also claims the benefit of U.S. Provisional Application Ser. No. 62/101,079, filed Jan. 8, 2015, each of which is hereby incorporated in its entirety by this specific reference.

FIELD OF THE INVENTION

The present invention relates to novel cyclosporin analogs, processes for preparing them, pharmaceutical compositions containing them, and methods for using these analogs and the compositions containing them for the treatment of medical conditions, including but not limited to ischemic conditions, such as ischemia-reperfusion (I/R) injury, including myocardial I/R injury, cerebral I/R injury, and ocular or retinal FR injury.

BACKGROUND OF THE INVENTION

Cyclophilins are intracellular receptor proteins for cyclosporin A (CsA), a widely recognized immunosuppressive agent. Cyclophilin proteins exhibit peptidyl-prolyl cis-trans isomerase (PPIase) activity, which catalyzes cis-trans isomerization of peptide bonds preceding proline, and play functional roles in chaperoning and protein folding. The immunosuppressive activity for which CsA is so well known does not directly result from inhibiting cyclophilin activity. Rather, a CsA-cyclophilin A complex inhibits the $Ca^{2+}$/calmodulin-dependent phosphatase calcineurin, thereby suppressing T-cell proliferation by interfering with downstream signal transduction. (See J. Lee and S. S. Kim, *Journal of Experimental & Clinical Cancer Research*, 2010, 29:97; J. W. Elrod and J. D. Molkentin, *Circulation Journal*, 2013, 77:1111; C. Piot, et al., *New England Journal of Medicine*, 2008, 359:473.)

CsA binds to most members of the cyclophilin family, including cyclophilin A (CypA) and cyclophilin D (CypD). CypA is found in the cytosol, while CypD is a mitochondrial matrix protein. The role ascribed to CypD in the mitochondrial matrix is to modulate the mitochondrial permeability transition pore (MPTP), a non-specific high-conductance channel in the inner mitochondrial membrane. MPTP opening increases inner mitochondrial cell membrane permeability, allowing an influx of cytosolic molecules into the mitochondrial matrix. This influx increases the matrix volume and disrupts the outer mitochondrial membrane, which may lead to cell death. MPTP regulation by CypD appears to provide a physiologic $Ca^{2+}$ release mechanism for proper control of mitochondrial metabolism. For example, in the case of myocardial infarction, MPTP opening may be triggered by calcium overload and excessive reactive oxygen species (ROS) at the time of reperfusion, resulting in metabolic alterations (e.g., collapse of mitochondrial membrane potential, uncoupling of the respiratory chain, efflux of pro-apoptotic factors, and hydrolysis of ATP), which may lead to cardiomyocyte death. (See J. W. Elrod, et al., supra; C. Piot, et al., *New England Journal of Medicine*, 2008, 359:473; S. Y. Kim, et al., *Cell Death and Disease*, 2014, e1105).

CsA has been reported to limit ischemia-reperfusion injury under experimental conditions. In a small proof-of-concept trial on the effects of CsA on reperfusion injury in acute myocardial infarction, CsA reduced infarct size when administered at the time of reperfusion. These findings led to the hypothesis that CsA-induced inhibition of MPTP opening occurs by preventing the calcium-induced interaction of CypD with an MPTP component. (See C. Piot, et al., supra).

CsA has also been reported to interact with CypD to inhibit MPTP opening and ameliorate neuronal cell death against ischemic injury in the central nervous system, and has been studied in the context of ischemic retinal injury, specifically, ischemic injury in response to elevated intraocular pressure (TOP) (See S. Kim, et al., *Cell Death and Disease*, 2014, e1105.) IOP presents risks for retinal ganglion cell (RGC) death and optic nerve degeneration in retinal ischemia and glaucoma. Investigations into the mechanism for ischemic retinal injury induced by acute increases in IOP have revealed that acute IOP elevation significantly upregulates CypD protein expression in ischemic retina, which may, in turn, facilitate MPTP opening, increase mitochondrial vulnerability and trigger cell death in the ischemic retina. CsA was found to prevent CypD upregulation and to promote RGC survival against ischemic injury by preventing mitochondrial alteration. CsA-mediated CypD inhibition may thus have promising therapeutic potential for protecting RGCs against ischemic injury mediated mitochondrial dysfunction. (Id.)

CsA (CAS Registry Number: 59865-13-3) is a naturally occurring fungal metabolite and the first identified member of the cyclosporin family of poly-N-methylated cyclic undecapeptides having the following structure:

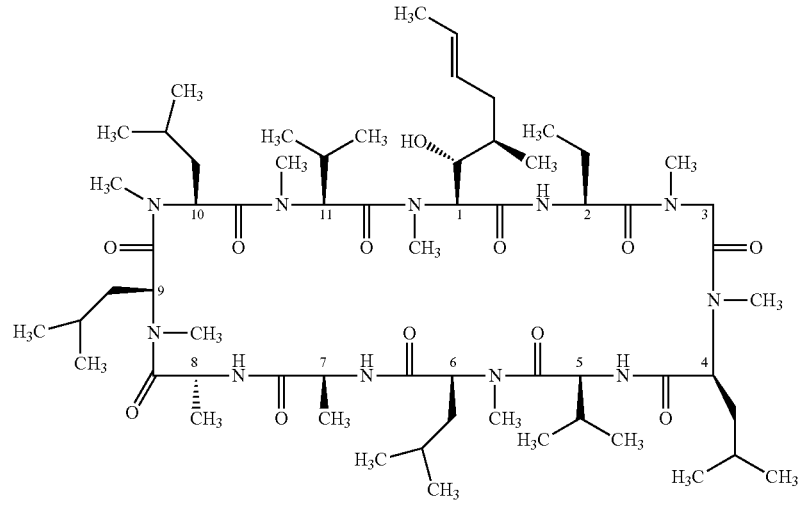

Cyclosporin A

CsA consists of 11 amino acids and can be further represented as follows:

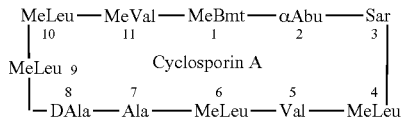

wherein:

MeBmt is (4R)-4-[(E)-2-butenyl]-4-methyl-L-threonine;

αAbu is L-α-aminobutyric acid;

Sar is sarcosine;

MeLeu is N-methyl-L-leucine;

Val is L-valine;

Ala is L-alanine;

DAla is D-alanine; and

MeVal is N-methyl-L-valine.

The numbers 1-11 are used to designate each of the eleven amino acids. Thus, MeBMT is the amino acid at position 1, while sarcosine is the amino acid at position 3. In certain instances, the description herein may refer to the amino acid side chain at any one of positions 1-11. The carbon to which the amino acid side chain is attached is referred to as the alpha (α) carbon.

Cyclosporin B is identical to CsA, except that αAbu is replaced by L-alanine.

Cyclosporin C is identical is identical to CsA, except that αAbu is replaced by L-threonine.

Cyclosporin D is identical to CsA, except that αAbu is replaced by L-valine.

CsA, which binds to most members of the cyclophilin family, is not specific for mitochondrial CypD. (J. W. Elrod et al., supra; C. Piot et al., supra).

There remains a need for CypD-selective inhibitors.

The present invention relates to the surprising discovery of non-immunosuppressive analogs of CsA that are potent inhibitors of CypD.

SUMMARY OF THE INVENTION

Accordingly, the present invention describes compounds having Formula I:

Formula I

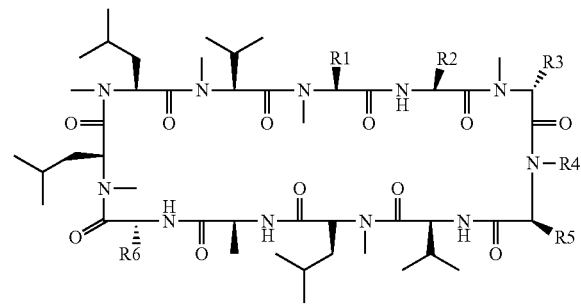

wherein:

$R^1$ is

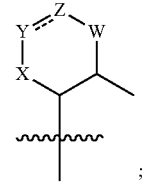

;

$R^2$ is —$CH_3$, —$CH_2CH_3$, —$CH(CH_3)(OH)$, —$CH(CH_3)_2$ or —$CH_2CH_2CH_3$;

$R^3$ is —H, —$C_{1-6}$alkyl, —$OC_{1-6}$alkyl, —$C_{1-6}$haloalkyl, —$SC_{1-6}$ alkyl, —$CH_2OH$, —$CH_2OCH_3$,

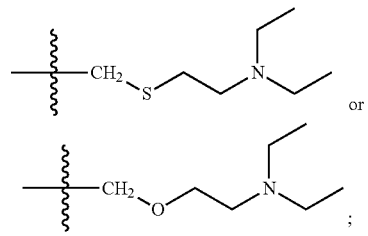

;

$R^4$ is —$CH_3$, —$CH_2CH_3$ or —$CH_2CH_2CH_3$;

$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^7)(CH_2CH_3)$;

$R^6$ is —$CH_3$ or —$CH_2OH$;

$R^7$ is —$OC_{1-6}$alkyl;

$R^8$ is —H or —$C_{1-6}$alkyl;

$R^9$ is —H, —$C_{1-6}$alkyl or —OH;

$R^{10}$ is —H, —$C_{1-6}$alkyl or —OH;

$R^{11}$ is —H or —$C_{1-6}$alkyl;

$R^{12}$ is —H or —$C_{1-6}$alkyl;

$R^{13}$ is —H or —$C_{1-6}$alkyl;

X is O or $NR^8$;

Y is $CR^9R^{10}$; $CR^{11}$ or C=O;

Z is $(CH_2)_m$, $CR^{12}$, $NR^{13}$ or O;

W is $(CH_2)_n$;

m is 1, 2 or 3;

n is 0 or 1; and the dashed line indicates that the bond joining Y and Z is a single or double bond; provided that:

(a) when the bond joining Y and Z is a single bond, then Y is $CR^9R^{10}$ or C=O, and Z is $(CH_2)_m$, $NR^{13}$ or O; and (b) when the bond joining Y and Z is a double bond, then Y is $CR^{11}$ and Z is $CR^{12}$;

or a pharmaceutically acceptable salt thereof.

In other aspects, the invention provides for pharmaceutical compositions comprising a compound of Formula I.

In other aspects, the invention provides for pharmaceutical compositions comprising a compound of Formula I for use in treating an ischemic condition in a subject.

In other aspects, the invention provides for pharmaceutical compositions comprising a compound of Formula I for use in treating an ischemic condition in a subject, such as an I/R injury, including but not limited to myocardial I/R injury, cerebral I/R injury, ocular or retinal I/R injury.

In other aspects, the invention provides for a method of treating an ischemic condition in a subject, the method comprising administering a therapeutically effective amount of a compound of Formula I to the subject, thereby treating the ischemic condition.

In other aspects, the invention provides for a method of treating an ischemic condition in a subject, the method comprising administering a therapeutically effective amount of a compound of Formula I to the subject, thereby treating the ischemic condition; wherein the ischemic condition is an I/R injury.

In other aspects, the invention provides for a method of treating an ischemic condition in a subject, the method comprising administering a therapeutically effective amount of a compound of Formula I to the subject, thereby treating the ischemic condition; wherein the ischemic condition is an I/R injury, such as myocardial I/R injury, cerebral I/R injury, ocular or retinal I/R injury.

These and other aspects and advantages of the present invention may be more readily understood and appreciated with reference to the following drawings and detailed description.

BRIEF DESCRIPTION OF THE DRAWINGS

FIG. 1 shows the structure of a particular compound of the invention, which is Compound 3.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used above, and throughout this disclosure, the following terms, unless otherwise indicated, shall be understood to have the following meanings:

"Patient" or "subject" includes both humans and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, heterocyclyl, heteroaryl, cycloalkyl, cyano, hydroxy, alkoxy, alkylthio, amino, oxime (e.g., =N—OH), —NH (alkyl), —NH(cycloalkyl), —N(alkyl)$_2$, —O—C(O)-alkyl, —O—C(O)-aryl, —O—C(O)— cycloalkyl, —SF$_5$, carboxy, —C(O)O-alkyl, —C(O)NH(alkyl) and —C(O)N (alkyl)$_2$. Non-limiting examples of suitable alkyl groups include methyl, ethyl, n-propyl, isopropyl, n-butyl and t-butyl.

The term "substituted" means that one or more hydrogens on the designated atom is replaced with a selection from the indicated group, provided that the designated atom's normal valency under the existing circumstances is not exceeded, and that the substitution results in a stable, compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with one or more of the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

As used herein, "ischemia" refers to reduced blood flow to a cell, tissue and/or organ of a subject.

As used herein, "myocardial ischemia" refers to reduced blood flow to the heart, including its cells and/or tissues.

As used herein, "cerebral ischemia" refers to reduced blood flow to the brain, including its cells and/or tissues. Cerebral ischemia is also known as "brain anoxia."

As used herein, "ocular ischemia" refers to reduced blood flow to the eye.

As used herein, "retinal ischemia" refers to reduced blood flow to the retina of the eye.

As used herein, "ischemia-reperfusion injury" or "I/R injury" refers to cell or tissue damage caused when blood supply returns to the cells or tissue after a period of ischemia.

There are many causes of ischemia, including obstruction or constriction of the arteries, rapid irregular heartbeat, and more.

There are many causes of ocular or retinal ischemia, including vein and artery occlusions, elevated intraocular pressure (IOP), macular degeneration, diabetes and more.

The present invention further includes the compound of Formula I in all its isolated forms. Thus, for example, the compound of Formula I is intended to encompass all forms of the compound such as, for example, any salts, solvates, hydrates, stereoisomers, tautomers, etc.

The present invention further includes the compound of Formula I in its purified form.

It should also be noted that any carbon as well as heteroatom with unsatisfied valences in the text, schemes, examples and Tables herein is assumed to have the sufficient number of hydrogen atom(s) to satisfy the valences, and that any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in organic Synthesis (1991), Wiley, New York.

As used herein, the term "composition" is intended to encompass a product comprising the specified ingredients in the specified amounts, as well as any product which results, directly or indirectly, from combination of the specified ingredients in the specified amounts.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS PharmSciTech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

"Effective amount" or "therapeutically effective amount" is meant to describe an amount of compound or a composition of the present invention effective in producing the desired therapeutic, ameliorative, inhibitory or preventative effect.

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates; oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33, 201-217; Anderson et al. The Practice of Medicinal Chemistry (1996), Academic Press, New York; and in The Orange Book (Food & Drug Administration; Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

It is also possible that the compound of Formula I may exist in different tautomeric forms, and all such forms are embraced within the scope of the invention. Also, for example, all keto-enol, amide or imino ether, and imine-enamine forms of the compounds are included in the invention.

The compounds of Formula I may contain asymmetric or chiral centers, and, therefore, exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral chromatography, for example, using a chiral high pressure liquid chromatograph (HPLC) column.

In particular, a skilled person will realize that even if the absolute stereochemistry of a particular stereoisomer (e.g. an enantiomer or diastereomer) of a molecule is not known, that particular stereoisomer can be distinguished from the other stereoisomers by use of other techniques (e.g. polarimetry, nuclear magnetic resonance spectroscopy, chromatography, and others identifiable to a skilled person). In particular, one exemplary method of distinguishing stereoisomers when the absolute stereochemistry of each stereoisomer is not known is chromatography, such as flash chromatography, medium pressure chromatography or HPLC. In particular, two or more stereoisomers such as diastereomers can be separated and characterized by their retention times, which would be expected to be replicable by using the same chromatographic conditions (e.g. flow rate, column material, solvent systems/gradient profiles, and/or others identifiable to a skilled person). In particular, a skilled person will realize that even when the exact relative retention times of one or more stereoisomers is not replicated (e.g. due to slight variations in the chromatographic parameters and/or chromatographic equipment), a stereoisomer with a shorter retention time can be said to be "faster eluting,", "earlier eluting" or having a "high Rf," and a stereoisomer with a longer retention time can be said to be "slower eluting," "later eluting or having a "low Rf." A skilled person will realize that once two or more stereoisomers are distinguished by a technique such as chromatography, the absolute stereochemistry of the stereoisomers can be determined by techniques or combinations of techniques identifiable to a skilled person (e.g. X-ray crystallography, vibrational circular dichroism, nuclear magnetic resonance, total synthesis, and others identifiable to a skilled person).

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", and the like, is intended to equally apply to the salt and solvate of enantiomers, stereoisomers, rotamers, tautomers, positional isomers, or racemates of the inventive compounds.

The present invention includes pharmaceutical compositions comprising, consisting of, or consisting essentially of a compound having Formula I, or a pharmaceutically acceptable salt thereof, in combination with one or more pharmaceutically acceptable excipients. A pharmaceutically acceptable excipient may improve the stability or effectiveness of the composition. A "pharmaceutically acceptable excipient" is one that is compatible with the compound of Formula I and that is not harmful to the person receiving the pharmaceutical composition. Mixtures of two or more of such suitable excipients may be used. A pharmaceutical composition may comprise two or more compounds having Formula I, or two or more salts thereof.

Pharmaceutical compositions of the present invention can be sterilized and therefore prepared in sterile form for pharmaceutical use.

The pharmaceutical composition may be prepared in a unit dosage form suitable for oral, parenteral, topical or intraocular administration to a patient. Pharmaceutical compositions may be prepared by combining a therapeutically effective amount of a compound of Formula I, or a pharmaceutically acceptable salt thereof, as an active ingredient, with one or more pharmaceutically acceptable excipients. For ocular applications, the excipient is further preferably ophthalmically acceptable, that is, is causes little or no injury to the eye.

Pharmaceutically acceptable excipients for use with the invention include but are not limited to preservatives, buffering agents, antioxidants, lipophilic vehicles, hydrophilic vehicles, tonicity agents, electrolytes, thickeners, neutralizing agents, emulsifiers, dispersing agents, demulcents, plasticizers, occlusive agents, and film formers, and combinations thereof. Certain compositions may include both a buffer component and a tonicity component.

The actual dose of the active compounds of the present invention depends on the specific compound, and on the condition to be treated. The actual amount of compound to be administered in any given case will be determined by a physician taking into account the relevant circumstances, such as the severity of the condition, the age and weight of the patient, the patient's general physical condition, the cause of the condition, and the route of administration.

Each and every feature described herein, and each and every combination of two or more of such features, is included within the scope of the present invention provided that the features included in such a combination are not mutually inconsistent.

The following are non-limiting embodiments of the invention.

In embodiment (1), the invention provides a compound of Formula I:

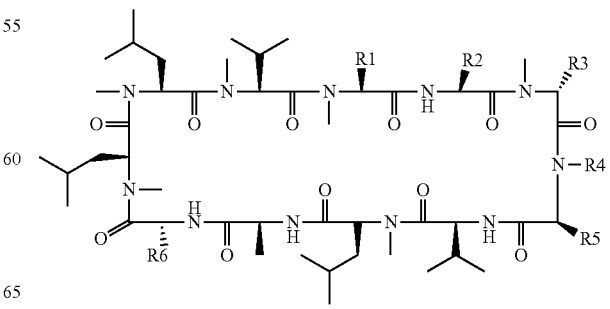

Formula I wherein:
R¹ is

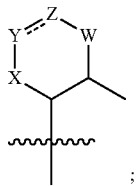
;

R² is —CH₃, —CH₂CH₃, —CH(CH₃)(OH), —CH(CH₃)₂ or —CH₂CH₂CH₃;

R³ is —H, —C$_{1-6}$alkyl, —OC$_{1-6}$alkyl, —C$_{1-6}$haloalkyl, —SC$_{1-6}$ alkyl, —CH₂OH, —CH₂OCH₃,

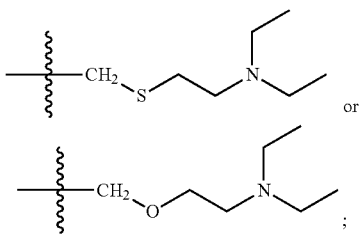
;

R⁴ is —CH₃, —CH₂CH₃ or —CH₂CH₂CH₃;
R⁵ is —CH(CH₃)₂, —CH₂CH(CH₃)₂, —CH₂C(CH₃)₂(OH), —CH(CH₃)(CH₂CH₃) or —CH₂CH(R⁷)(CH₂CH₃);
R⁶ is —CH₃ or —CH₂OH;
R⁷ is —OC$_{1-6}$alkyl;
R⁸ is —H or —C$_{1-6}$alkyl;
R⁹ is —H, —C$_{1-6}$alkyl or —OH;
R¹⁰ is —H, —C$_{1-6}$alkyl or —OH;
R¹¹ is —H or —C$_{1-6}$alkyl;
R¹² is —H or —C$_{1-6}$alkyl;
R¹³ is —H or —C$_{1-6}$alkyl;
X is O or NR⁸;
Y is CR⁹R¹⁰, CR¹¹ or C=O;
Z is (CH₂)$_m$, CR¹², NR¹³ or O;
W is (CH₂)$_n$;
m is 1, 2 or 3;
n is 0 or 1; and
the dashed line indicates that the bond joining Y and Z is a single or double bond;
provided that:
(a) when the bond joining Y and Z is a single bond, then Y is CR⁹R¹⁰ or C=O, and Z is (CH₂)$_m$, NR¹³ or O; and
(b) when the bond joining Y and Z is a double bond, then Y is CR¹¹ and Z is CR¹²;
or a pharmaceutically acceptable salt thereof.

In embodiment (2), the invention provides for a compound of embodiment (1), wherein X is O; Y is CR⁹R¹⁰ or CR¹¹; and Z is (CH₂)$_m$ or CR¹²; or a pharmaceutically acceptable salt thereof.

In embodiment (3), the invention provides for a compound of embodiment (1) or (2), wherein X is O; Y is CR⁹R¹⁰; Z is (CH₂)$_m$; and the bond joining Y and Z is a single bond; or a pharmaceutically acceptable salt thereof.

In embodiment (4), the invention provides for a compound of any one of embodiments (1) through (3), wherein X is O; Y is CR⁹R¹⁰; Z is (CH₂)$_m$; R¹⁰ is H; and the bond joining Y and Z is a single bond; or a pharmaceutically acceptable salt thereof.

In embodiment (5), the invention provides for a compound of any one of embodiments (1) through (4), wherein X is O; Y is CR⁹R¹⁰; Z is (CH₂)$_m$; each of R⁹ and R¹⁰ is H; and the bond joining Y and Z is a single bond; or a pharmaceutically acceptable salt thereof.

In embodiment (6), the invention provides for a compound of any one of embodiments (1) through (5), wherein X is O; Y is CR⁹R¹⁰; Z is (CH₂)$_m$; each of R⁹ and R¹⁰ is H; m is 1; n is 0; and the bond joining Y and Z is a single bond; or a pharmaceutically acceptable salt thereof.

In embodiment (7), the invention provides for a compound of embodiment (1) or (2), wherein X is O; Y is CR⁹R¹⁰ or CR¹¹; Z is (CH₂)$_m$ or CR¹²; R¹⁰ is H; R¹¹ is H; and R¹² is H; or a pharmaceutically acceptable salt thereof.

In embodiment (8), the invention provides for a compound of any one of embodiments (1), (2) or (7), wherein X is O; Y is CR⁹R¹⁰ or CR¹¹; Z is (CH₂)$_m$ or CR¹²; R¹⁰ is H; R¹¹ is H; R¹² is H; m is 1; n is 0; or a pharmaceutically acceptable salt thereof.

In embodiment (9), the invention provides for compounds of any one of embodiments (1) through (4), wherein X is O; Y is CR⁹R¹⁰; Z is (CH₂)$_m$; R¹⁰ is H; m is 1; n is 0; and the bond joining Y and Z is a single bond; or a pharmaceutically acceptable salt thereof.

In embodiment (10), the invention provides for a compound of any one of embodiments (1) through (5), wherein X is O; Y is CR⁹R¹⁰; Z is (CH₂)$_m$; each of R⁹ and R¹⁰ is H; m is 2 or 3; n is 0; and the bond joining Y and Z is a single bond; or a pharmaceutically acceptable salt thereof.

In embodiment (11), the invention provides for a compound of embodiment (1), wherein X is NR⁸; Y is CR⁹R¹⁰; Z is (CH₂)$_m$; and the bond joining Y and Z is a single bond; or a pharmaceutically acceptable salt thereof.

In embodiment (12), the invention provides for a compound of embodiment (1) or (11), wherein X is NR⁸; Y is CR⁹R¹⁰; Z is (CH₂)$_m$; each of R⁹ and R¹⁰ is H; and the bond joining Y and Z is a single bond; or a pharmaceutically acceptable salt thereof.

In embodiment (13), the invention provides for a compound of any one of embodiments (1), (11) or (12), wherein X is NR⁸; Y is CR⁹R¹⁰; Z is (CH₂)$_m$; each of R⁹ and R¹⁰ is H; m is 1; n is 0; and the bond joining Y and Z is a single bond; or a pharmaceutically acceptable salt thereof.

In embodiment (14), the invention provides for a compound of embodiment (1), wherein X is O; Y is C=O or CR⁹R¹⁰; Z is NR¹³; and the bond joining Y and Z is a single bond; or a pharmaceutically acceptable salt thereof.

In embodiment (15), the invention provides for a compound of embodiment (1) or (14), wherein X is O; Y is C=O or CR⁹R¹⁰; Z is NR¹³; each of R⁹ and R¹⁰ is H; R¹³ is —C$_{1-6}$alkyl; and the bond joining Y and Z is a single bond.

In embodiment (16), the invention provides for a compound of any one of embodiments (1), (14) or (15), wherein X is O; Y is C=O or CR⁹R¹⁰; Z is NR¹³; each of R⁹ and R¹⁰ is H; R¹³ is —C$_{1-6}$alkyl; n is 1; and the bond joining Y and Z is a single bond; or a pharmaceutically acceptable salt thereof.

In embodiment (17), the invention provides for a compound of any one of embodiments (1) through (16), wherein R⁴ is —CH₃; R⁵ is —CH₂CH(CH₃)₂; and R⁶ is —CH₃; or a pharmaceutically acceptable salt thereof.

In embodiment (18), the invention provides for a compound of any one of embodiments (1) through (17), wherein $R^3$ is H, —$C_{1-6}$alkyl or —$C_{1-6}$haloalkyl; or a pharmaceutically acceptable salt thereof.

In embodiment (19), the invention provides for a compound of any one of embodiments (1) through (18), wherein $R^3$ is H, —$C_{1-3}$alkyl or —$C_{1-3}$haloalkyl; or a pharmaceutically acceptable salt thereof.

In embodiment (20), the invention provides for a compound of any one of embodiments (1) through (19), wherein $R^1$ is:

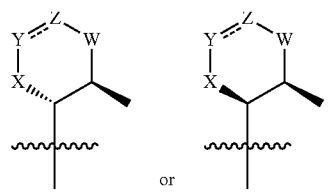

In embodiment (21), the invention provides for a compound of embodiment (1), wherein $R^1$ is selected from the group consisting of:

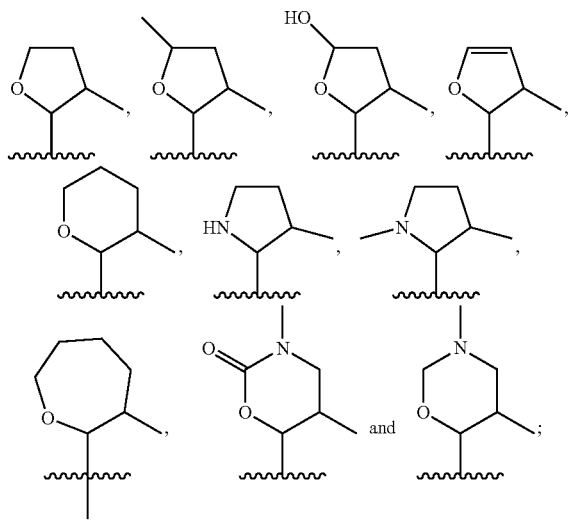

or a pharmaceutically acceptable salt thereof.

In embodiment (22), the invention provides for a compound of embodiment (1), wherein $R^1$ is selected from the group consisting of:

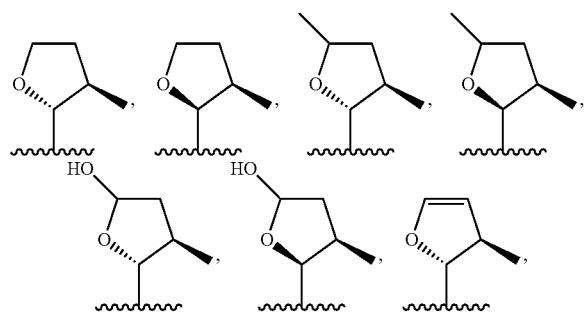

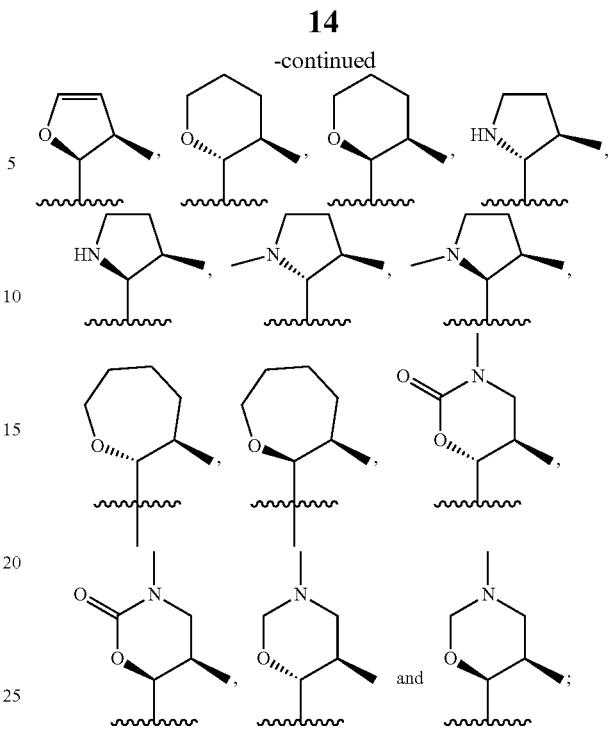

or a pharmaceutically acceptable salt thereof.

In embodiment (23), the invention provides for a compound of any one of embodiment (1), wherein $R^1$ is selected from the group consisting of:

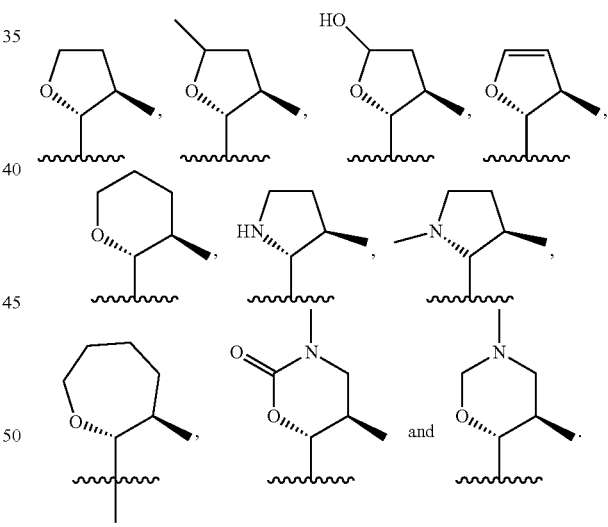

In embodiment (24), the invention provides for a compound of any one of embodiments (1) through (23), wherein each $C_{1-6}$alkyl is independently selected from methyl, ethyl, n-propyl, isopropyl, n-butyl, isobutyl, sec-butyl, tert-butyl, n-pentyl, isopentyl, sec-pentyl, tert-pentyl, neopentyl, 3-pentyl, n-hexyl, 2-methylpentan-1-yl, 2-methylpentan-2-yl, 2-methylpentan-3-yl, 2-methylpentan-4-yl, 2-methylpentan-5-yl, 3-methylpentan-1-yl, 3-methylpentan-2-yl, 3-methylpentan-3-yl, 2,3-dimethylbutan-1-yl, 2,3-dimethylbutan-2-yl, 2,2-dimethylbutan-1-yl, 2,2-dimethylbutan-3-yl and 2,2-dimethylbutan-4-yl; or a pharmaceutically acceptable salt thereof.

In embodiment (25), the invention provides for a compound of any one of embodiments (1) through (23), wherein each $C_{1-6}$alkyl is independently optionally replaced with $C_{1-3}$alkyl; or a pharmaceutically acceptable salt thereof.

In embodiment (26), the invention provides for a compound of embodiment (25), wherein each $C_{1-3}$alkyl is independently selected from methyl, ethyl, n-propyl and isopropyl; or a pharmaceutically acceptable salt thereof.

In embodiment (27), the invention provides for a compound of embodiment (1), wherein the bond joining Y and Z is a single bond.

In embodiment (28), the invention provides for a compound of embodiment (1), wherein the bond joining Y and Z is a single bond, Y is $CR^9R^{10}$ and Z is $(CH_2)_m$.

In embodiment (29), the invention provides for a compound of embodiment (1), wherein the bond joining Y and Z is a single bond, Y is C=O and Z is $(CH_2)_m$.

In embodiment (30), the invention provides for a compound of embodiment (1), wherein the bond joining Y and Z is a single bond, Y is $CR^9R^{10}$ and Z is $NR^{13}$.

In embodiment (31), the invention provides for a compound of embodiment (1), wherein the bond joining Y and Z is a single bond, Y is C=O and Z is $NR^{13}$.

In embodiment (32), the invention provides for a compound of embodiment (1), wherein the bond joining Y and Z is a double bond.

In embodiment (33), the invention provides for a compound of any one of embodiments 1-5, 7, 11-12 and 27-29, wherein m is 1 or 2.

In embodiment (34), the invention provides for a compound of any one of embodiments 1-9, 11-13 and 27-29, wherein m is 1.

In embodiment (35), the invention provides for a compound of any one of embodiments 1-13 and 27-29, wherein n is 0.

In embodiment (36), the invention provides for a compound of any one of embodiments 1-9, 11-13 and 27-29, wherein m is 1 and n is O.

In embodiment (37), the invention provides for a compound of embodiment (1), wherein Z is $(CH_2)_m$, $CR^{12}$ or $NR^{13}$.

In embodiment (38), the invention provides for a compound of any preceding embodiment, wherein $R^2$ is —$CH_3$, —$CH_2CH_3$, —$CH(CH_3)(OH)$ or —$CH(CH_3)_2$.

In embodiment (39), the invention provides for a compound of any preceding embodiment, wherein $R^3$ is H, methyl, ethyl, n-propyl, isopropyl, —$CH_2F$, —$CHF_2$ or —$CF_3$; or a pharmaceutically acceptable salt thereof.

In embodiment (40), the invention provides for a compound of any preceding embodiment, wherein $R^3$ is H, methyl, ethyl, n-propyl, or —$CHF_2$; or a pharmaceutically acceptable salt thereof.

In embodiment (41), the invention provides for a compound of any preceding embodiment, wherein $R^8$ is H or methyl; or a pharmaceutically acceptable salt thereof.

In embodiment (42), the invention provides for a compound of any preceding embodiment, wherein $R^9$ is H, methyl or OH, and each of $R^{10}$, $R^{11}$ and $R^{12}$ is H, unless expressly defined otherwise; or a pharmaceutically acceptable salt thereof.

In embodiment (43), the invention provides for a compound of any preceding embodiment, wherein $R^{13}$ is H or methyl, unless expressly defined otherwise; or a pharmaceutically acceptable salt thereof.

In embodiment (44), the invention provides for a compound of any preceding embodiment, wherein $R^4$ is —$CH_3$; $R^5$ is —$CH_2CH(CH_3)_2$; and $R^6$ is —$CH_3$; or a pharmaceutically acceptable salt thereof.

In embodiment (45), the invention provides for a compound selected from the group consisting of:

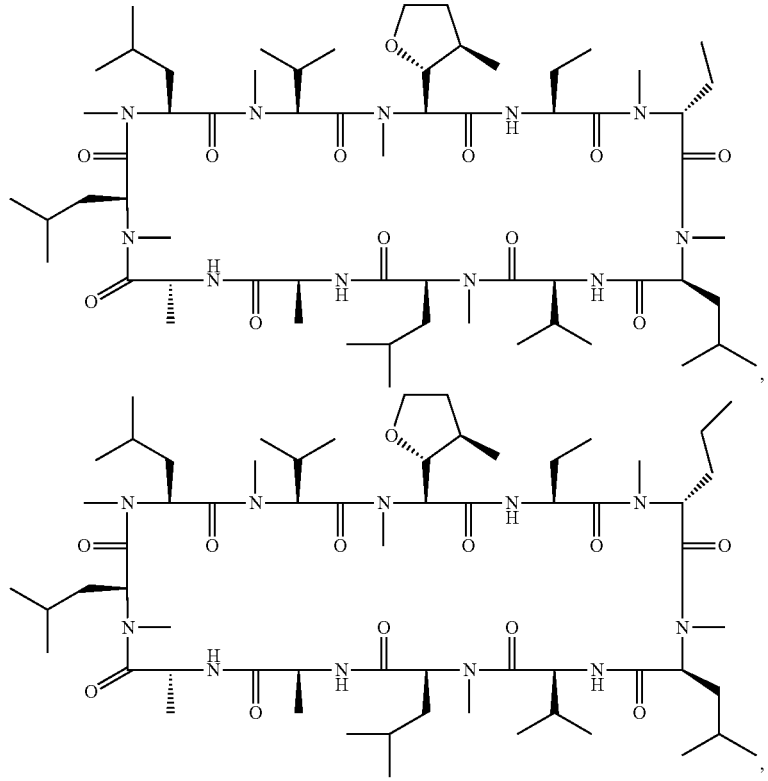

-continued
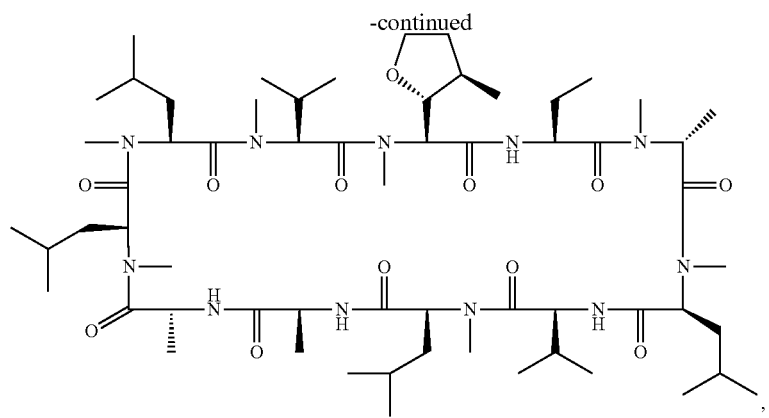,
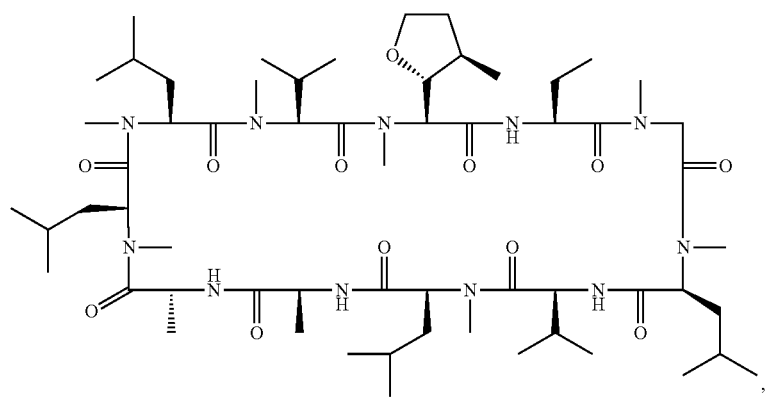,
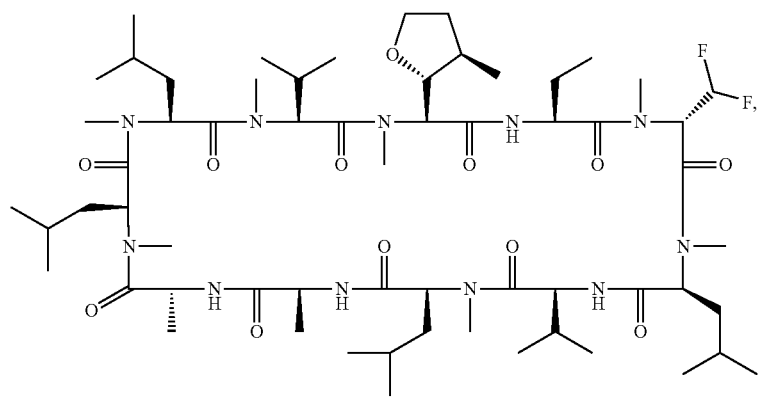,
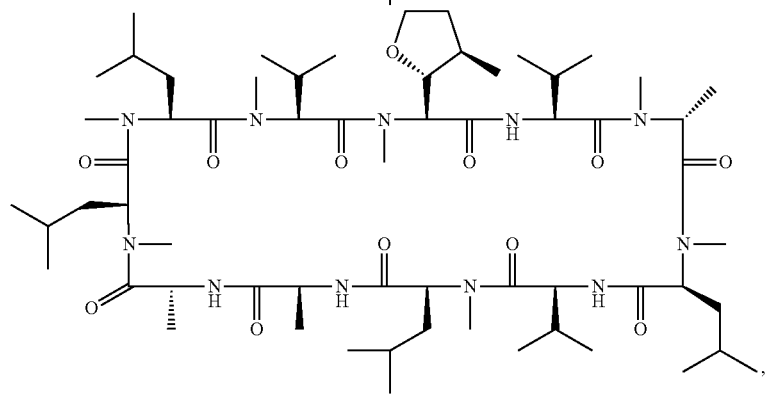,

-continued
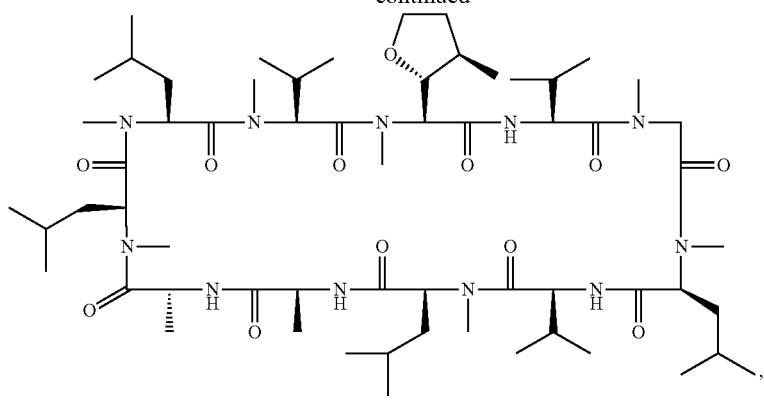
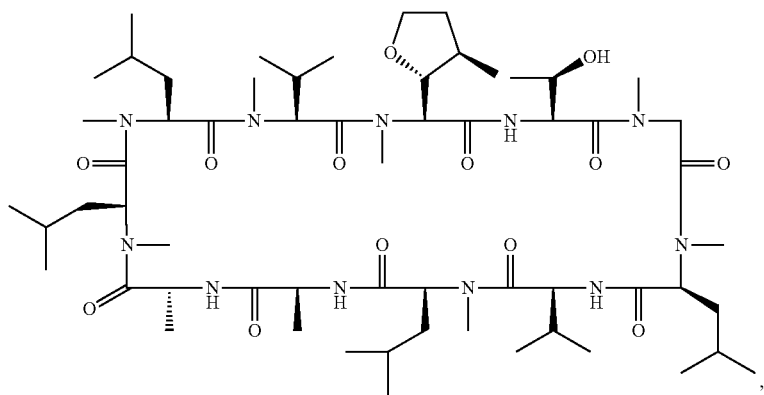
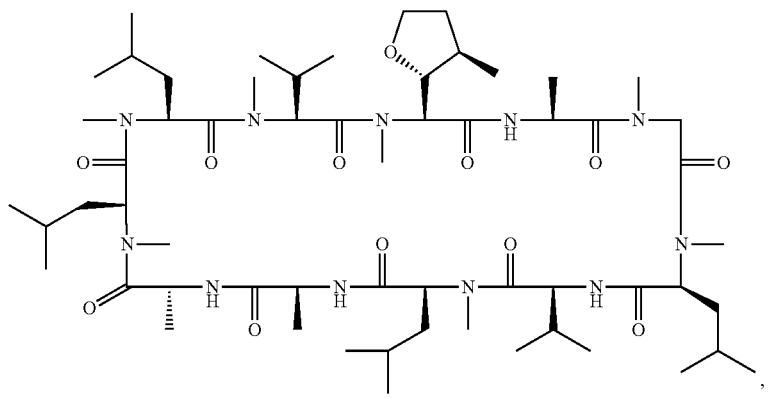
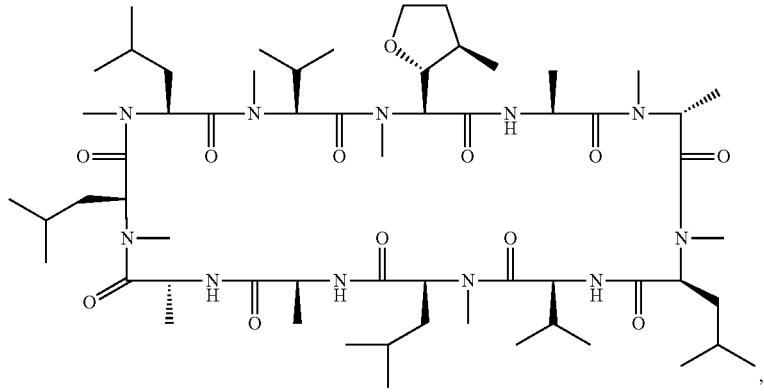

-continued
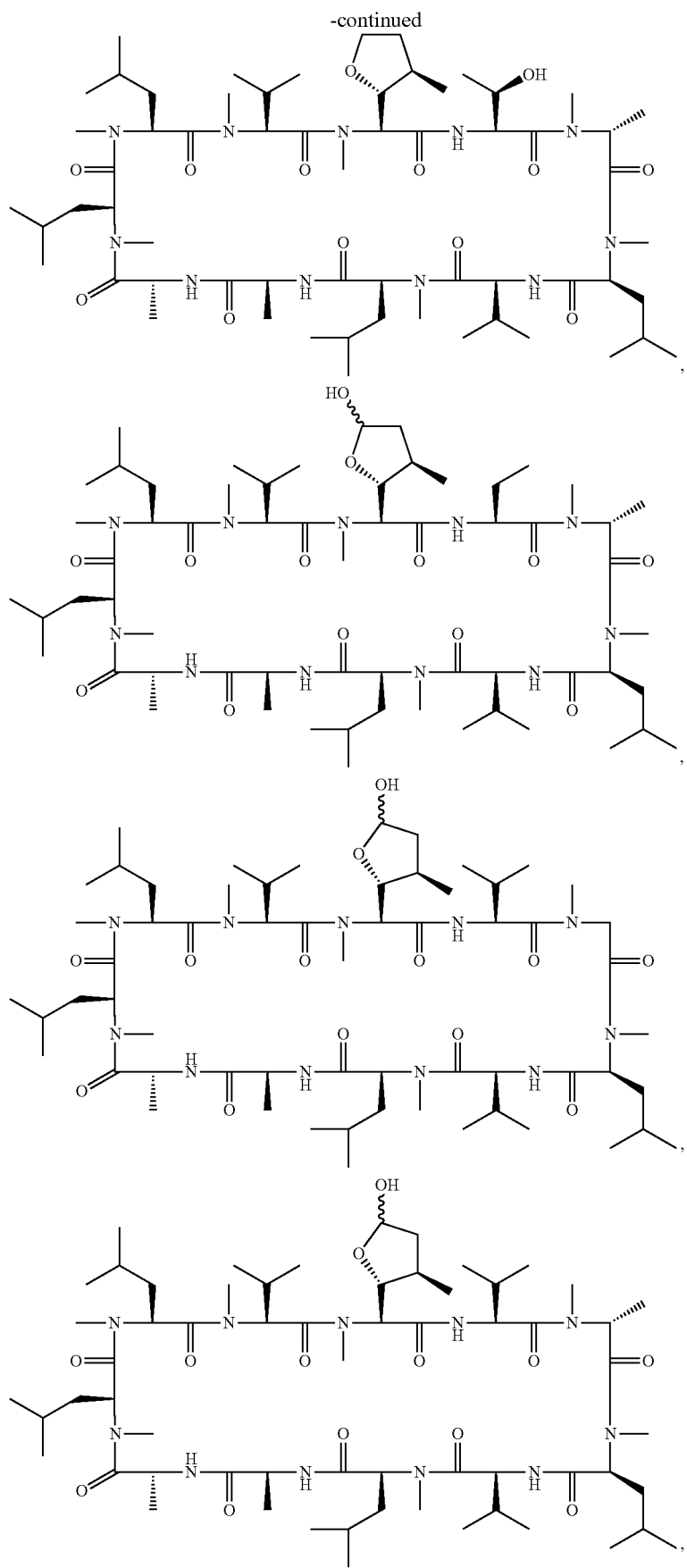

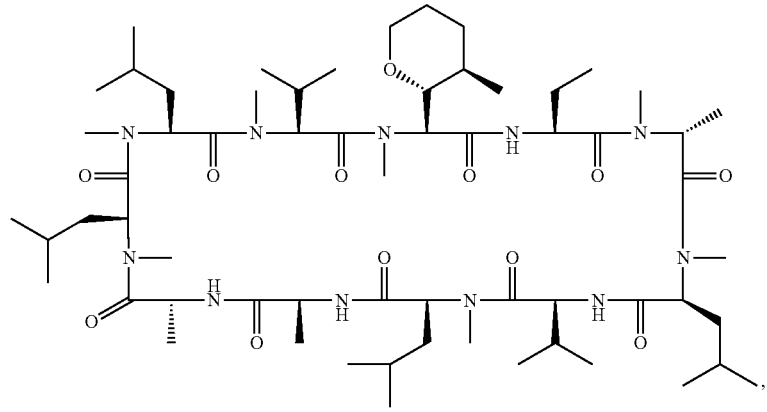
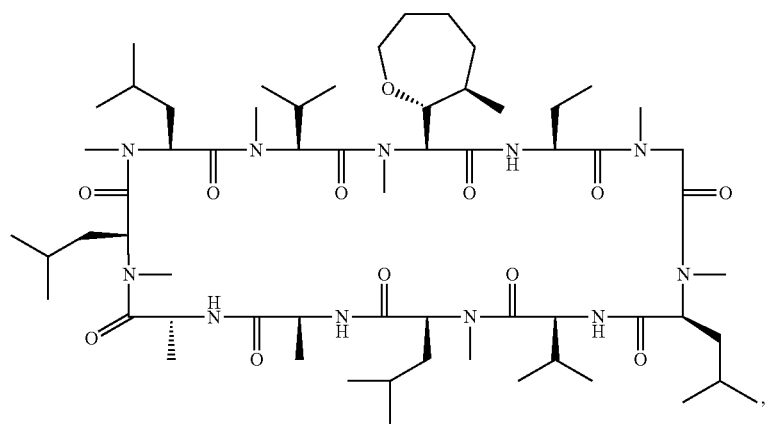
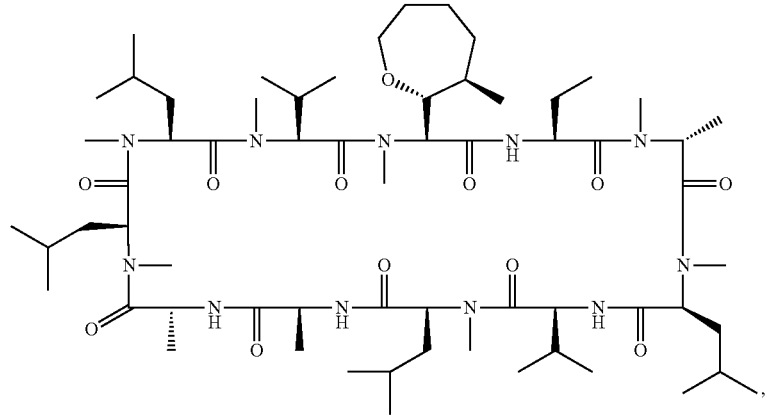
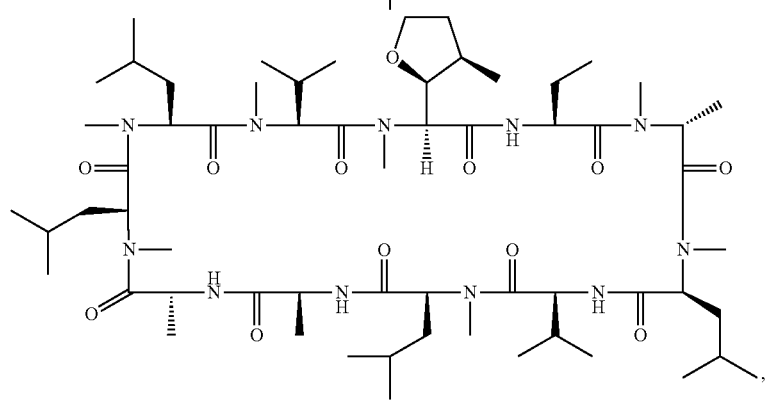

-continued
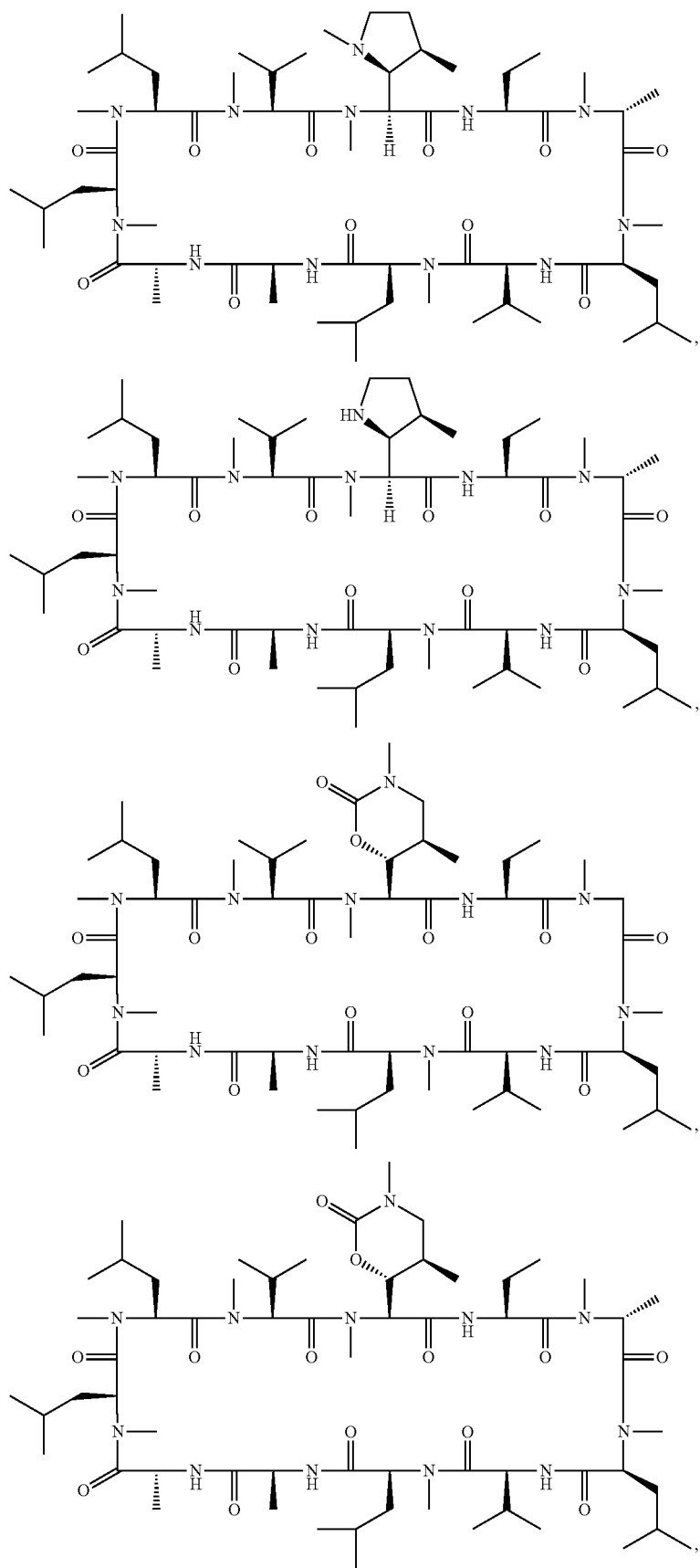

-continued
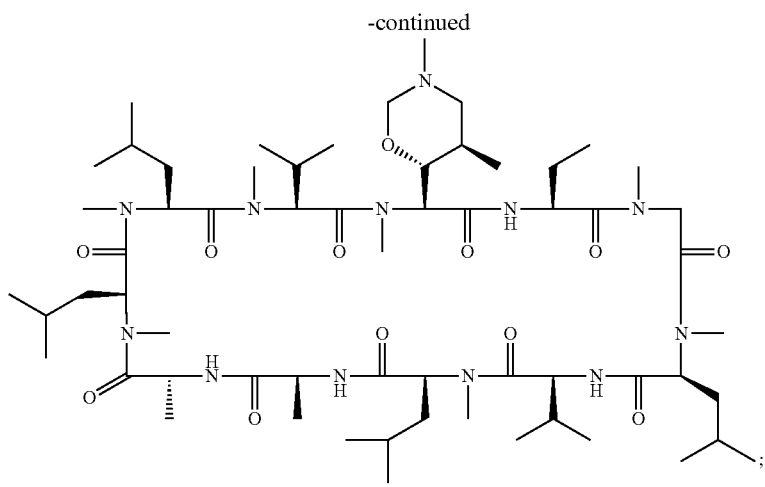
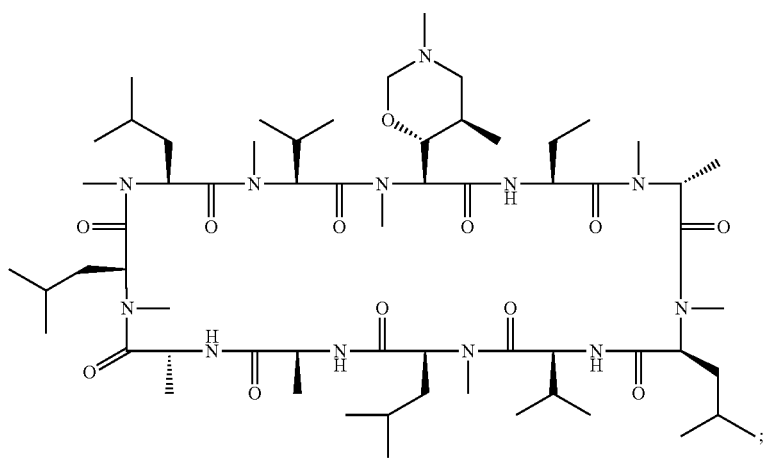
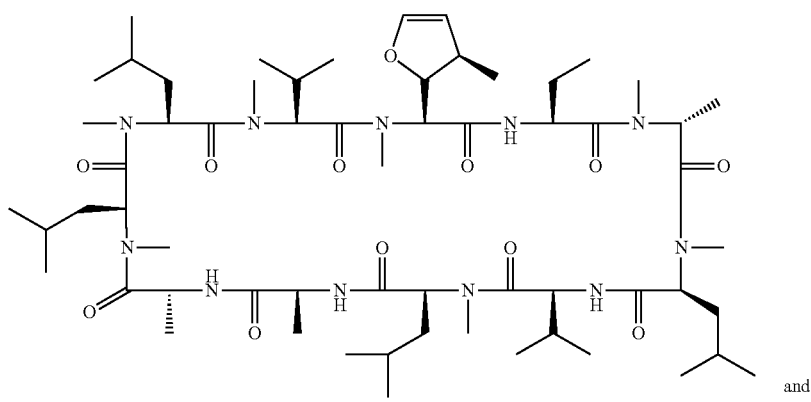
and

-continued

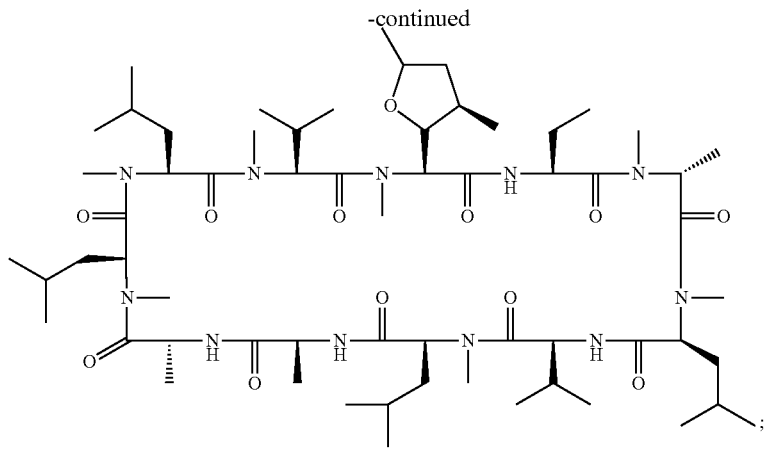

and pharmaceutically acceptable salts thereof.

In embodiment (46), the invention provides for a compound of embodiment (1) selected from the group consisting of:

[(2S)-2-(methylamino)-2-[(2R,3R)-3-methyltetrahydrofuran-2-yl]acetic acid]$^1$ [(R)-ethyl-Sar]3 cyclosporin A;
[(2S)-2-(methylamino)-2-[(2R,3R)-3-methyltetrahydrofuran-2-yl]acetic acid]$^1$ [(R)-propyl-Sar]$^3$ cyclosporin A;
[(2S)-2-(methylamino)-2-[(2R,3R)-3-methyltetrahydrofuran-2-yl]acetic acid]$^1$[(R)-methyl-Sar]$^3$ cyclosporin A;
[(2S)-2-(methylamino)-2-[(2R,3R)-3-methyltetrahydrofuran-2-yl]acetic acid]$^1$ cyclosporin A;
[(2S)-2-(methylamino)-2-[(2R,3R)-3-methyltetrahydrofuran-2-yl]acetic acid]$^1$ [(S)-difluoromethyl-Sar]$^3$ cyclosporin A;
[(2S)-2-(methylamino)-2-[(2R,3R)-3-methyltetrahydrofuran-2-yl]acetic acid]$^1$ [(R)-methyl-Sar]$^3$ cyclosporin D;
[(2S)-2-(methylamino)-2-[(2R,3R)-3-methyltetrahydrofuran-2-yl]acetic acid]$^1$ cyclosporin D;
[(2S)-2-(methylamino)-2-[(2R,3R)-3-methyltetrahydrofuran-2-yl]acetic acid]$^1$ cyclosporin C;
[(2S)-2-(methylamino)-2-[(2R,3R)-3-methyltetrahydrofuran-2-yl]acetic acid]$^1$ cyclosporin B;
[(2S)-2-(methylamino)-2-[(2R,3R)-3-methyltetrahydrofuran-2-yl]acetic acid]$^1$ [(R)-methyl-Sar]$^3$ cyclosporin B;
[(2S)-2-(methylamino)-2-[(2R,3R)-3-methyltetrahydrofuran-2-yl]-2-acetic acid]$^1$ [(R)-methyl-Sar]$^3$ cyclosporin C;
[(2R)-2-[(2R,3R)-5-hydroxy-3-methyl-tetrahydrofuran-2-yl]-2-(methylamino)acetic acid]$^1$ [(R)-methyl-Sar]$^3$ cyclosporin A;
[(2S)-2-[(2R,3R)-5-Hydroxy-3-methyl-tetrahydrofuran-2-yl]-2-(methylamino)acetic acid]$^1$ cyclosporin D;
[(2S)-2-[(2R,3R)-5-Hydroxy-3-methyl-tetrahydrofuran-2-yl]-2-(methylamino)acetic acid]$^1$ [(R)-methyl-Sar]$^3$ cyclosporin D;
[(2S)-2-(methylamino)-2-[(2R,3R)-3-methyltetrahydropyran-2-yl]acetic acid]$^1$ [(R)-methyl-Sar]$^3$ cyclosporin A;
[(2S)-2-(methylamino)-2-[(2R,3R)-3-methyloxepan-2-yl] acetic acid]$^1$ cyclosporin A;
[(2S)-2-(methylamino)-2-[(2R,3R)-3-methyloxepan-2-yl] acetic acid]$^1$ [(R)-methyl-Sar]$^3$ cyclosporin A;
[(2S)-2-(methylamino)-2-[(2S,3R)-3-methyltetrahydrofuran-2-yl]acetic acid]$^1$ [(R)-methyl-Sar]$^3$ cyclosporin A;
[(2S)-2-[(2S,3R)-1,3-dimethylpyrrolidin-2-yl]-2-(methylamino)acetic acid]$^1$ [(R)-methyl-Sar]$^3$ cyclosporin A;
[(2S)-(methylamino)-2-[(2S,3R)-3-methylpyrrolidin-2-yl] acetic acid]$^1$ [(R)-methyl-Sar]$^3$ cyclosporin A;
[(2R)-2-[(5R,6R)-3,5-dimethyl-2-oxo-1,3-oxazinan-6-yl]-2-(methylamino)acetic acid]$^1$ cyclosporin A;
(2S)-2-[5R,6R)-3,5-Dimethyl-2-oxo-1,3-oxazinan-6-yl]-2-(methylamino)acetic acid]$^1$ [(R)-methyl-Sar]$^3$ cyclosporin A;
[(2R)-2-[(5R,6R)-3,5-dimethyl-1,3-oxazinan-6-yl]-2-(methylamino)acetic acid]$^1$ cyclosporin A;
(2S)-2-[5R,6R)-3,5-Dimethyl-1,3-oxazinan-6-yl]-2-(methylamino)acetic acid]$^1$ [(R)-methyl-Sar]$^3$ cyclosporin A;
[(2S)-2-(methylamino)-2-[(2R,3R)-3-methyl-2,3-dihydrofuran-2-yl]acetic acid]$^1$ [(R)-methyl-Sar]$^3$ cyclosporin A; and
[(2S)-2-[(2R,3R)-3,5-dimethyltetrahydrofuran-2-yl]-2-(methylamino)acetic acid]$^1$ [(R)-methyl-Sar]$^3$ cyclosporin A;

and pharmaceutically acceptable salts thereof.

In embodiment (47), there is provided a pharmaceutical composition comprising a compound of any one of embodiments (1) through (46) and a pharmaceutically acceptable excipient.

In embodiment (48), there is provided a pharmaceutical composition comprising a therapeutically effective amount of a compound of any one of embodiments (1) through (46) and a pharmaceutically acceptable excipient.

In embodiment (49), there is provided a use of a compound of any one of embodiments (1) through (46) in the preparation of a medicament for the treatment of an ischemic condition.

In embodiment (50), there is provided a method of treating an ischemic condition in a subject, the method comprising administering a compound of any one of embodiments (1) through (46), or a composition of embodiment (47) or (48), to the subject, thereby treating the ischemic condition.

In embodiment (51), there is provided a method of treating an ischemic condition in a subject, the method comprising administering a therapeutically effective amount of a compound of any one of embodiments (1) through (46), or a therapeutically effective amount of a composition of embodiment (47) or (48), to the subject, thereby treating the ischemic condition.

In embodiment (52), there is provided the method of embodiment (50) or (51), wherein the ischemic condition is an ischemia-reperfusion injury.

In embodiment (53), there is provided the method of embodiment (52), wherein the ischemia-reperfusion injury is a myocardial ischemia-reperfusion injury.

In embodiment (54), there is provided the method of embodiment (53), wherein the treatment comprises protecting the subject's myocardial cells and/or tissue from the myocardial ischemia-reperfusion injury.

In embodiment (55), there is provided the method of embodiment (53) or (54), wherein the ischemic condition is associated with a myocardial infarct.

In embodiment (56), there is provided the method of embodiment (52), wherein the ischemia-reperfusion injury is a cerebral ischemia-reperfusion injury.

In embodiment (57), there is provided the method of embodiment (56), wherein the treatment comprises protecting the subject's brain cells and/or tissue from the cerebral ischemia-reperfusion injury.

In embodiment (58), there is provided the method of any one of embodiments (50) through (57), wherein the ischemic condition is associated with artery obstruction, artery constriction or rapid irregular heartbeat.

In embodiment (59), there is provided the method of embodiment (52), wherein the ischemia-reperfusion injury is an ocular ischemia-reperfusion injury.

In embodiment (60), there is provided the method of embodiment (59), wherein the treatment comprises protecting the subject's ocular cells and/or tissue from the ocular ischemia-reperfusion injury.

In embodiment (61), there is provided the method of embodiment (52), wherein the ischemia-reperfusion injury is a retinal ischemia-reperfusion injury.

In embodiment (62), there is provided the method of embodiment (61), wherein the treatment comprises protecting the subject's retinal cells and/or tissue from the retinal ischemia-reperfusion injury.

In embodiment (63), there is provided the method of embodiment (62), wherein the cells are retinal ganglion cells.

In embodiment (64), there is provided the method of embodiment (59) or (60), wherein the treatment comprises protecting the subject from optic nerve degeneration.

In embodiment (65), there is provided the method of any one of embodiments (50), (51) and (59) through (64), wherein the ischemic condition is associated with increased intraocular pressure, central retinal vein or artery occlusion, macular degeneration, diabetes or glaucoma.

In embodiment (66), there is provided the method of any one of embodiments (50) through (65), wherein the subject is a human.

In other aspects, the invention provides for methods of preparing compounds of Formula I. Compounds having Formula I may be prepared according to the following reaction schemes and accompanying disclosures. Unless otherwise indicated, the variable groups, including $R^1$, $R^2$, $R^3$, $R^4$, $R^5$, $R^6$, $R^7$, $R^8$, $R^9$, $R^{10}$, $R^{11}$, $R^{12}$, $R^{13}$, m, n, X, Y, Z, and W, in the following reaction schemes and discussion, are as defined above in the Summary of the Invention.

The present invention includes isotopically-labeled compounds of Formula I. For Example, a compound having Formula I may contain one or more isotopic atoms such as deuterium $^2H$ (or D) in place of proton $^1H$ (or H) or $^{13}C$ in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

Isotopically-labeled compounds of the present invention are identical to those recited herein, except that one or more atoms in the compound are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{123}I$, respectively.

Some compounds of Formula I of the invention are listed and described in Tables 1-5, and include their pharmaceutically acceptable salts. In Tables 1-5, the symbol "-" means absent or not-applicable, and "*" represents the point of attachment of $R^1$ to the macrocyclic undecapeptide.

TABLE 1

Compounds of Formula I, wherein: $R^1$ is as shown [X is O; Y is $CR^9R^{10}$, wherein each of $R^9$ and $R^{10}$ is H; Z is $(CH_2)_m$, wherein m is 1; and n is 0]; $R^4$ is —$CH_3$; $R^5$ is —$CH_2CH(CH_3)_2$; $R^6$ is —$CH_3$; and the bond joining Y and Z is a single bond.

| Cmpd No. | $R^1$ | $R^2$ | $R^3$ |
|---|---|---|---|
| 1 | (tetrahydrofuran-3-yl) | —Et | —Et |
| 2 | (tetrahydrofuran-3-yl) | —Et | —nPr |
| 3 | (tetrahydrofuran-3-yl) | —Et | —Me |
| 4 | (tetrahydrofuran-3-yl) | —Et | —H |
| 5 | (tetrahydrofuran-3-yl) | —Et | —$CHF_2$ |
| 6 | (tetrahydrofuran-3-yl) | —iPr | —Me |
| 7 | (tetrahydrofuran-3-yl) | —iPr | —H |

TABLE 1-continued

Compounds of Formula I, wherein: $R^1$ is as shown [X is O; Y is $CR^9R^{10}$, wherein each of $R^9$ and $R^{10}$ is H; Z is $(CH_2)_m$, wherein m is 1; and n is 0]; $R^4$ is —$CH_3$; $R^5$ is —$CH_2CH(CH_3)_2$; $R^6$ is —$CH_3$; and the bond joining Y and Z is a single bond.

| Cmpd No. | $R^1$ | $R^2$ | $R^3$ |
|---|---|---|---|
| 8 | (tetrahydrofuran structure) | —CH(OH)CH$_3$ | —H |
| 9 | (tetrahydrofuran structure) | —Me | —H |
| 10 | (tetrahydrofuran structure) | —Me | —Me |
| 11 | (tetrahydrofuran structure) | —CH(OH)CH$_3$ | —Me |
| 18 | (tetrahydrofuran structure) | —Et | —Me |

TABLE 2

Compounds of Formula I, wherein: $R^1$ is as shown [X is O; Y is $CR^{11}$ (wherein $R^{11}$ is H) or $CR^9R^{10}$ (wherein $R^9$ is H, OH or —$C_{1-6}$alkyl, which is methyl, and $R^{10}$ is H); Z is $CR^{12}$ (wherein $R^{12}$ is H) or $(CH_2)_m$, wherein m is 1; and n is 0]; $R^4$ is —$CH_3$; $R^5$ is —$CH_2CH(CH_3)_2$; $R^6$ is —$CH_3$; and the bond joining Y and Z is a single or double bond; provided that: (a) when the bond joining Y and Z is a single bond, then Y is $CR^9R^{10}$ and Z is $(CH_2)_m$; and (b) when the bond joining Y and Z is a double bond, then Y is $CR^{11}$ and Z is $CR^{12}$.

| Cmpd No. | $R^1$ | $R^2$ | $R^3$ | $R^9$ | $R^{10}$ | $R^{11}$ | $R^{12}$ |
|---|---|---|---|---|---|---|---|
| 12 | HO-(structure) | —Et | —Me | OH | H | — | — |
| 13 | HO-(structure) | —iPr | —H | OH | H | — | — |

TABLE 2-continued

Compounds of Formula I, wherein: $R^1$ is as shown [X is O; Y is $CR^{11}$ (wherein $R^{11}$ is H) or $CR^9R^{10}$ (wherein $R^9$ is H, OH or —$C_{1-6}$alkyl, which is methyl, and $R^{10}$ is H); Z is $CR^{12}$ (wherein $R^{12}$ is H) or $(CH_2)_m$, wherein m is 1; and n is 0]; $R^4$ is —$CH_3$; $R^5$ is —$CH_2CH(CH_3)_2$; $R^6$ is —$CH_3$; and the bond joining Y and Z is a single or double bond; provided that: (a) when the bond joining Y and Z is a single bond, then Y is $CR^9R^{10}$ and Z is $(CH_2)_m$; and (b) when the bond joining Y and Z is a double bond, then Y is $CR^{11}$ and Z is $CR^{12}$.

| Cmpd No. | $R^1$ | $R^2$ | $R^3$ | $R^9$ | $R^{10}$ | $R^{11}$ | $R^{12}$ |
|---|---|---|---|---|---|---|---|
| 14 | HO-(structure) | —iPr | —Me | OH | H | — | — |
| 25 | (dihydrofuran structure) | —Et | —Me | H | H | H | H |
| 26 | (structure) | —Et | —Me | Me | H | — | — |

TABLE 3

Compounds of Formula I, wherein $R^1$ is as shown [X is O; Y is $CR^9R^{10}$, wherein each of $R^9$ and $R^{10}$ is H; Z is $(CH_2)_m$, wherein m is 2 or 3; W is $(CH_2)_n$, wherein n is 0]; $R^4$ is —$CH_3$; $R^5$ is —$CH_2CH(CH_3)_2$; $R^6$ is —$CH_3$; and the bond joining Y and Z is a single bond.

| Cmpd No. | $R^1$ | $R^2$ | $R^3$ |
|---|---|---|---|
| 15 | (tetrahydropyran structure) | —Et | —Me |
| 16 | (oxepane structure) | —Et | —H |
| 17 | (oxepane structure) | —Et | —Me |

TABLE 4

Compounds of Formula I, wherein: $R^1$ is as shown [X is $NR^8$, wherein $R^8$ is H or —$C_{1-6}$alkyl, which is methyl; Y is $CR^9R^{10}$, wherein each of $R^9$ and $R^{10}$ is H; Z is $(CH_2)_m$, wherein m is 1; and n is 0]; $R^4$ is —$CH_3$; $R^5$ is —$CH_2CH(CH_3)_2$; $R^6$ is —$CH_3$; and the bond joining Y and Z is a single bond.

| Cmpd No. | $R^1$ | $R^2$ | $R^3$ |
|---|---|---|---|
| 19 | (N-methyl pyrrolidinyl) | —Et | —Me |
| 20 | (NH pyrrolidinyl) | —Et | —Me |

TABLE 5

Compounds of Formula I, wherein: $R^1$ is as shown [X is O; Y is C=O or $CR^9R^{10}$, wherein each of $R^9$ and $R^{10}$ is H; Z is $NR^{13}$, wherein $R^{13}$ is —$C_{1-6}$alkyl, which is methyl; W is $(CH_2)_n$, wherein n is 1]; $R^4$ is —$CH_3$; $R^5$ is —$CH_2CH(CH_3)_2$; $R^6$ is —$CH_3$; and the bond joining Y and Z is a single bond.

| Cmpd No. | $R^1$ | $R^2$ | $R^3$ | $R^9$ | $R^{10}$ |
|---|---|---|---|---|---|
| 21 | (oxazinanone) | —Et | —H | — | — |
| 22 | (oxazinanone) | —Et | —Me | — | — |
| 23 | (morpholinyl) | —Et | —H | H | H |
| 24 | (morpholinyl) | —Et | —Me | H | H |

The present invention further provides synthetic intermediates and compounds formed by the schemes set forth herein. Compounds of the invention may be synthesized in a variety of ways known to those skilled in the art.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

As shown in the following schemes, the starting material for compounds of Formula I is cyclosporin A (CAS Number 59865-13-3). Cyclosporin A may be obtained commercially from suppliers such as Sigma-Aldrich (St. Louis, Mo., United States) or TCI America (Portland, Oreg., United States). Other cyclosporin starting materials such as Cyclosporin D (CAS Registry Number 63775-96-2) may also be obtained through commercial suppliers such as Enzo Life Sciences (Ann Arbor, Mich., United States; Farmingdale, N.Y., United States). Other cyclosporin starting materials may be prepared from cyclosporin A as described by M. Mutter et al. Tet. Lett. 2000, 41, 7193-7196, U.S. Pat. No. 5,214,130 and WO2013181339.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

In general, characterization of the compounds is performed according to the following methods: Proton nuclear magnetic resonance ($^1$H NMR) and carbon nuclear magnetic resonance ($^{13}$C NMR) spectra were recorded on a Bruker 300 or 500 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, integrated intensity, assignment). Characteristic resonances of compounds of the invention are reported.

Electron spray mass spectra (ESMS) were recorded on a Micromass ZQ mass spectrometer.

The following abbreviations used in the following reaction schemes and accompanying discussions are defined as follows:
Ac acetyl, a group of formula "—(C=O)CH$_3$"
Ac$_2$O acetic anhydride
AcOH acetic acid
AlBN 2,2'-azobis(2-methylpropionitrile)
aq. KOH aqueous potassium hydroxide
BnNEt3$^+$Cl$^-$ benzyltriethylammonium chloride
BuLi n-butyl lithium
CH$_3$CN acetonitrile
CH$_2$Cl$_2$ dichloromethane
CDCl$_3$ deuterated chloroform
CD$_3$OD deuterated methanol
ClCH$_2$CH$_2$Cl dichloroethane
ClCO$_2$CHMeCl 1-chloromethylchloroformate
CCl$_4$ carbontetrachloride
CDI carbonyl diimidazole
CO$_2$ carbon dioxide
ClCO$_2$CH$_2$Cl chloromethylchloroformate
ClCO$_2$CH$_2$CH$_2$Cl 2-chloroethylchloroformate
Cs$_2$CO$_3$ cesium carbonate
CSA camphor sulphonic acid
CuI copper iodide
DBU 1,8-diazabicyclo[5.4.0]undec-7-ene
DCM dichloromethane
DEAD diethyl azodicarboxylate
DIBAL-H diisobutylaluminum hydride
DIPEA diisopropylethylamine
DMAP 4-dimethylaminopyridine
DMSO-d6 deuterated dimethyl sulfoxide
DMF N,N-dimethylformamide
ESMS MH$^+$ electrospray mass spectrum positive ion
Et ethyl, a group of formula "—CH$_2$CH$_3$"
Et$_2$O ether
Et$_3$N triethylamine
EtOAc ethylacetate
EtOH ethanol
Grubbs II catalyst Grubbs catalyst second generation, also known as (1,3-bis(2,4,6-trimethylphenyl)-2-imidazolidinylidene) dichloro (phenylmethylene)(tricyclohexylphosphine)ruthenium
H2 or H$_2$ hydrogen gas
HCl hydrochloric acid
H-cube continuous flow hydrogenation apparatus
Hg(OAc)$_2$ mercer (II) acetate
HOBt-EDC N-hydroxybenzotriazole 1-ethyl-3-(3-dimethylaminopropyl) carbodiimide hydrochloride
i-Pr isopropyl
i-Pr$_2$NH diisopropylamine
i-BuOC(O)Cl isobutyl chloroformate
K$_2$CO$_3$ potassium carbonate
LAH or LiAlH$_4$ lithium aluminium hydride
LDA lithium diisopropylamide
LiOH lithium hydroxide
M molar concentration (molarity)
Me methyl, a group of formula "—CH$_3$"
MeI methyl iodide
MeOH methanol
MeSO$_2$Cl methane sulphonyl chloride
MeSSMe dimethyl disulphide
MgSO$_4$ magnesium sulfate
MPLC medium pressure liquid chromatography
n-Bu n-butyl
n-BuLi n-butyllithium
n-Bu$_4$NOH tetrabutylammonium hydroxide
NB S N-bromosuccinimide
NH$_3$ ammonia
NH$_2$NH$_2$ hydrazine
NMO 4-methylmorpholine N-oxide
NaOMe sodium methoxide
NaBH$_4$ sodium borohydride
NaCNBH$_3$ sodium triacetoxyborohydride
NaBH(OAc)$_3$ sodium triacetoxyborohydride
TMPMgCl.LiCl 2,2,6,6-tetramethylpiperidinylmagnesium chloride lithium chloride complex solution
NaH sodium hydride
NH$_4$Cl ammonium chloride
ozone
o/n overnight
OTBDMS t-butyldimethylsilyloxy
10% Pd/C 10% palladium on carbon
PdCl$_2$(PPh$_3$)$_2$ bis(triphenylphosphine)palladium(II) chloride
PdCl$_2$(CH$_3$CN)$_2$ bis(acetonitrile)dichloropalladium(II)
Pd(PPh$_2$)$_4$ tetrakistriphenylphosphine palladium(0)
Ph$_3$P triphenylphosphine
PhSSPh diphenyl disulphide
PTLC preparative thin Layer Chromatography
RT room temperature
TFA trifluoroacetic acid
THF tetrahydrofuran
TPAP tetrapropylammonium perruthenate
TBDMSOTf t-butyldimethylsilyl trifluoromethanesulphonate
OTBDMS O-t-butyldimethylsilyl
TBDMS t-butyldimethylsilyl
TBAF tetrabutylammonium fluoride
TBDMS t-butyldimethylsilyl
TEA trimethylamine The following synthetic schemes illustrate how compounds according to the invention can be made. Those skilled in the art will be routinely able to modify and/or adapt the following schemes to synthesize any compound of the invention covered by Formula I.

Example A
Compounds of Formula I wherein X is O, Y is $CR^9R^{10}$, $R^9$ and $R^{10}$ is H, Z is $(CH_2)_m$ and m is 1, 2 or 3 are prepared from intermediates of Formula (II).
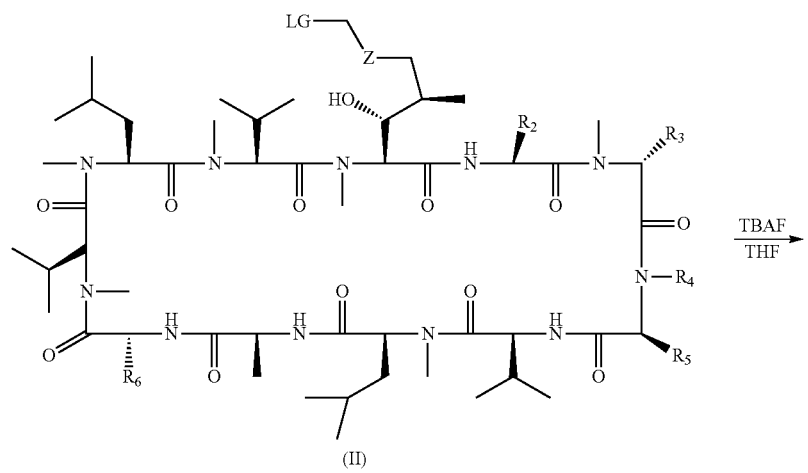
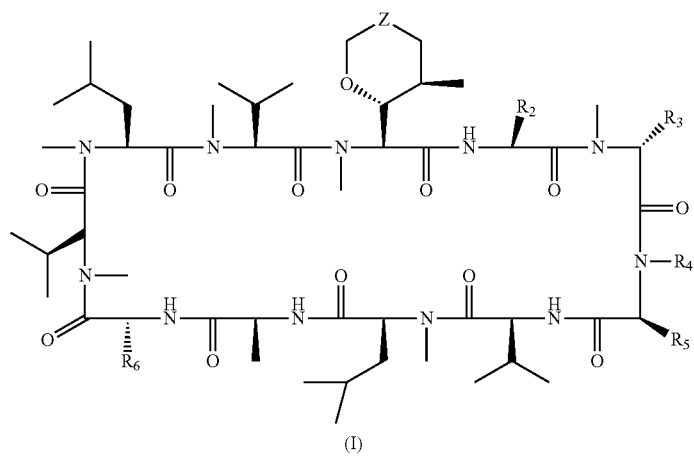

wherein LG is a leaving group such as mesylate, tosylate or halide. The secondary alcohol may also be protected by a protecting group such as TBDMS. The cyclisation maybe carried out using TBAF in a solvent such as THF.

Compounds of Formula (II) are prepared by reaction of compounds of Formula (III) with methanesulphonyl chloride or p-toluenesulphonyl chloride in the presence of base such as triethylamine or pyridine in a solvent such as DCM.

Compounds of Formula (III) are prepared as described in WO2013181339.

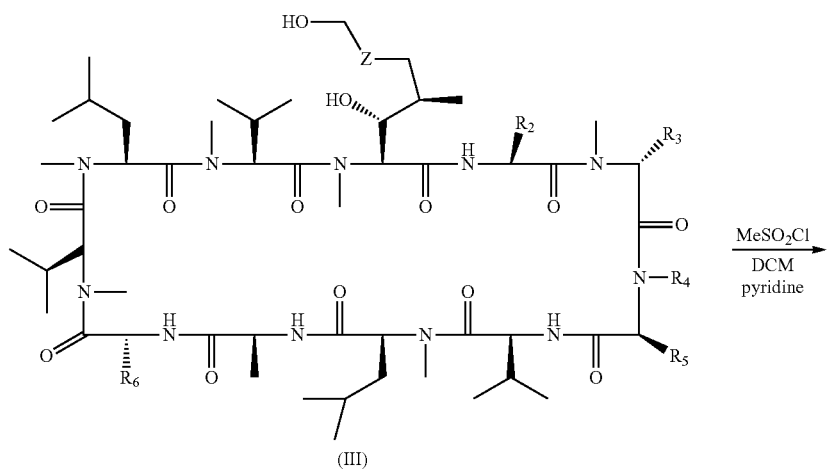

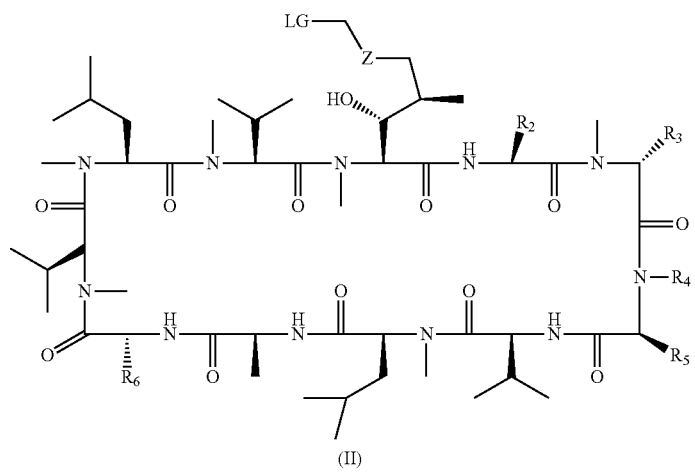

Example B

Compounds of Formula I where X is O, Y is $CR^9R^{10}$, each of $R^9$ and $R^{10}$ is H, Z is $(CH_2)_m$, and $R^3$ is $C_{1-6}$alkyl or $C_{1-6}$haloalkyl, may also be prepared from Compounds of Formula I where X is O, Y is $CR^9R^{10}$, each of $R^9$ and $R^{10}$ is H, Z is $(CH_2)_m$, and $R^3$ is H, by lithiation with bases such as n-butyl lithium and 2,2,6,6-tetramethylpiperidinylmagnesium chloride lithium chloride solution in THF and quenching with an alkyl halide such as methyl iodide or n-propyl bromide.

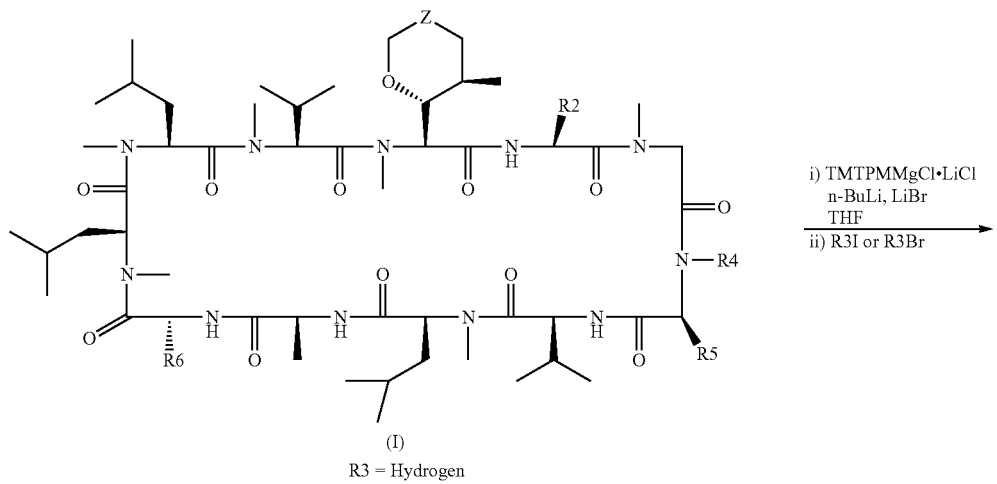

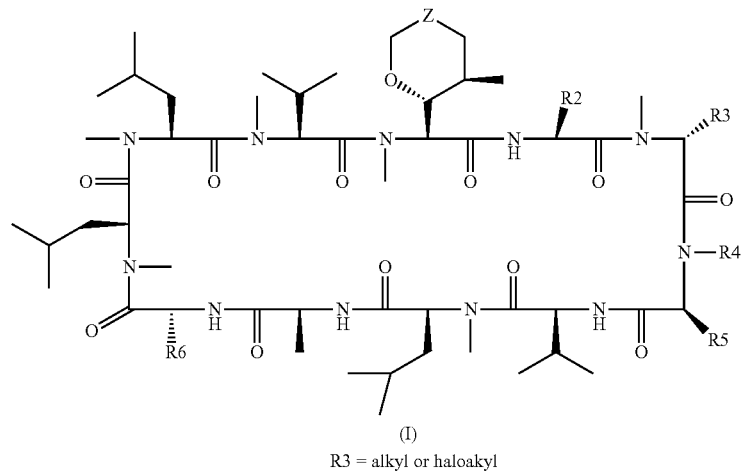

Example C
The epimer at the 2-position of the $R^1$ heterocycle of compounds of Formula I, wherein X is O, Y is $CR^9R^{10}$, each of $R^9$ and $R^{10}$ is H, Z is $(CH_2)_m$, are prepared from intermediates of Formula (III) by heating in solvent such as toluene in the presence of p-Toluene sulphonic acid.
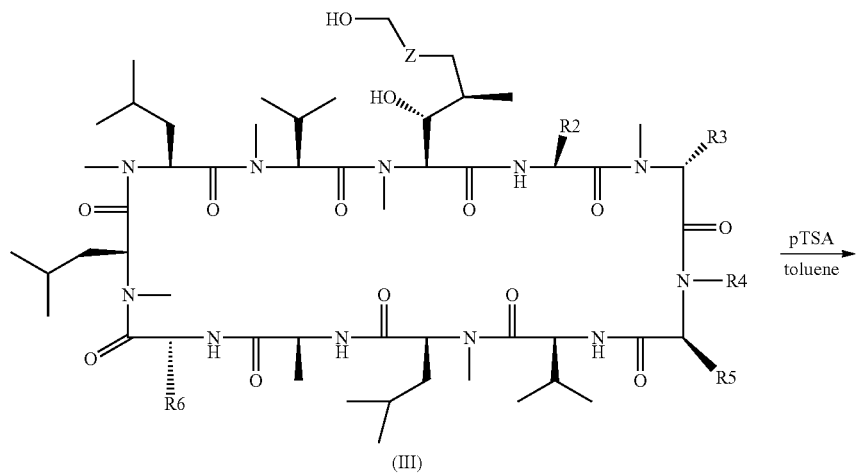
(III)
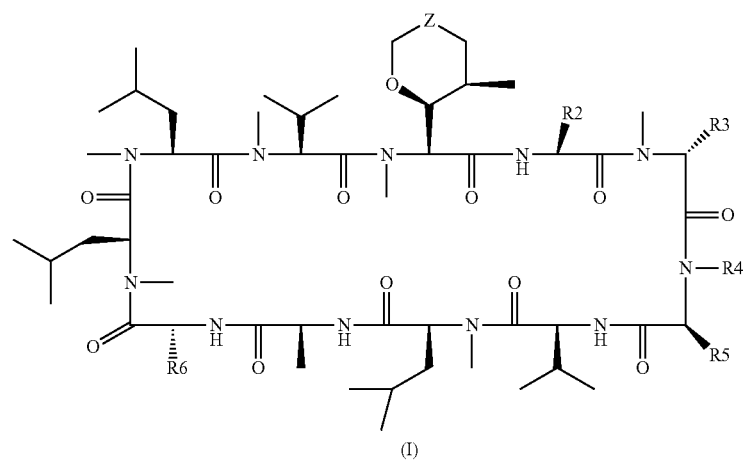
(I)

Example D
Compounds of Formula I where X is O, Y is C=O and Z is NR$^{13}$ are prepared from compounds of Formula IV by cyclization to give the required product by reaction with carbonyl diimidazole in a solvent such as THF.
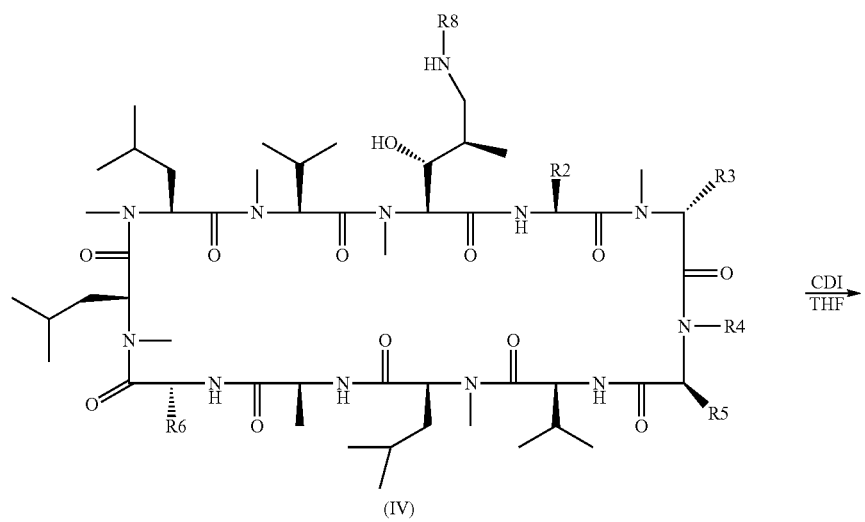
(IV)
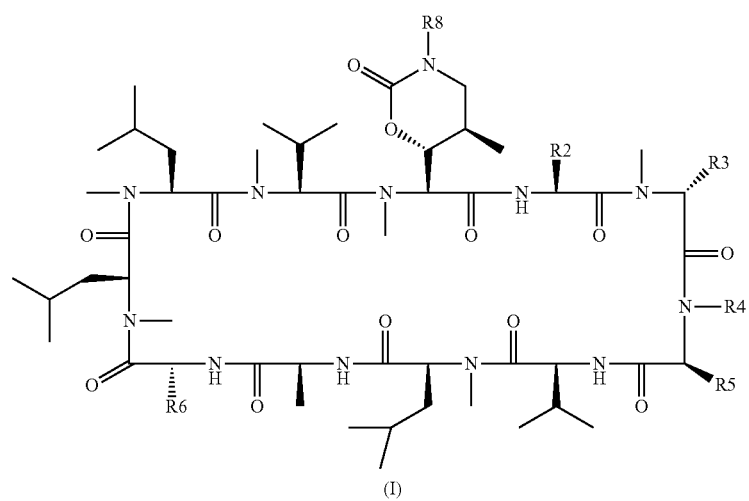
(I)

Example E
Compounds of Formula I wherein X is O, Y is CH$_2$ and Z is NR$^{13}$ are prepared from compounds of Formula IV by cyclization to give the required product by reaction with formaldehyde in a solvent such as methanol.
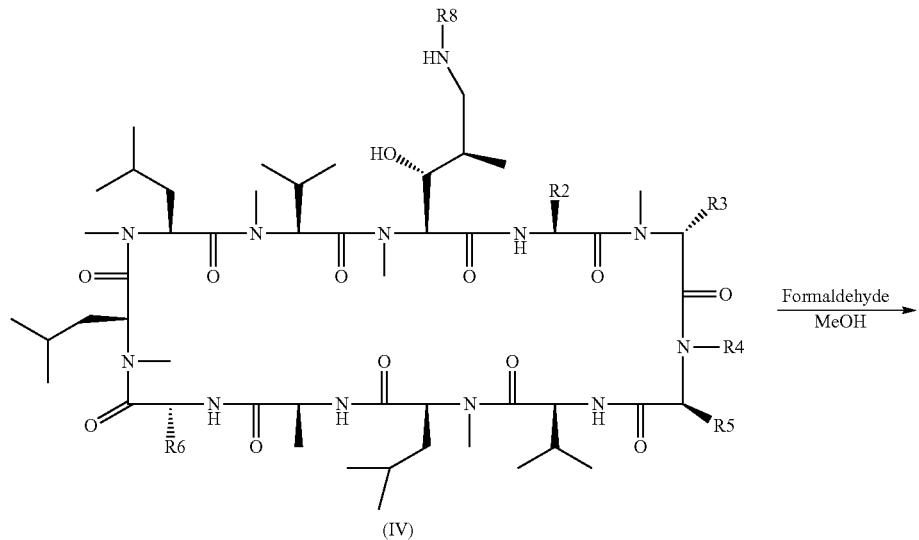

Example F
Compounds of Formula IV are prepared from compounds of Formula V by reductive amination of a compound of Formula V using an amine H₂NR in a solvent such DCM or THF in the presence of a reducing agent such sodium triacetoxy borohydride as described in WO2013181339. Compounds of Formula V are prepared as described in WO2013181339.
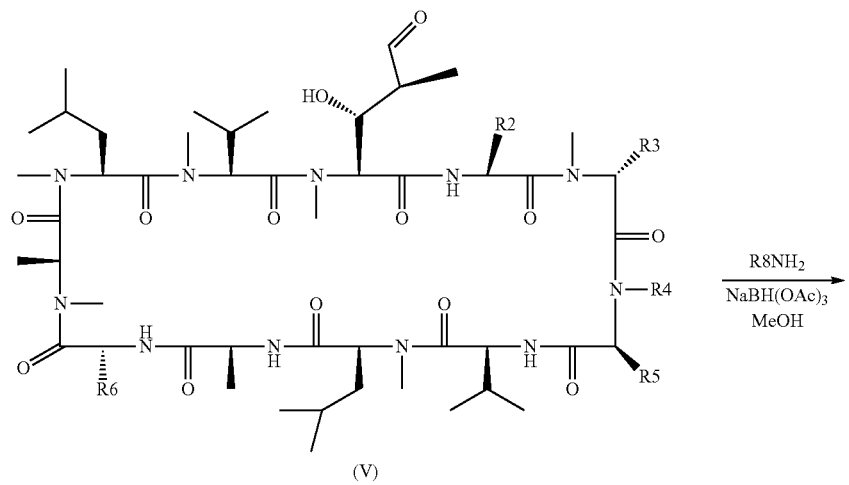
(V)
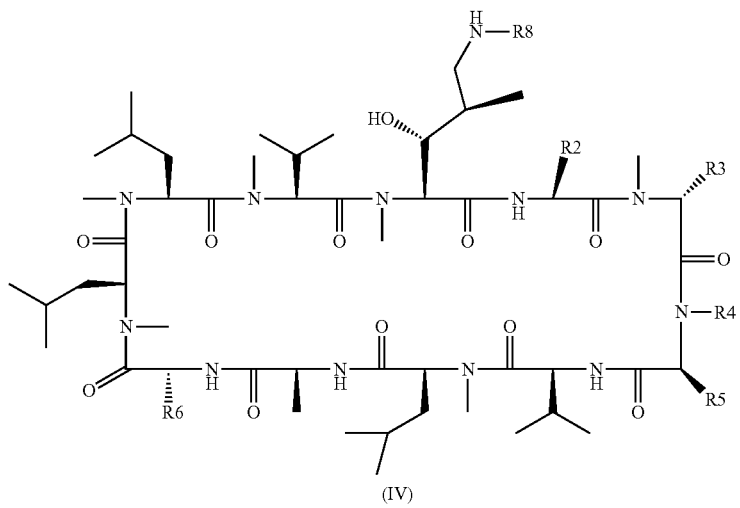
(IV)

Example G
Compounds of Formula I wherein X is O, Y is C=O, and Z is $(CH_2)_m$, are prepared from compounds of Formula VI by cyclisation to give the lactone by heating in a solvent such as toluene with an acid such as pTSA.
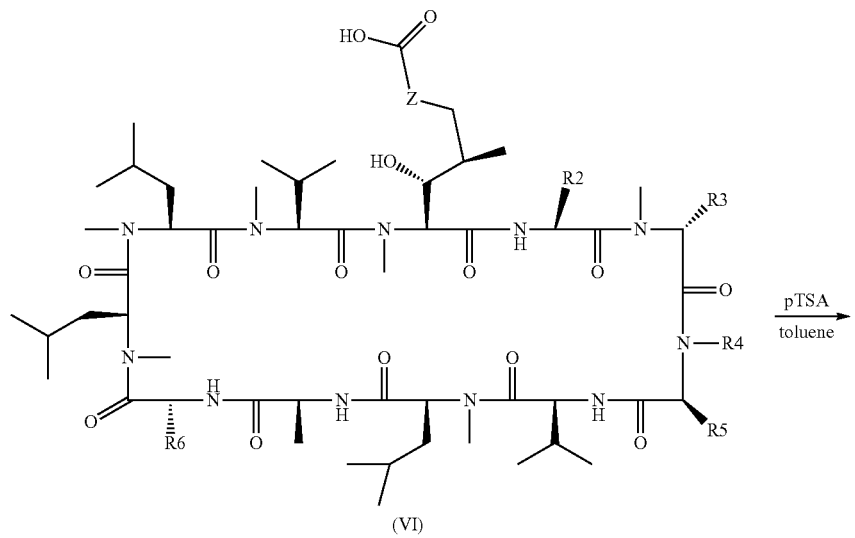
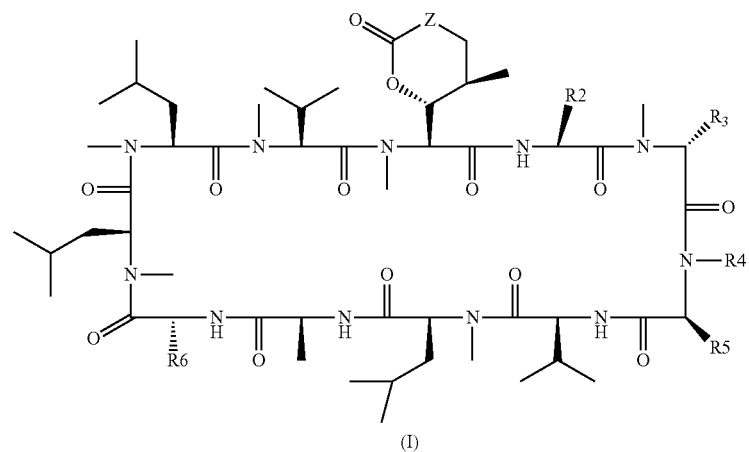

Example H

Compounds of Formula VI are prepared from compounds of Formula VII by deprotection with TBAF in a solvent such as toluene. Compounds of the Formula V are prepared by oxidation of compounds of the Formula VIII using sodium hydrogen phosphate, sodium chlorite and dimethylbutene in t-butanol and THF. Compounds of Formula VIII are prepared as described in WO2013181339.

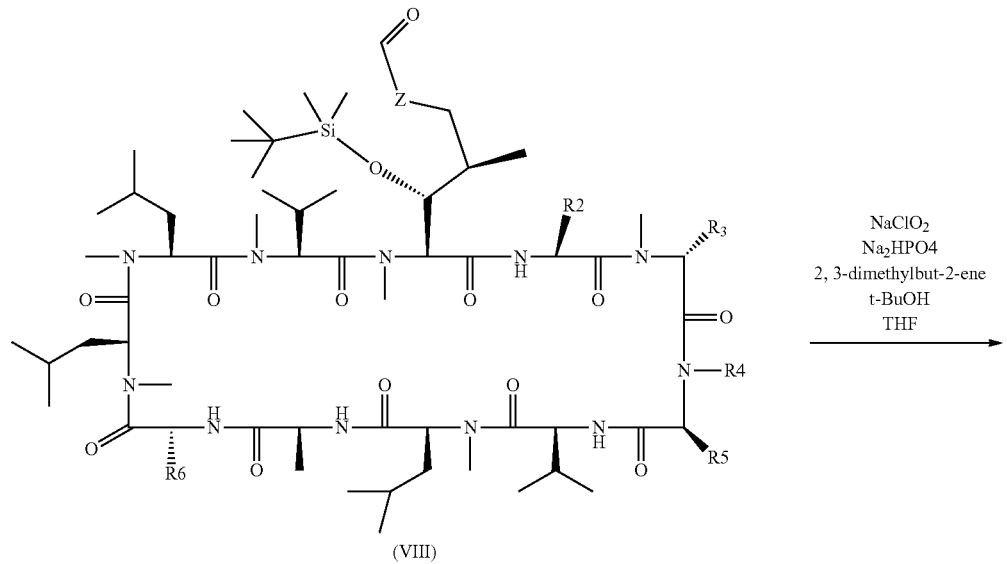

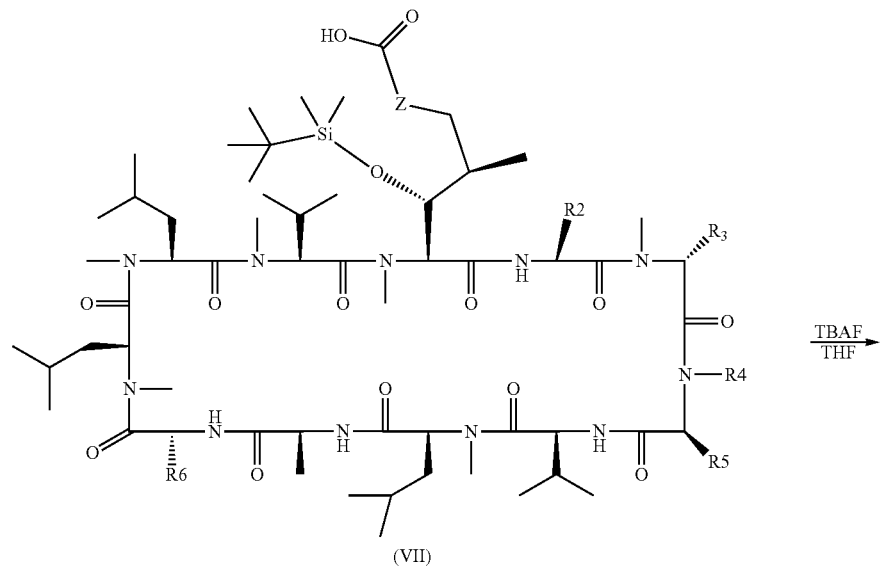

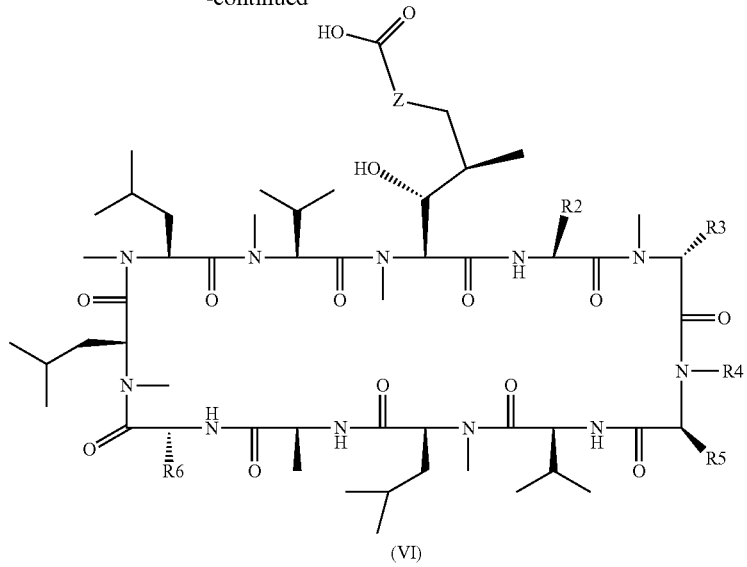
(VI)
Example I
Compounds of Formula I where X is NR$^8$, Y is CR$^9$R$^{10}$, each of R$^9$ and R$^{10}$ is hydrogen, and Z is (CH$_2$)$_m$, are prepared from intermediates of Formula IX by cyclization with pTSA in a solvent such as toluene at reflux. Compounds of Formula IX are prepared as described in WO2013181339.
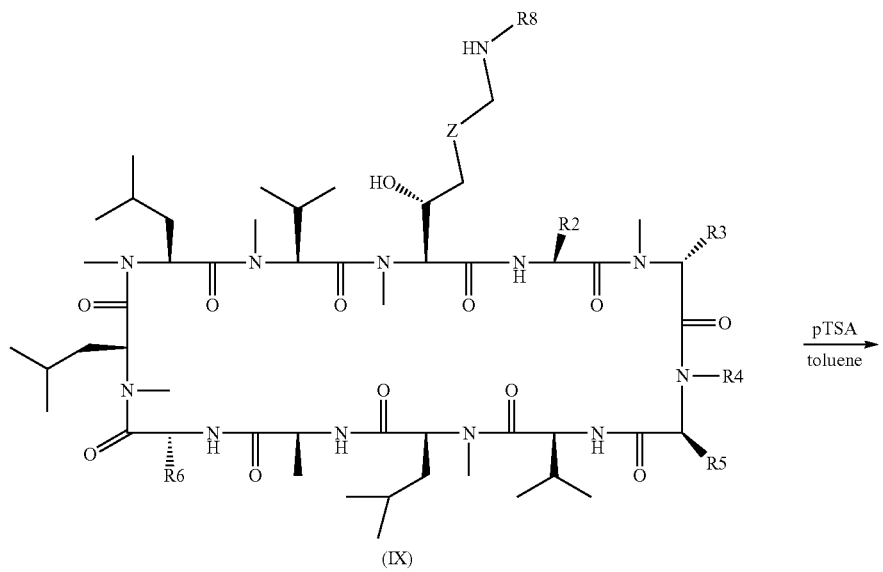
(IX)

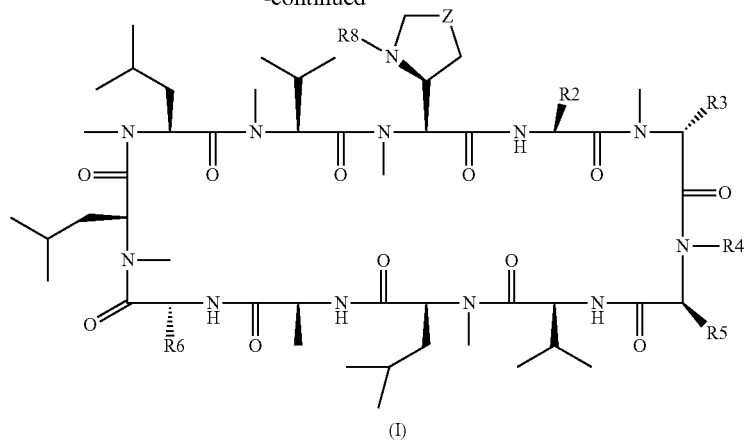
(I)
Example 1
Preparation of Compound 1 ([(2S)-2-(methyl-amino)-2-[(2R,3R)-3-methyltetrahydrofuran-2-yl] acetic acid][1] [(R)-ethyl-Sar][3] cyclosporin A) commencing with CsA according to Scheme 1
Scheme 1
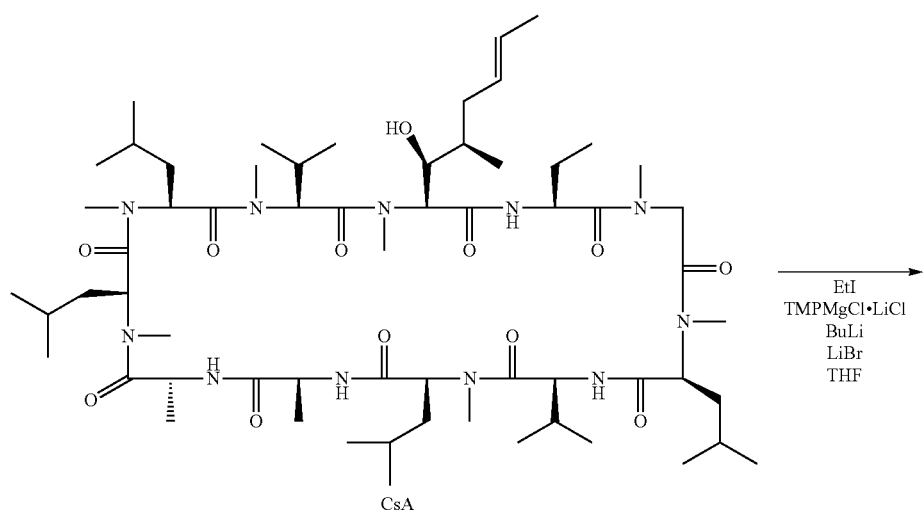

-continued
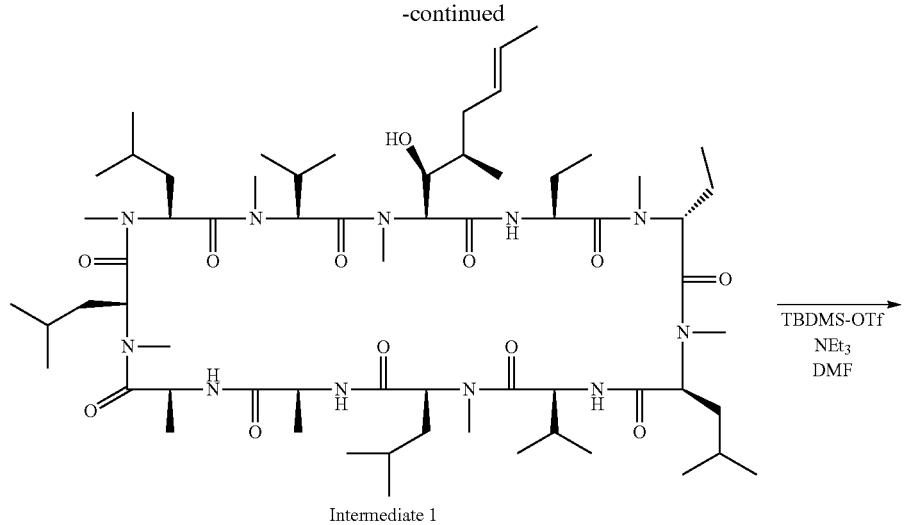
Intermediate 1
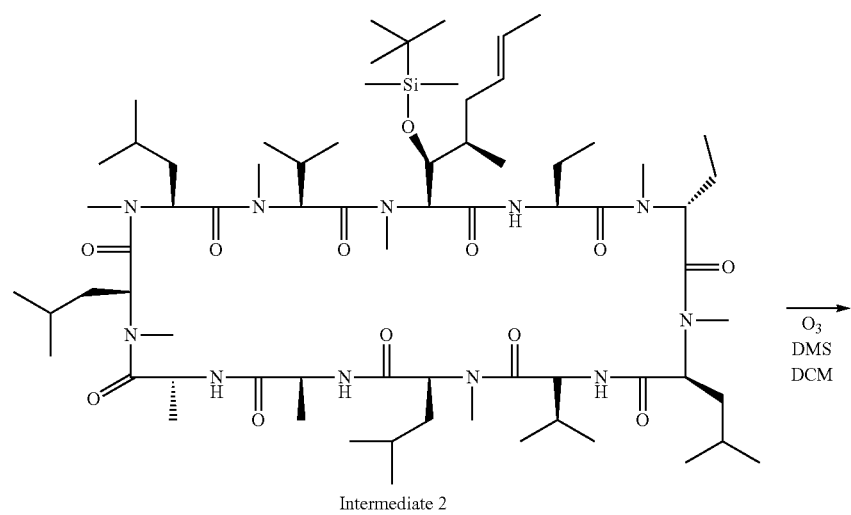
Intermediate 2
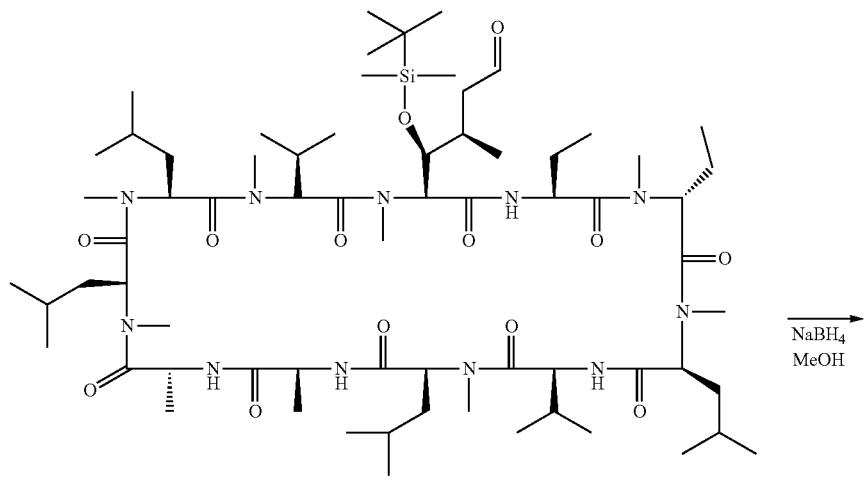
Intermediate 3

-continued
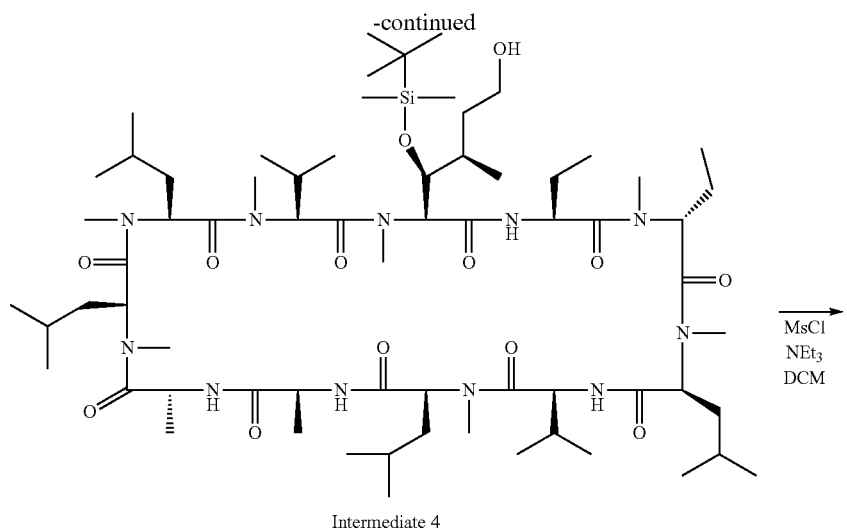
Intermediate 4
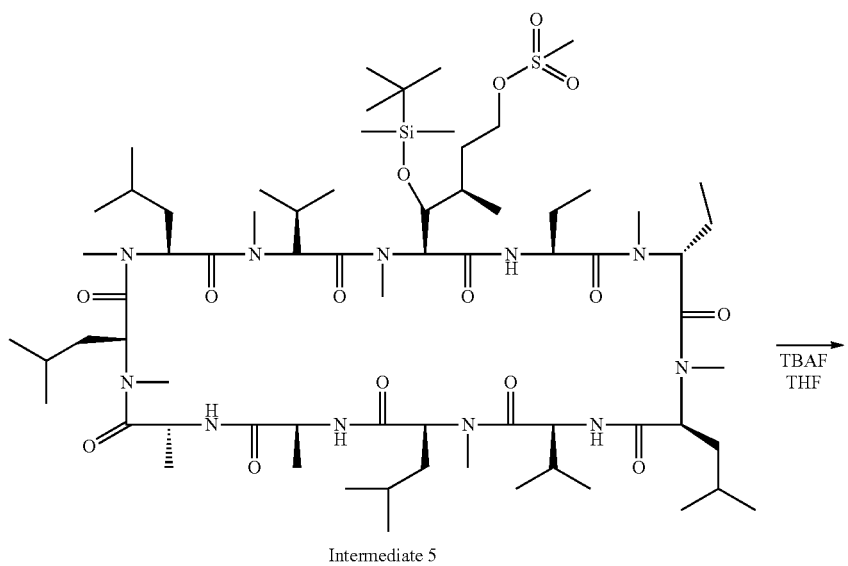
Intermediate 5
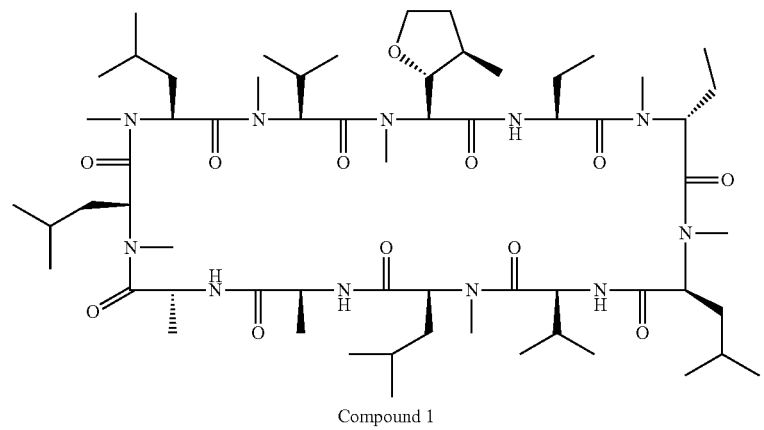
Compound 1

A. Preparation of Intermediate 1 from Cyclosporin A.

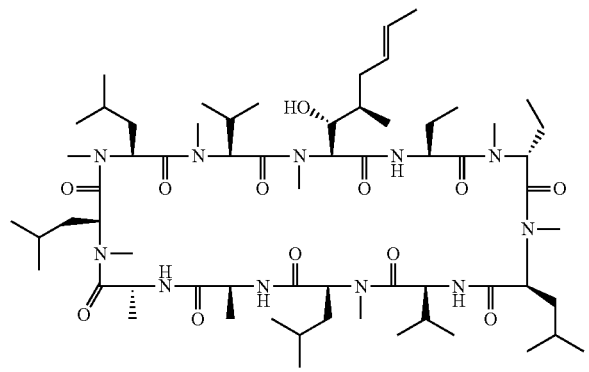

Intermediate 1

To a solution of cyclosporin A (5 g, 4.16 mmol) in THF (90 ml) was added lithium bromide (3.61 g, 41.60 mmol) and the solution was cooled to −55° C. under an atmosphere of nitrogen. A solution of tetramethylpiperidinemagnesium chloride lithium chloride complex in THF (1M, 29.12 ml, 29.12 mmol) was added dropwise and the solution stirred over 1 hour. Butyllithium solution in hexanes (1.6M, 15.6 ml, 24.96 mmol) was added dropwise and the solution stirred over 30 minutes. Ethyl iodide (6.69 ml, 83.20 mmol) was added and the reaction mixture warmed to room temperature and stirred over 18 hours. The reaction mixture was quenched with sat. aq. ammonium chloride (5 ml) then diluted with water (200 ml), ethyl acetate (200 ml) and MTBE (100 ml). The mixture was filtered over celite. The filtrate phases were separated and the aqueous extracted with MTBE (100 ml). The combined organics were washed with brine (50 ml), dried (MgSO$_4$), filtered and evaporated under reduced pressure to yield the crude product as a yellow solid. The crude product was purified by column chromatography using a solvent gradient of 50% MTBE/50% hexane to 90% MTBE/10% hexane to give [(R)-ethyl-Sar]³ cyclosporin A (Intermediate 1) as a white solid.

$^1$H NMR (CDCl$_3$, ppm) δ 7.16 (d, 1H, amide NH), 7.45 (d, 1H, amide NH), 7.67 (d, 1H, amide NH), 8.11 (d, 1H, amide NH).

B. Preparation of Intermediate 2 from Intermediate 1.

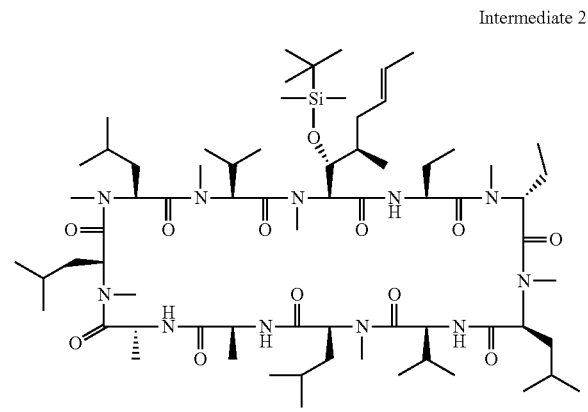 [SMILES: CC[C@@H]1C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N(C)[C@H]([C@H](O[Si](C)(C)C(C)(C)C)[C@H](C)CC=O)C(=O)N[C@H](CC)C(=O)N1C]

Intermediate 2

To a solution of [(R)-ethyl-Sar]³ cyclosporin A (Intermediate 1) (1.871 g, 1.52 mmol) in DMF (10 ml) under an atmosphere of nitrogen cooled to 0° C. was added triethylamine (2.12 ml, 15.20 mmol) followed by tert-butyldimethylsilyl trifluoromethanesulfonate (1.40 ml, 6.08 mmol) dropwise. The reaction mixture was warmed to room temperature and stirred over 18 hours. The reaction mixture was diluted with MTBE (100 ml) and washed with water (2×100 ml). The aqueous washings were extracted into MTBE (50 ml). The combined organics were dried (MgSO$_4$), filtered and evaporated under reduced pressure to yield the crude product as a yellow solid. The crude product was purified by column chromatography using a solvent gradient of 50% MTBE/50% hexane to 90% MTBE/10% hexane to give [(E,2S,3R,4R)-3-[tert-butyl(dimethyl)silyl]oxy-4-methyl-2-(methylamino)oct-6-enoic acid]$^1$ [(R)-ethyl-Sar]³ cyclosporin A (Intermediate 2) as a white solid.

$^1$H NMR (CDCl$_3$, ppm) δ 7.47 (m, 2H, amide NH), 7.94 (d, 1H, amide NH), 8.59 (d, 1H, amide NH).

C. Preparation of Intermediate 3 from Intermediate 2.

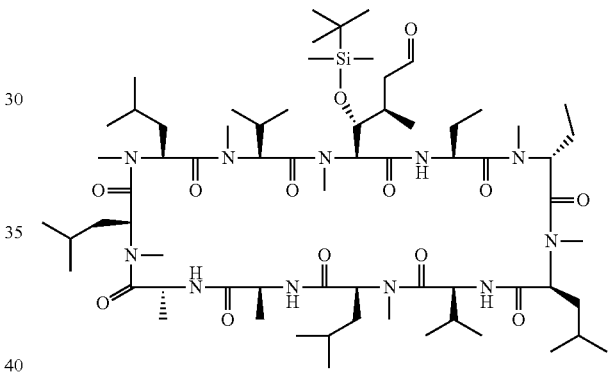

Intermediate 3

Ozone gas was bubbled through a solution of [(E,2S,3R,4R)-3-[tert-butyl(dimethyl)silyl]oxy-4-methyl-2-(methylamino)oct-6-enoic acid]$^1$[(R)-ethyl-Sar]³ cyclosporin A (Intermediate 2) (1.414 g, 1.05 mmol) in DCM (250 ml) cooled to −78° C. until the solution turned blue. Nitrogen was then bubbled through the solution until colourless again. Dimethylsulfide (0.309 ml, 4.20 mmol) was added and the solution allowed to warm to room temperature. The reaction mixture was washed with water then brine, dried (MgSO$_4$), filtered and evaporated under reduced pressure to yield the crude product as a white solid. The crude product was purified by column chromatography using a solvent gradient of 100% hexane to 30% acetone/70% hexane to give [(2S, 3R,4R)-3-[tert-butyl(dimethyl)silyl]oxy-4-methyl-2-(methylamino)-6-oxo-hexanoic acid]$^1$[(R)-ethyl-Sar]³ cyclosporin A (Intermediate 3) as a white solid.

$^1$H NMR (CDCl$_3$, ppm) δ 7.55 (m, 2H, amide NH), 7.91 (d, 1H, amide NH), 8.60 (d, 1H, amide NH), 9.61 (s, 1H, aldehyde CH).

D. Preparation of Intermediate 4 from Intermediate 3.

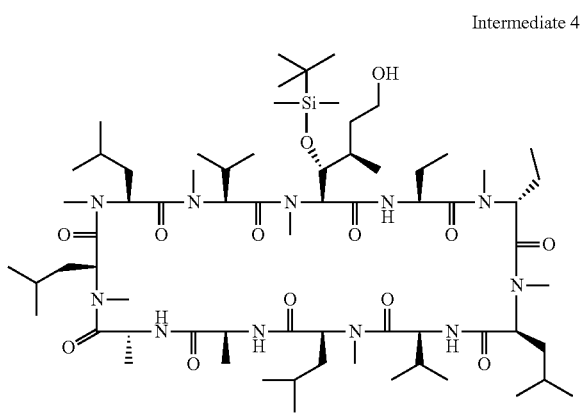 [SMILES: CC[C@@H]1C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N(C)[C@H]([C@H](O[Si](C)(C)C(C)(C)C)[C@H](C)CCO)C(=O)N[C@H](CC)C(=O)N1C]

Intermediate 4

To a solution of [(2S,3R,4R)-3-[tert-butyl(dimethyl)silyl]oxy-4-methyl-2-(methylamino)-6-oxo-hexanoic acid][1] [(R)-ethyl-Sar][3] cyclosporin A (Intermediate 3) (100 mg, 0.0752 mmol) in MeOH (4 ml) was added sodium borohydride (28 mg, 0.752 mmol), and the solution was stirred at room temperature over 18 hours. The reaction mixture was washed with 0.5M HCl then saturated aq. sodium bicarbonate, dried (MgSO$_4$), filtered and evaporated under reduced pressure to yield [(2S,3R,4R)-3-[tert-butyl(dimethyl)silyl]oxy-6-hydroxy-4-methyl-2-(methylamino)hexanoic acid][1] [(R)-ethyl-Sar][3] cyclosporin A (Intermediate 4) as a white solid.

$^1$H NMR (CDCl$_3$, ppm) δ 7.53 (d, 1H, amide NH), 7.71 (d, 1H, amide NH), 7.89 (d, 1H, amide NH), 8.47 (d, 1H, amide NH).

E. Preparation of Intermediate 5 from Intermediate 4.

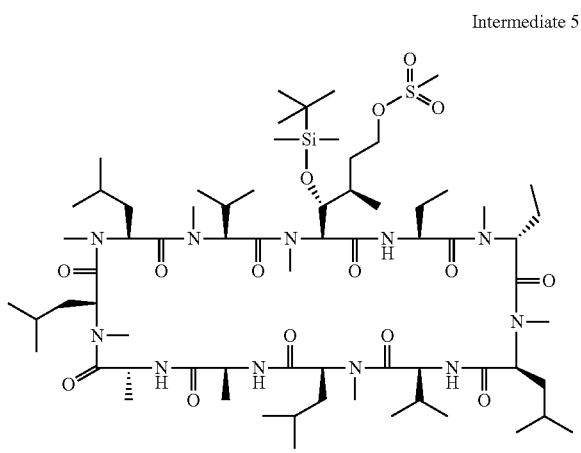 [SMILES: CC[C@@H]1C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N(C)[C@H]([C@H](O[Si](C)(C)C(C)(C)C)[C@H](C)CCOS(C)(=O)=O)C(=O)N[C@H](CC)C(=O)N1C]

Intermediate 5

To a solution of [(2S,3R,4R)-3-[tert-butyl(dimethyl)silyl]oxy-6-hydroxy-4-methyl-2-(methylamino)hexanoic acid][1] [(R)-ethyl-Sar][3] cyclosporin A (Intermediate 4) (98 mg, 0.0734 mmol) an DCM (2 ml) was added triethylamine (0.031 ml, 0.220 mmol) followed by methanesulfonyl chloride (0.0085 ml, 0.110 mmol) and the solution was stirred at room temperature over 3 hours. The reaction mixture was washed with water, dried (MgSO$_4$), filtered and evaporated under reduced pressure to yield [(2S,3R,4R)-3-[tert-butyl(dimethyl)silyl]oxy-4-methyl-2-(methylamino)-6-methyl-sulfonyloxy-hexanoic acid][1] [(R)-ethyl-Sar][3] cyclosporin A (Intermediate 5) as a white solid.

$^1$H NMR (CDCl$_3$, ppm) δ 7.54 (m, 2H, amide NH), 7.91 (d, 1H, amide NH), 8.57 (d, 1H, amide NH).

F. Preparation of Compound 1 from Intermediate 5.

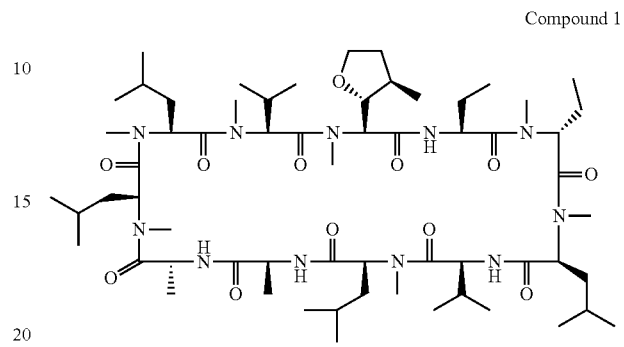

Compound 1

To a solution of [(2S,3R,4R)-3-[tert-butyl(dimethyl)silyl]oxy-4-methyl-2-(methylamino)-6-methylsulfonyloxy-hexanoic acid][1] [(R)-ethyl-Sar][3] cyclosporin A (Intermediate 5) (103 mg, 0.0729 mmol) in THF (3 ml) was added tetrabutylammonium fluoride solution in THF (1M, 0.364 ml, 0.364 mmol) and the solution was stirred at room temperature over 18 hours. The reaction mixture was evaporated under reduced pressure to a yellow gum. The gum was dissolved in DCM and washed with water then brine, dried (MgSO$_4$), filtered and evaporated under reduced pressure to yield the crude product as a yellow gum. The crude product was purified by preparative thin-layer chromatography eluting with 30% acetone/70% hexane to give Compound 1 as a white solid.

ES/MS: 1203.2 MH$^+$ $^1$H NMR (CDCl$_3$, ppm) δ 7.47 (d, 2H, amide NH), 8.10 (d, 1H, amide NH), 8.55 (d, 1H, amide NH).

Example 2

Preparation of Compound 2 ([(2S)-2-(methylamino)-2-[(2R,3R)-3-methyltetrahydrofuran-2-yl]acetic acid][1] [(R)-propyl-Sar][3] cyclosporin A) commencing with CsA

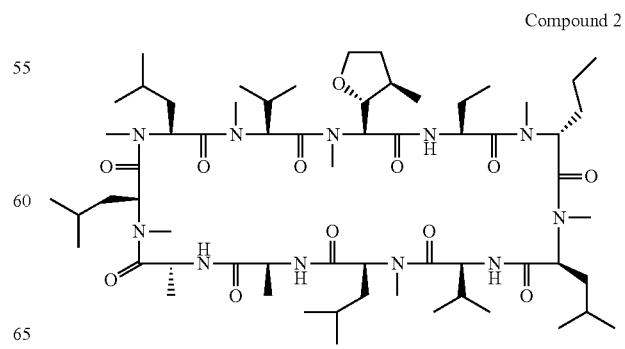

Compound 2

A. Preparation of Intermediate 2.1 from Cyclosporin A.

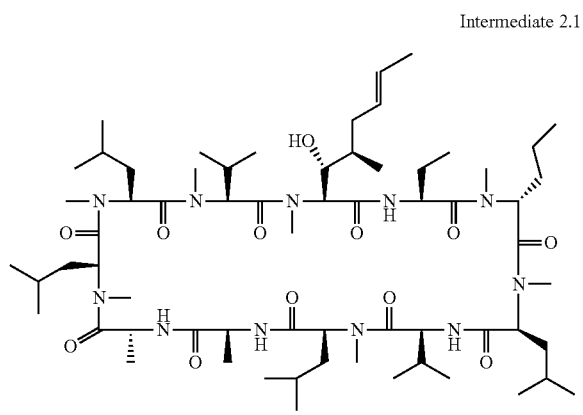 [SMILES: C/C=C/C[C@@H](C)[C@@H](O)[C@@H]1C(=O)N[C@H](CC)C(=O)N(C)[C@H](CCC)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

Intermediate 2.1

[(R)-propyl-Sar]³ cyclosporin A (Intermediate 2.1) was prepared by using propyl iodide instead of ethyl iodide in the above procedure for the conversion of CsA to Intermediate 1 shown in Scheme 1.

¹H NMR (CDCl₃, ppm) δ 7.16 (d, 1H, amide NH), 7.42 (d, 1H, amide NH), 7.67 (d, 1H, amide NH), 8.09 (d, 1H, amide NH).

B. Preparation of Intermediate 2.2 from Intermediate 2.1.

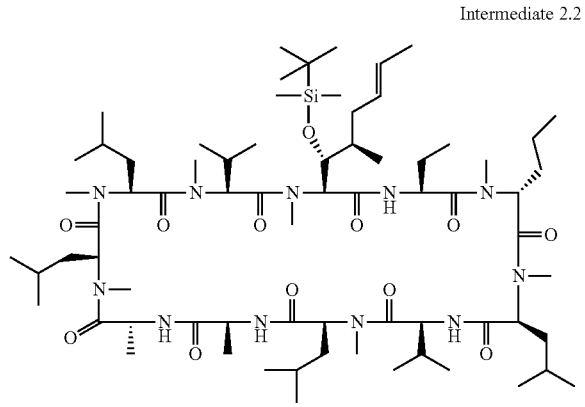 [SMILES: C/C=C/C[C@@H](C)[C@@H](O[Si](C)(C)C(C)(C)C)[C@@H]1C(=O)N[C@H](CC)C(=O)N(C)[C@H](CCC)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

Intermediate 2.2

Adapting the procedure described in Scheme 1, [(E,2S,3R,4R)-3-[tert-butyl(dimethyl)silyl]oxy-4-methyl-2-(methylamino)oct-6-enoic acid]¹ [(R)-propyl-Sar]³ cyclosporin A (Intermediate 2.2) was prepared from [(R)-propyl-Sar]³ cyclosporin A (Intermediate 2.1).

¹H NMR (CDCl₃, ppm) δ 7.50 (m, 2H, amide NH), 7.94 (d, 1H, amide NH), 8.58 (d, 1H, amide NH).

C. Preparation of Intermediate 2.3 from Intermediate 2.2.

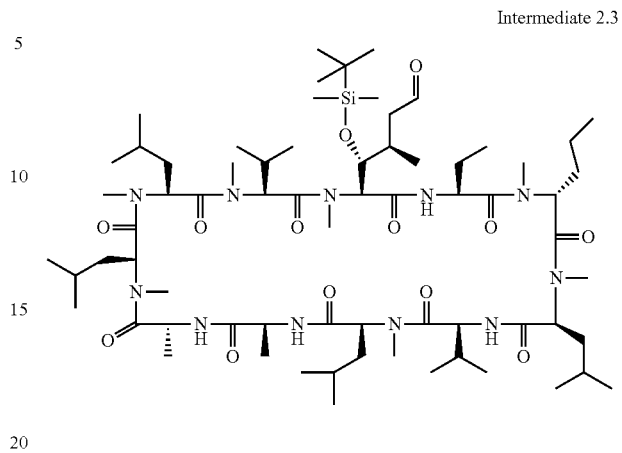

Intermediate 2.3

Adapting the procedure described in Scheme 1, [(2S,3R,4R)-3-[tert-butyl(dimethyl)silyl]oxy-4-methyl-2-(methylamino)-6-oxo-hexanoic acid]¹ [(R)-propyl-Sar]³ cyclosporin A (Intermediate 2.3) was prepared from [(E,2S,3R,4R)-3-[tert-butyl(dimethyl)silyl]oxy-4-methyl-2-(methylamino) oct-6-enoic acid]¹ [(R)-propyl-Sar]³ cyclosporin A (Intermediate 2.2).

¹H NMR (CDCl₃, ppm) δ 7.55 (m, 2H, amide NH), 7.91 (d, 1H, amide NH), 8.59 (d, 1H, amide NH), 9.61 (s, 1H, aldehyde CH).

D. Preparation of Intermediate 2.4 from Intermediate 2.3.

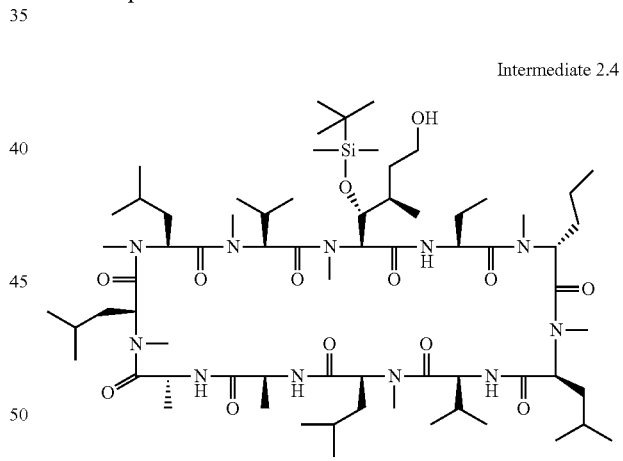

Intermediate 2.4

Adapting the procedure described in Scheme 1, [(2S,3R,4R)-3-[tert-butyl(dimethyl)silyl]oxy-6-hydroxy-4-methyl-2-(methylamino)hexanoic acid]¹ [(R)-propyl-Sar]³ cyclosporin A (Intermediate 2.4) was prepared from [(2S,3R,4R)-3-[tert-butyl(dimethyl)silyl]oxy-4-methyl-2-(methylamino)-6-oxo-hexanoic acid]¹ [(R)-propyl-Sar]³ cyclosporin A Intermediate 2.3.

¹H NMR (CDCl₃, ppm) δ 7.52 (d, 1H, amide NH), 7.69 (d, 1H, amide NH), 7.89 (d, 1H, amide NH), 8.45 (d, 1H, amide NH).

E. Preparation of Intermediate 2.5 from Intermediate 2.4.

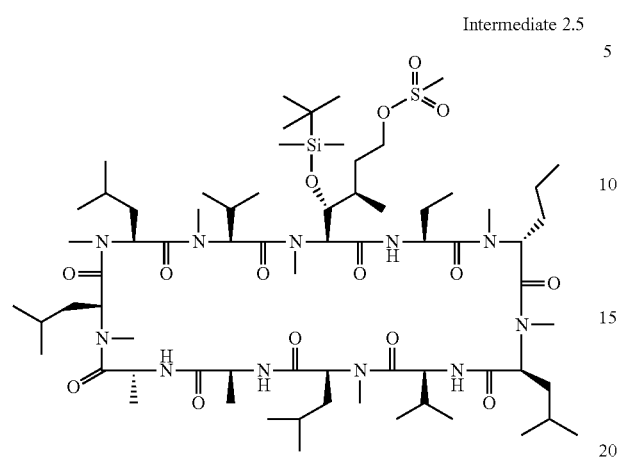

Intermediate 2.5

Adapting the procedure described in Scheme 1, [(2S,3R,4R)-3-[tert-butyl(dimethyl)silyl]oxy-4-methyl-2-(methylamino)-6-methylsulfonyloxy-hexanoic acid][1] [(R)-propyl-Sar][3] cyclosporin A (Intermediate 2.5) was prepared from [(2S,3R,4R)-3-[tert-butyl(dimethyl)silyl]oxy-6-hydroxy-4-methyl-2-(methylamino)hexanoic acid][1] [(R)-propyl-Sar][3] cyclosporin A (Intermediate 2.4).

$^1$H NMR (CDCl$_3$, ppm) δ 7.52 (m, 2H, amide NH), 7.87 (d, 1H, amide NH), 8.51 (d, 1H, amide NH).

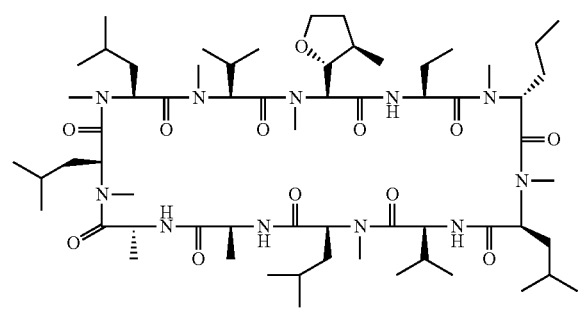

Intermediate 2.5

F. Preparation of Compound 2 from Intermediate 2.5.

Adapting the procedure described in Scheme 1, Compound 2 was prepared from [(2S,3R,4R)-3-[tert-butyl(dimethyl)silyl]oxy-4-methyl-2-(methylamino)-6-methylsulfonyloxy-hexanoic acid][1] [(R)-propyl-Sar][3] (cyclosporin A) (Intermediate 2.5).

ES/MS: 1216.70 MH$^+$

$^1$H NMR (CDCl$_3$, ppm) δ 7.45 (m, 2H, amide NH), 8.10 (d, 1H, amide NH), 8.53 (d, 1H, amide NH).

Example 3

Preparation of Compound 3 ([(2S)-2-(methylamino)-2-[(2R,3R)-3-methyltetrahydrofuran-2-yl]acetic acid][1] [(R)-methyl-Sar][3] cyclosporin A) from Intermediate 3.3

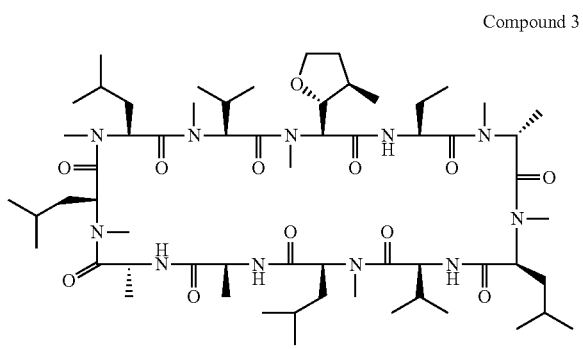 [SMILES: CC[C@H]1NC(=O)[C@@H]([C@@H]2OCC[C@H]2C)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Compound 3

Preparation of Intermediate 3.3.

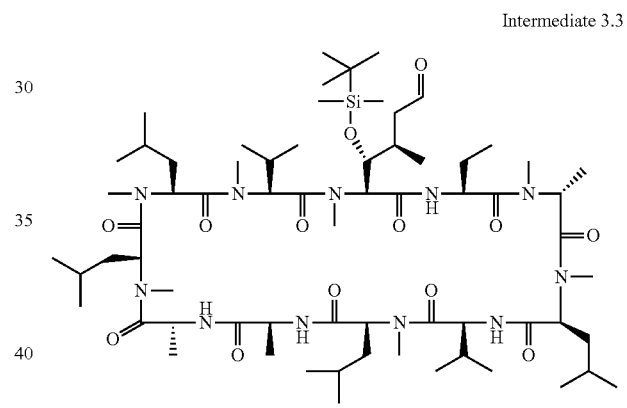

Intermediate 3.3

Intermediate 3.3 ([(2S,3R,4R)-3-[tert-butyl(dimethyl)silyl]oxy-4-methyl-2-(methylamino)-6-oxo-hexanoic acid][1] [(R)-methyl-Sar][3] cyclosporin A) was prepared as described previously in WO2013181339.

B. Preparation of Intermediate 3.4 from Intermediate 3.3.

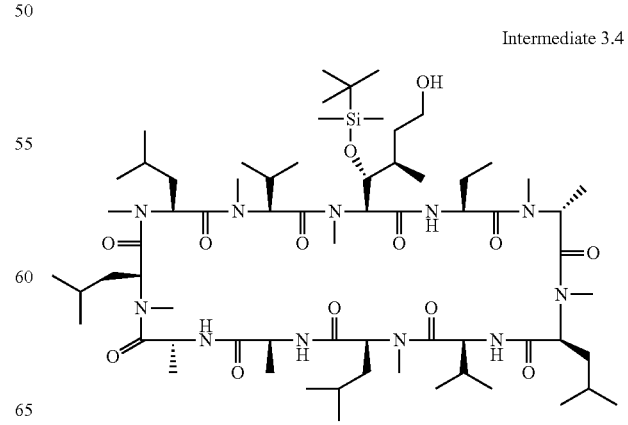

Intermediate 3.4

Adapting the procedure described in Scheme 1, [(2S,3R,4R)-3-[tert-butyl(dimethyl)silyl]oxy-6-hydroxy-4-methyl-2-(methylamino)hexanoic acid]¹ [(R)-methyl-Sar]³ cyclosporin A (Intermediate 3.4) was prepared from [(2S,3R,4R)-3-[tert-butyl(dimethyl)silyl]oxy-4-methyl-2-(methylamino)-6-oxo-hexanoic acid]¹ [(R)-methyl-Sar]³ cyclosporin A (Intermediate 3.3).

¹H NMR (CDCl₃, ppm) δ 7.57 (d, 1H, amide NH), 7.81 (d, 1H, amide NH), 7.93 (d, 1H, amide NH), 8.40 (d, 1H, amide NH).

C. Preparation of Intermediate 3.5 from Intermediate 3.4.

Intermediate 3.5

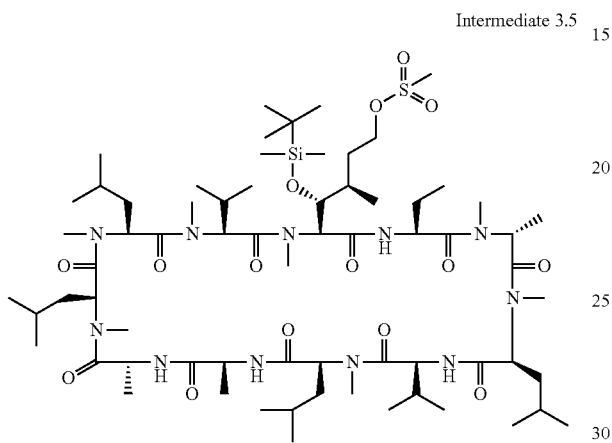

Adapting the procedure described in Scheme 1, [(2S,3R,4R)-3-[tert-butyl(dimethyl)silyl]oxy-4-methyl-2-(methylamino)-6-methylsulfonyloxy-hexanoic acid]¹ [(R)-methyl-Sar]³ cyclosporin A (Intermediate 3.5) was prepared from [(2S,3R,4R)-3-[tert-butyl(dimethyl)silyl]oxy-6-hydroxy-4-methyl-2-(methylamino)hexanoic acid]¹ [(R)-methyl-Sar]³ cyclosporin A (Intermediate 3.4).

¹H NMR (CDCl₃, ppm) δ 7.60 (m, 2H, amide NH), 7.92 (d, 1H, amide NH), 8.46 (d, 1H, amide NH).

D. Preparation of Compound 3 from Intermediate 3.5.

Compound 3

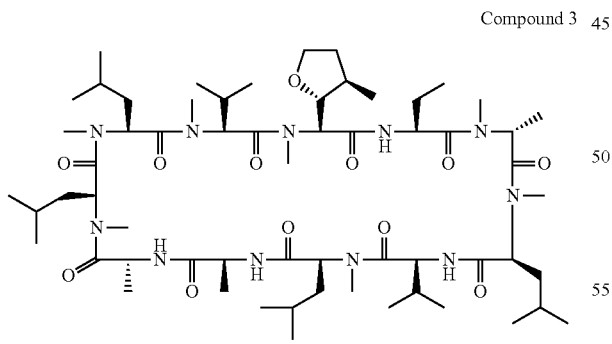

Adapting the procedure described in Scheme 1, Compound 3 was prepared from [(2S,3R,4R)-3-[tert-butyl(dimethyl)silyl]oxy-4-methyl-2-(methylamino)-6-methylsulfonyloxy-hexanoic acid]¹ [(R)-methyl-Sar]³ cyclosporin A (Intermediate 3.5).

ES/MS: 1188.6 MH⁺

¹H NMR (CDCl₃, ppm) δ 7.49 (d, 1H, amide NH), 7.57 (d, 1H, amide NH), 8.11 (d, 1H, amide NH), 8.45 (d, 1H, amide NH).

Example 4

Preparation of Compound 4 ([(2S)-2-(methylamino)-2-[(2R,3R)-3-methyltetrahydrofuran-2-yl] acetic acid]¹ cyclosporin A) from Intermediate 4.3

Compound 4

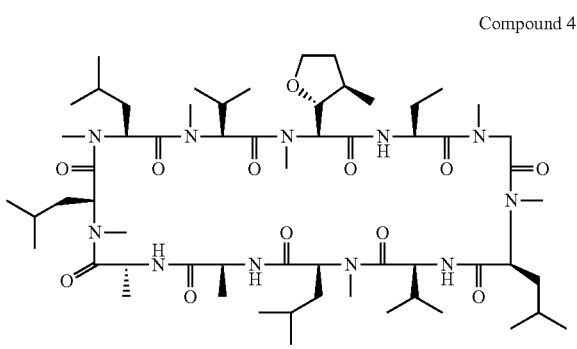 [SMILES: CC[C@H]1NC(=O)[C@@H]([C@@H]2OCC[C@H]2C)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)CN(C)C1=O]

Preparation of Intermediate 4.3.

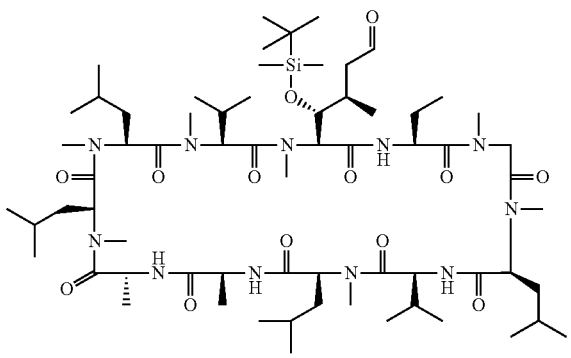 [SMILES: CC[C@H]1NC(=O)[C@@H]([C@H](O[Si](C)(C)C(C)(C)C)[C@H](C)CC=O)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)CN(C)C1=O]

Intermediate 4.3 ([(2S,3R,4R)-3-[tert-butyl(dimethyl)silyl]oxy-4-methyl-2-(methylamino)-6-oxo-hexanoic acid]¹ cyclosporin A) was prepared as described previously in WO2013181339.

ES/MS: 1304.92 MH⁺

¹H NMR (CDCl₃, ppm) δ 7.53 (d, 1H, amide NH), 7.62 (d, 1H, amide NH), 7.87 (d, 1H, amide NH), 8.41 (d, 1H, amide NH), 9.64 (s, 1H, aldehyde CH).

B. Preparation of Intermediate 4.4 from Intermediate 4.3.

Intermediate 4.4

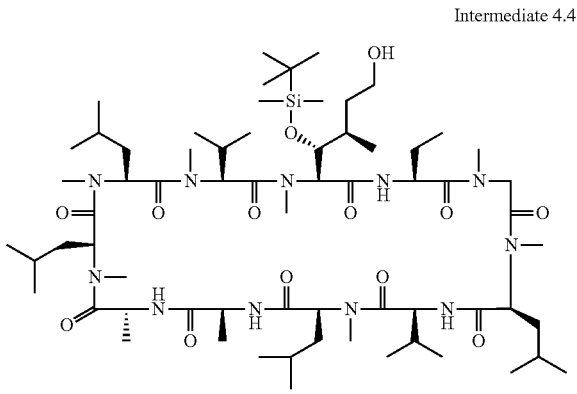 [SMILES: CC[C@H]1NC(=O)[C@@H]([C@H](O[Si](C)(C)C(C)(C)C)[C@H](C)CCO)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)CN(C)C1=O]

Adapting the procedure described in Scheme 1, [(2S,3R,4R)-3-[tert-butyl(dimethyl)silyl]oxy-6-hydroxy-4-methyl-2-(methylamino)hexanoic acid]¹ cyclosporin A (Intermediate 4.4) was prepared from [(2S,3R,4R)-3-[tert-butyl(dimethyl)silyl]oxy-4-methyl-2-(methylamino)-6-oxo-hexanoic acid]¹ cyclosporin A (Intermediate 4.3).

ES/MS: 1306.82

¹H NMR (CDCl$_3$, ppm) δ 7.57 (d, 1H, amide NH), 7.79 (d, 1H, amide NH), 7.91 (d, 1H, amide NH), 8.39 (d, 1H, amide NH).

C. Preparation of Intermediate 4.5 from Intermediate 4.4.

Intermediate 4.5

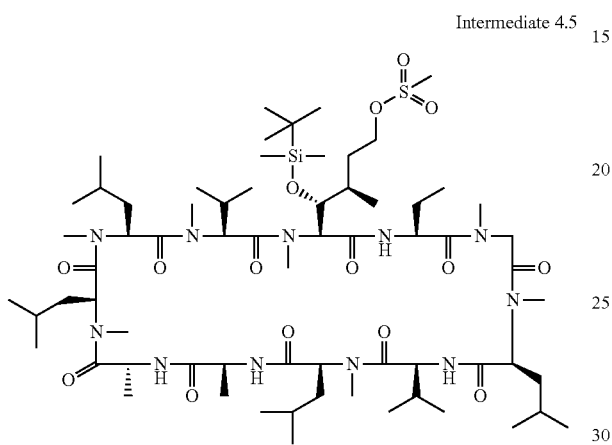

Adapting the procedure described in Scheme 1, [(2S,3R,4R)-3-[tert-butyl(dimethyl)silyl]oxy-4-methyl-2-(methylamino)-6-methylsulfonyloxy-hexanoic acid]¹ cyclosporin A (Intermediate 4.5 was prepared from [(2S,3R,4R)-3-[tert-butyl(dimethyl)silyl]oxy-6-hydroxy-4-methyl-2-(methylamino)hexanoic acid]¹ cyclosporin A (Intermediate 4.4)

ES/MS: 1384.91

¹H NMR (CDCl$_3$, ppm) δ 7.57 (d, 1H, amide NH), 7.61 (d, 1H, amide NH), 7.89 (d, 1H, amide NH), 8.45 (d, 1H, amide NH).

D. Preparation of Compound 4 from Intermediate 4.5.

Compound 4

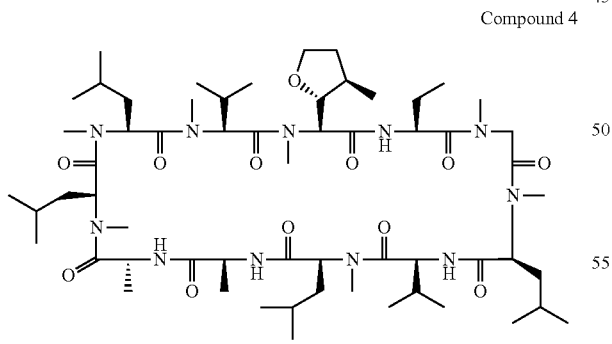

Adapting the procedure described in Scheme 1, Compound 4 was prepared from [(2S,3R,4R)-3-[tert-butyl(dimethyl)silyl]oxy-4-methyl-2-(methylamino)-6-methylsulfonyloxy-hexanoic acid]¹ cyclosporin A (Intermediate 4.5).

ES/MS: 1174.45 MH⁺

¹H NMR (CDCl$_3$, ppm) δ 7.49 (d, 1H, amide NH), 7.57 (d, 1H, amide NH), 8.11 (d, 1H, amide NH), 8.45 (d, 1H, amide NH).

Example 5

Preparation of Compound 5 ([(2S)-2-(methylamino)-2-[(2R,3R)-3-methyltetrahydrofuran-2-yl] acetic acid]¹ [(S)-difluoromethyl-Sar]³ cyclosporin A) from CSA Compound 5

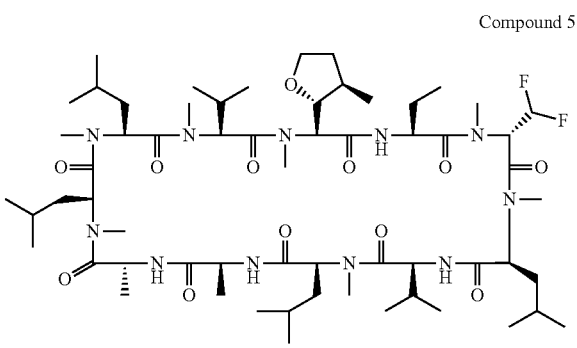 [SMILES: CC[C@H]1NC(=O)[C@@H]([C@@H]2OCC[C@H]2C)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C(F)F)N(C)C1=O]

A. Preparation of Intermediate 5.1 from Cyclosporin A.

Intermediate 5.1

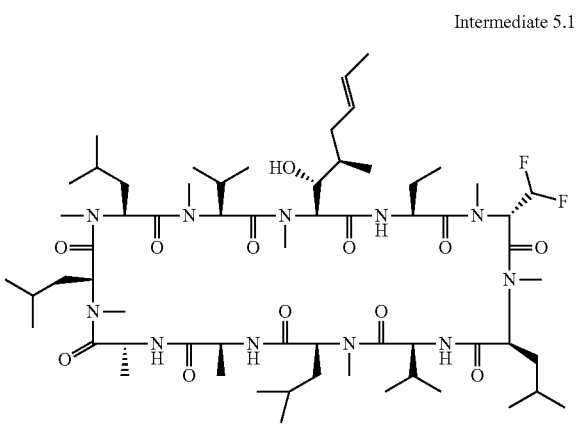 [SMILES: C/C=C/C[C@@H](C)[C@@H](O)[C@@H]1C(=O)N[C@H](CC)C(=O)N(C)[C@H](C(F)F)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

[(S)-difluoromethyl-Sar]³ cyclosporin A (Intermediate 5.1) was prepared from cyclosporin A, replacing propyl iodide with difluoromethyl iodide, in the above procedure shown in Scheme 1.

ES/MS: 1252.66 MH⁺

¹H NMR (CDCl$_3$, ppm) δ 6.25 (td, 1H, CHF$_2$), 7.19 (d, 1H, amide NH), 7.24 (d, 1H, amide NH), 7.75 (d, 1H, amide NH), 8.27 (d, 1H, amide NH).

B. Preparation of Intermediate 5.2 from Intermediate 5.1.

Intermediate 5.2

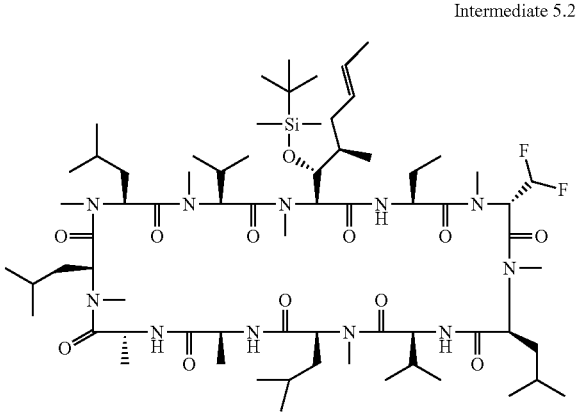 [SMILES: C/C=C/C[C@@H](C)[C@@H](O[Si](C)(C)C(C)(C)C)[C@@H]1C(=O)N[C@H](CC)C(=O)N(C)[C@H](C(F)F)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

[(E,2S,3R,4R)-3-[tert-butyl(dimethyl)silyl]oxy-4-methyl-2-(methylamino)oct-6-enoic acid]¹ [(S)-difluoromethyl-Sar]³ cyclosporin A Intermediate 5.2 was prepared from Intermediate 5.1 by adapting the procedure described in Scheme 1.

¹H NMR (CDCl₃, ppm) δ 6.33 (td, 1H, CHF₂), 7.29 (d, 1H, amide NH), 7.47 (d, 1H, amide NH), 7.91 (d, 1H, amide NH), 8.54 (d, 1H, amide NH).

C. Preparation of Intermediate 5.3 from Intermediate 5.2.

Intermediate 5.3

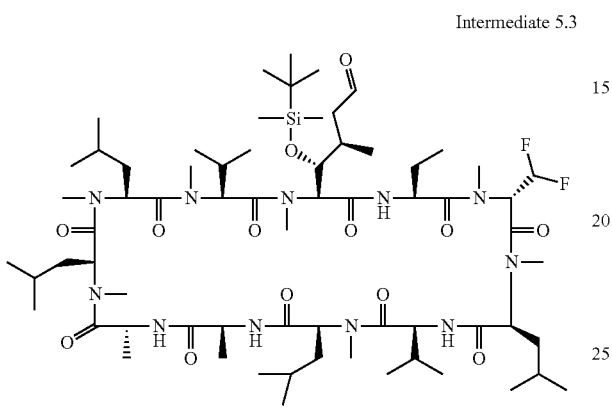

[(2S,3R,4R)-3-[tert-butyl(dimethyl)silyl]oxy-4-methyl-2-(methylamino)-6-oxo-hexanoic acid]¹ [(S)-difluoromethyl-Sar]³ cyclosporin A Intermediate 5.3 was prepared from Intermediate 5.2 by adapting the procedure described in Scheme 1.

¹H NMR (CDCl₃, ppm) δ 6.22 (td, 1H, CHF₂), 7.28 (d, 1H, amide NH), 7.54 (d, 1H, amide NH), 7.86 (d, 1H, amide NH), 8.53 (d, 1H, amide NH), 9.59 (s, 1H, aldehyde CH).

D. Preparation of Compound 5 from Intermediate 5.3.

Compound 5

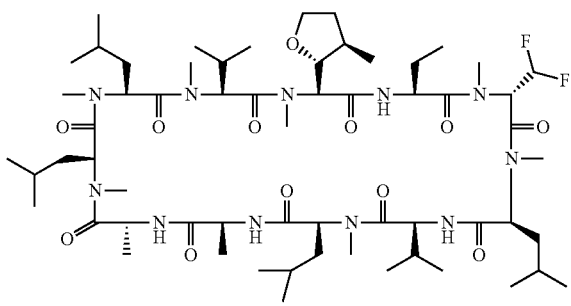

[(2S)-2-(methylamino)-2-[(2R,3R)-3-methyltetrahydrofuran-2-yl]acetic acid]¹ [(S)-difluoromethyl-Sar]³ Cyclosporin A) Compound 5 was prepared from [(2S,3R,4R)-3-[tert-butyl(dimethyl)silyl]oxy-4-methyl-2-(methylamino)-6-oxo-hexanoic acid]¹ [(S)-difluoromethyl-Sar]³ cyclosporin A (Intermediate 5.3) by the reaction with morpholine in DCM in the presence of sodium triacetoxyborohydride.

ES/MS: 1224.54 MH⁺

¹H NMR (CDCl₃, ppm) δ 6.3 (m, 1H, —CHF₂), δ 7.20 (d, 1H, amide NH), 7.57 (d, 1H, amide NH), 8.11 (d, 1H, amide NH), 8.51 (d, 1H, amide NH).

Example 6

Preparation of Compound 6 [(2S)-2-(methylamino)-2-[(2R,3R)-3-methyltetrahydrofuran-2-yl]acetic acid]¹ [(R)-methyl-Sar]³ cyclosporin D) commencing with Cyclosporin D Compound 6

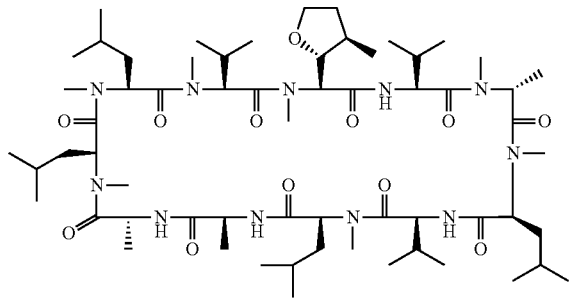

A. Preparation of Intermediate 6.1 from Cyclosporin D.

Intermediate 6.1

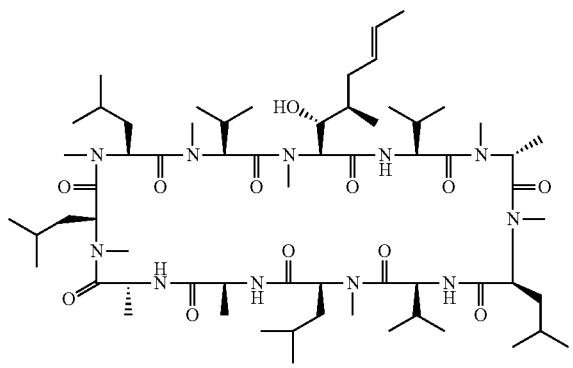

[(R)-methyl-Sar]³ cyclosporin D (Intermediate 6.1) was prepared by substituting cyclosporin A with cyclosporin D, and propyl iodide with methyl iodide, in the above procedure shown in Scheme 1.

ES/MS: 1230.9 MH⁺

¹H NMR (CDCl₃, ppm) δ 7.13 (d, 1H, amide NH), 7.59 (d, 1H, amide NH), 7.66 (d, 1H, amide NH), 7.93 (d, 1H, amide NH).

B. Preparation of Intermediate 6.2 from Intermediate 6.1.

Intermediate 6.2

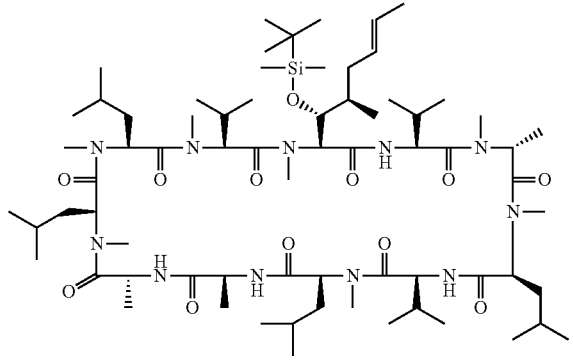

Adapting the procedure shown in Scheme 1, [(E,2S,3R,4R)-3-[tert-butyl(dimethyl)silyl]oxy-4-methyl-2-(methylamino)oct-6-enoic acid]¹ [(R)-methyl-Sar]³ cyclosporin D (Intermediate 6.2) was prepared from [(R)-methyl-Sar]³ cyclosporin D (Intermediate 6.1).

¹H NMR (CDCl₃, ppm) δ 7.49 (d, 1H, amide NH), 7.79 (d, 1H, amide NH), 7.96 (d, 1H, amide NH), 8.52 (d, 1H, amide NH).

C. Preparation of Intermediate 6.3 from Intermediate 6.2.

Intermediate 6.3

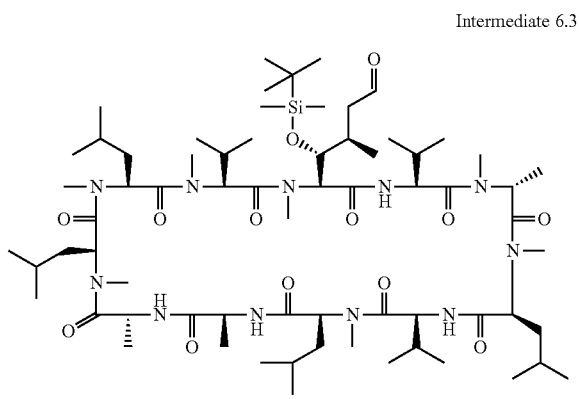 [SMILES: CC(C)C[C@@H]1C(=O)N(C)[C@H](CC(C)C)C(=O)N(C)[C@H](C(C)C)C(=O)N(C)[C@H]([C@H](O[Si](C)(C)C(C)(C)C)[C@H](C)CC=O)C(=O)N[C@H](C(C)C)C(=O)N(C)[C@H](C)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N1C]

Adapting the procedure shown in Scheme 1, [(2S,3R,4R)-3-[tert-butyl(dimethyl)silyl]oxy-4-methyl-2-(methylamino)-6-oxo-hexanoic acid]¹ [(R)-methyl-Sar]³ cyclosporin D (Intermediate 6.3) was prepared from [(E,2S,3R,4R)-3-[tert-butyl(dimethyl)silyl]oxy-4-methyl-2-(methylamino)oct-6-enoic acid]¹ [(R)-methyl-Sar]³ cyclosporin D (Intermediate 6.2).

¹H NMR (CDCl₃, ppm) δ 7.59 (d, 1H, amide NH), 7.81 (d, 1H, amide NH), 7.91 (d, 1H, amide NH), 8.53 (d, 1H, amide NH), 9.61 (s, 1H, aldehyde CH).

D. Preparation of Intermediate 6.4 from Intermediate 6.3.

Intermediate 6.4

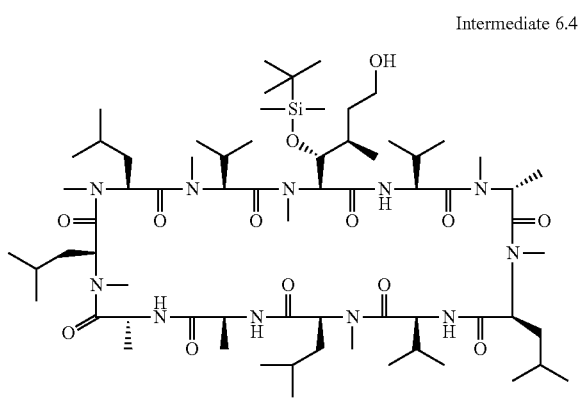 [SMILES: CC(C)C[C@@H]1C(=O)N(C)[C@H](CC(C)C)C(=O)N(C)[C@H](C(C)C)C(=O)N(C)[C@H]([C@H](O[Si](C)(C)C(C)(C)C)[C@H](C)CCO)C(=O)N[C@H](C(C)C)C(=O)N(C)[C@H](C)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N1C]

Adapting the procedure shown in Scheme 1, [(2S,3R,4R)-3-[tert-butyl(dimethyl)silyl]oxy-6-hydroxy-4-methyl-2-(methylamino)hexanoic acid]¹ [(R)-methyl-Sar]³ cyclosporin D (Intermediate 6.4) was prepared from [(2S,3R,4R)-3-[tert-butyl(dimethyl)silyl]oxy-4-methyl-2-(methylamino)-6-oxo-hexanoic acid]¹ [(R)-methyl-Sar]³ cyclosporin D (Intermediate 6.3).

¹H NMR (CDCl₃, ppm) δ 7.59 (d, 1H, amide NH), 7.96 (d, 1H, amide NH), 8.01 (d, 1H, amide NH), 8.45 (d, 1H, amide NH).

E. Preparation of Intermediate 6.5 from Intermediate 6.4.

Intermediate 6.5

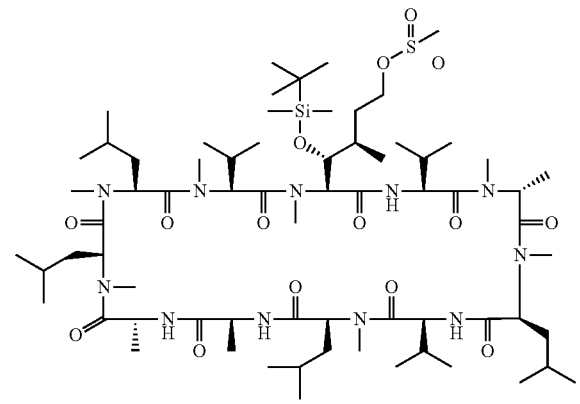

Adapting the procedure shown in Scheme 1, [(2S,3R,4R)-3-[tert-butyl(dimethyl)silyl]oxy-4-methyl-2-(methylamino)-6-methylsulfonyloxy-hexanoic acid]¹ [(R)-methyl-Sar]³ cyclosporin D (Intermediate 6.5) was prepared from [(2S,3R,4R)-3-[tert-butyl(dimethyl)silyl]oxy-6-hydroxy-4-methyl-2-(methylamino)hexanoic acid]¹ [(R)-methyl-Sar]³ cyclosporin D (Intermediate 6.4).

¹H NMR (CDCl₃, ppm) δ 7.59 (d, 1H, amide NH), 7.79 (d, 1H, amide NH), 7.90 (d, 1H, amide NH), 8.52 (d, 1H, amide NH).

E. Preparation of Compound 6 from Intermediate 6.5.

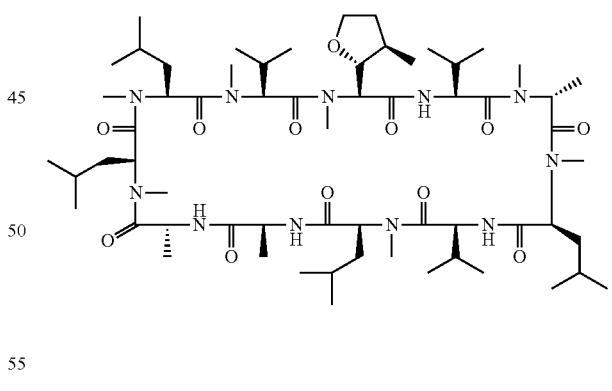

Adapting the procedure shown in Scheme 1, Compound 6 was prepared from [(2S,3R,4R)-3-[tert-butyl(dimethyl)silyl]oxy-4-methyl-2-(methylamino)-6-methylsulfonyloxy-hexanoic acid]¹ [(R)-methyl-Sar]³ (cyclosporin D) (Intermediate 6.5).

ES/MS: 1202.84 MH⁺

¹H NMR (CDCl₃, ppm) δ 7.50 (d, 1H, amide NH), 7.72 (d, 1H, amide NH), 8.11 (d, 1H, amide NH), 8.52 (d, 1H, amide NH).

Example 7

Preparation of Compound 7 ([(2S)-2-(methyl-amino)-2-[(2R,3R)-3-methyltetrahydrofuran-2-yl]acetic acid]¹ cyclosporin D) commencing with Cyclosporin D Compound 7

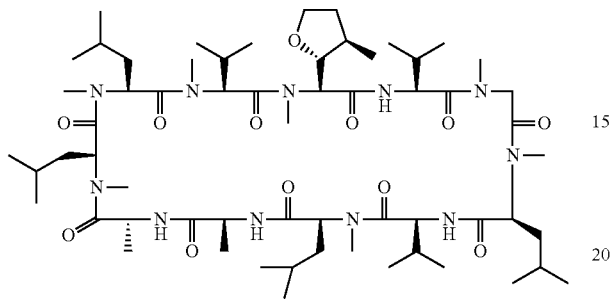

A. Preparation of Intermediate 7.2 from Cyclosporin D.

Intermediate 7.2

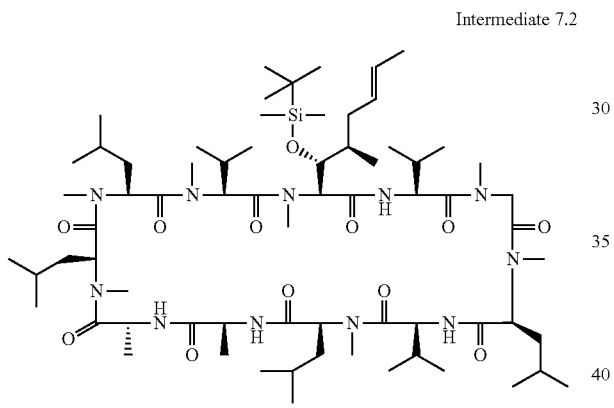

Adapting the procedure shown in Scheme 1, [(E,2S,3R,4R)-3-[tert-butyl(dimethyl)silyl]oxy-4-methyl-2-(methylamino)oct-6-enoic acid]¹ cyclosporin D (Intermediate 7.2) was prepared from cyclosporin D.

$^1$H NMR (CDCl$_3$, ppm) δ 7.45 (d, 1H, amide NH), 7.79 (d, 1H, amide NH), 7.89 (d, 1H, amide NH), 8.41 (d, 1H, amide NH).

B. Preparation of Intermediate 7.3 from Intermediate 7.2.

Intermediate 7.3

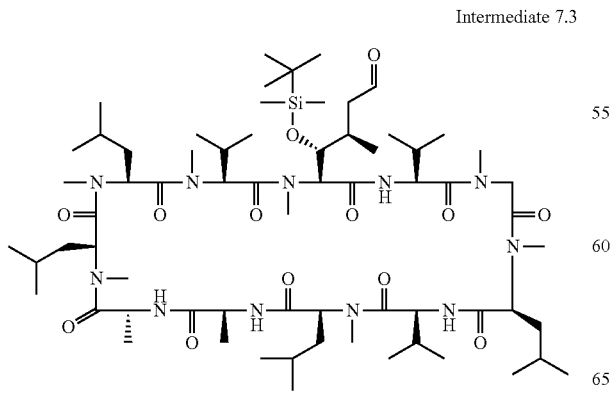

Adapting the procedure shown in Scheme 1, [(2S,3R,4R)-3-[tert-butyl(dimethyl)silyl]oxy-4-methyl-2-(methylamino)-6-oxo-hexanoic acid]¹ cyclosporin D (Intermediate 7.3) was prepared from [(E,2S,3R,4R)-3-[tert-butyl(dimethyl)silyl]oxy-4-methyl-2-(methylamino)oct-6-enoic acid]¹ cyclosporin D (Intermediate 7.2).

$^1$H NMR (CDCl$_3$, ppm) δ 7.56 (d, 1H, amide NH), 7.78 (d, 1H, amide NH), 7.87 (d, 1H, amide NH), 8.49 (d, 1H, amide NH), 9.60 (s, 1H, aldehyde CH).

C. Preparation of Intermediate 7.4 from Intermediate 7.3.

Intermediate 7.4

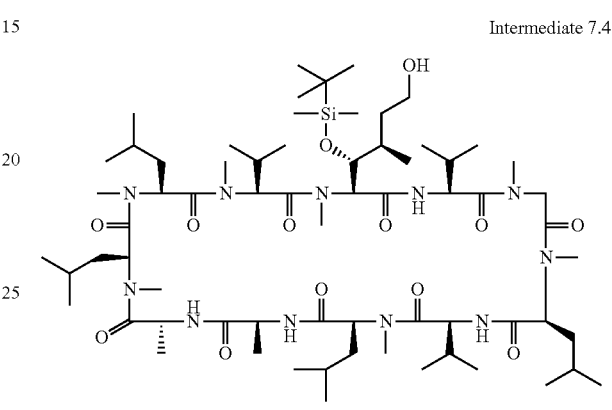

Adapting the procedure shown in Scheme 1, [(2S,3R,4R)-3-[tert-butyl(dimethyl)silyl]oxy-6-hydroxy-4-methyl-2-(methylamino)hexanoic acid]¹ cyclosporin D (Intermediate 7.4) was prepared from [(2S,3R,4R)-3-[tert-butyl(dimethyl)silyl]oxy-4-methyl-2-(methylamino)-6-oxo-hexanoic acid]¹ cyclosporin D (Intermediate 7.3).

$^1$H NMR (CDCl$_3$, ppm) δ 7.59 (d, 1H, amide NH), 7.94 (d, 1H, amide NH), 8.00 (d, 1H, amide NH), 8.41 (d, 1H, amide NH).

D. Preparation of Intermediate 7.5 from Intermediate 7.4.

Intermediate 7.5

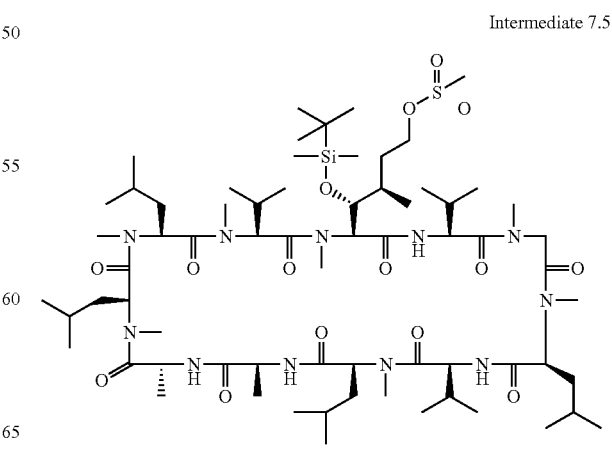

Adapting the procedure shown in Scheme 1, [(2S,3R,4R)-3-[tert-butyl(dimethyl)silyl]oxy-4-methyl-2-(methylamino)-6-methylsulfonyloxy-hexanoic acid][1] cyclosporin D (Intermediate 7.5) was prepared from [(2S,3R,4R)-3-[tert-butyl(dimethyl)silyl]oxy-6-hydroxy-4-methyl-2-(methylamino)hexanoic acid][1] cyclosporin D (Intermediate 7.4).

$^1$H NMR (CDCl$_3$, ppm) δ 7.59 (d, 1H, amide NH), 7.80 (d, 1H, amide NH), 7.90 (d, 1H, amide NH), 8.51 (d, 1H, amide NH).

E. Preparation of Compound 7 from Intermediate 7.5.

Compound 7

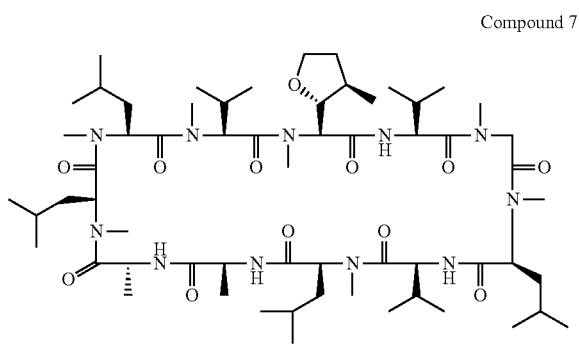

Adapting the procedure shown in Scheme 1, Compound 7 was prepared from [(2S,3R,4R)-3-[tert-butyl(dimethyl)silyl]oxy-4-methyl-2-(methylamino)-6-methylsulfonyloxy-hexanoic acid][1] (cyclosporin D) (Intermediate 7.5).

ES/MS: 1188.82 MH$^+$

$^1$H NMR (CDCl$_3$, ppm) δ 7.49 (d, 1H, amide NH), 7.72 (d, 1H, amide NH), 8.10 (d, 1H, amide NH), 8.50 (d, 1H, amide NH).

Example 8

Preparation of Compound 8 ([(2S)-2-(methylamino)-2-[(2R,3R)-3-methyltetrahydrofuran-2-yl]acetic acid][1] cyclosporin C) commencing with Cyclosporin C Compound 8

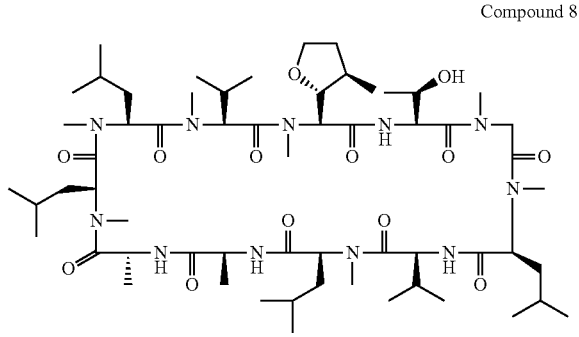 [SMILES: CC(C)C[C@@H]1C(=O)N(C)[C@H](CC(C)C)C(=O)N(C)[C@H](C(C)C)C(=O)N(C)[C@H]([C@@H]2OCC[C@H]2C)C(=O)N[C@H]([C@@H](C)O)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N1C]

A. Preparation of Intermediate 8.1 from Cyclosporin C.

Intermediate 8.1

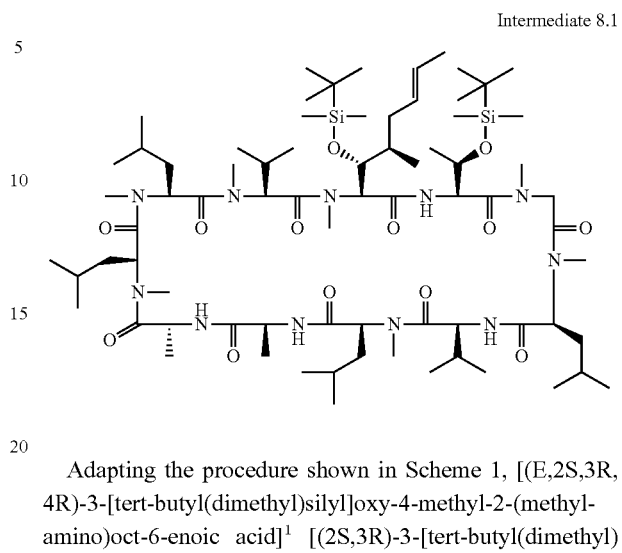

Adapting the procedure shown in Scheme 1, [(E,2S,3R,4R)-3-[tert-butyl(dimethyl)silyl]oxy-4-methyl-2-(methylamino)oct-6-enoic acid][1] [(2S,3R)-3-[tert-butyl(dimethyl)silyl]oxy-2-(amino)butanoic acid][2] cyclosporin C (Intermediate 8.1) was prepared from cyclosporin C.

$^1$H NMR (CDCl$_3$, ppm) δ 7.11 (d, 1H, amide NH), 7.39 (d, 1H, amide NH), 7.49 (d, 1H, amide NH), 7.73 (d, 1H, amide NH).

B. Preparation of Intermediate 8.2 from Intermediate 8.1.

Intermediate 8.2

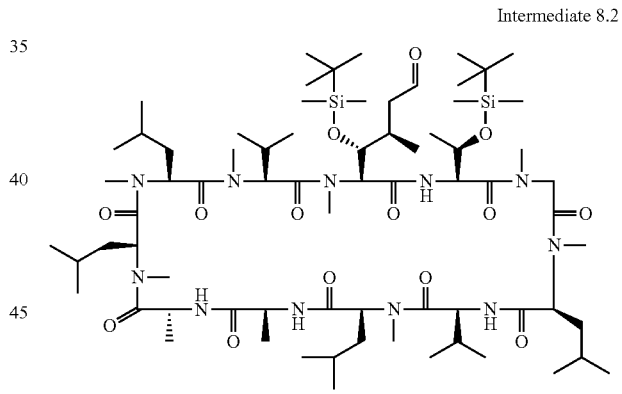

Adapting the procedure shown in Scheme 1, [(2S,3R,4R)-3-[tert-butyl(dimethyl)silyl]oxy-4-methyl-2-(methylamino)-6-oxo-hexanoic acid][1] [(2S,3R)-3-[tert-butyl(dimethyl)silyl]oxy-2-(amino)butanoic acid][2] cyclosporin C (Intermediate 8.2) was prepared from [(E,2S,3R,4R)-3-[tert-butyl(dimethyl)silyl]oxy-4-methyl-2-(methylamino)oct-6-enoic acid][1] [(2S,3R)-3-[tert-butyl(dimethyl)silyl]oxy-2-(amino)butanoic acid][2] cyclosporin C (Intermediate 8.1).

$^1$H NMR (CDCl$_3$, ppm) δ 7.54 (d, 1H, amide NH), 7.79 (d, 1H, amide NH), 7.99 (d, 1H, amide NH), 8.24 (d, 1H, amide NH), 9.71 (s, 1H, aldehyde CH).

C. Preparation of Intermediate 8.3 from Intermediate 8.2.

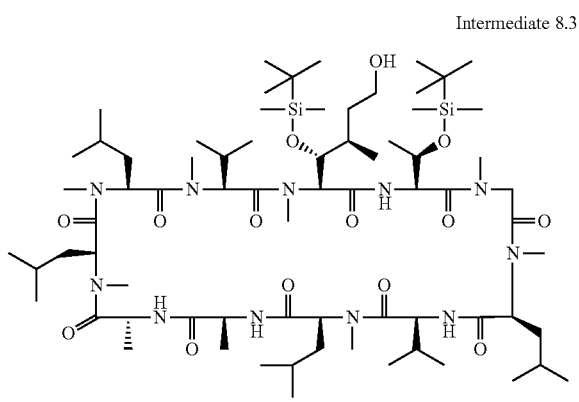 [SMILES: CC(C)C[C@@H]1C(=O)N(C)[C@H](CC(C)C)C(=O)N(C)[C@H](C(C)C)C(=O)N(C)[C@H]([C@H](O[Si](C)(C)C(C)(C)C)[C@H](C)CCO)C(=O)N[C@H]([C@@H](C)O[Si](C)(C)C(C)(C)C)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N1C]

Intermediate 8.3

Adapting the procedure shown in Scheme 1, [(2S,3R,4R)-3-[tert-butyl(dimethyl)silyl]oxy-6-hydroxy-4-methyl-2-(methylamino)hexanoic acid][1] [(2S,3R)-3-[tert-butyl(dimethyl)silyl]oxy-2-(amino)butanoic acid][2] cyclosporin C (Intermediate 8.3) was prepared from [(2S,3R,4R)-3-[tert-butyl(dimethyl)silyl]oxy-4-methyl-2-(methylamino)-6-oxo-hexanoic acid][1] [(2S,3R)-3-[tert-butyl(dimethyl)silyl]oxy-2-(amino)butanoic acid][2] cyclosporin C (Intermediate 8.2).

$^1$H NMR (CDCl$_3$, ppm) δ 7.60 (d, 1H, amide NH), 7.99 (d, 1H, amide NH), 8.09 (d, 1H, amide NH), 8.25 (d, 1H, amide NH).

D. Preparation of Intermediate 8.4 from Intermediate 8.3.

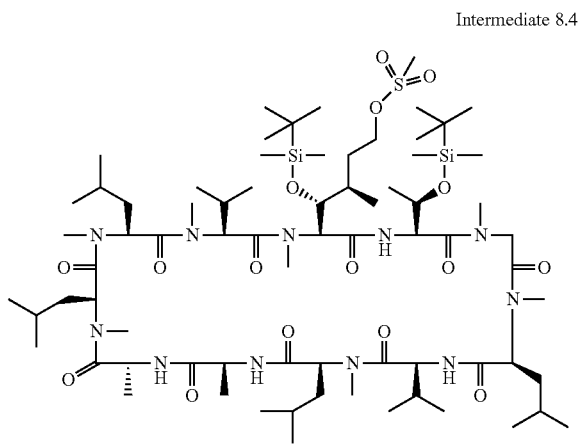 [SMILES: CC(C)C[C@@H]1C(=O)N(C)[C@H](CC(C)C)C(=O)N(C)[C@H](C(C)C)C(=O)N(C)[C@H]([C@H](O[Si](C)(C)C(C)(C)C)[C@H](C)CCOS(C)(=O)=O)C(=O)N[C@H]([C@@H](C)O[Si](C)(C)C(C)(C)C)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N1C]

Intermediate 8.4

Adapting the procedure shown in Scheme 1, [(2S,3R,4R)-3-[tert-butyl(dimethyl)silyl]oxy-4-methyl-2-(methylamino)-6-methylsulfonyloxy-hexanoic acid][1] [(2S,3R)-3-[tert-butyl(dimethyl)silyl]oxy-2-(amino)butanoic acid][2] cyclosporin C (Intermediate 8.4) was prepared from [(2S,3R,4R)-3-[tert-butyl(dimethyl)silyl]oxy-6-hydroxy-4-methyl-2-(methylamino)hexanoic acid][1] [(2S,3R)-3-[tert-butyl(dimethyl)silyl]oxy-2-(amino)butanoic acid][2] cyclosporin C (Intermediate 8.3)

$^1$H NMR (CDCl$_3$, ppm) δ 7.59 (d, 1H, amide NH), 7.93 (d, 1H, amide NH), 7.99 (d, 1H, amide NH), 8.28 (d, 1H, amide NH).

E. Preparation of Compound 8 from Intermediate 8.4.

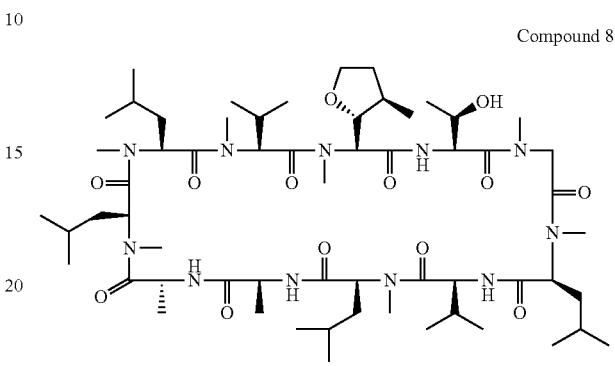

Compound 8

Adapting the procedure shown in Scheme 1, Compound 8 was prepared from [(2S,3R,4R)-3-[tert-butyl(dimethyl)silyl]oxy-4-methyl-2-(methylamino)-6-methylsulfonyloxy-hexanoic acid][1] [(2S,3R)-3-[tert-butyl(dimethyl)silyl]oxy-2-(amino)butanoic acid][2] cyclosporin C (Intermediate 8.4).

ES/MS: 1190.71 MH$^+$ $^1$H NMR (CDCl$_3$, ppm) δ 7.31 (d, 1H, amide NH), 7.4 (d, 1H, amide NH), 7.88 (d, 1H, amide NH), 8.61 (d, 1H, amide NH).

Example 9

Preparation of Compound 9 ([(2S)-2-(methyl-amino)-2-[(2R,3R)-3-methyltetrahydrofuran-2-yl]acetic acid][1] cyclosporin B) commencing with Cyclosporin B

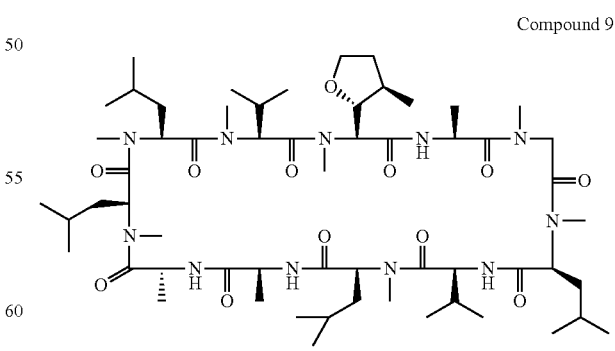

Compound 9

Compound 9 was prepared in a similar manner to Compound 1 except that the chemistry was carried out without using protecting groups such as TBDMS as shown in Scheme 2 below.

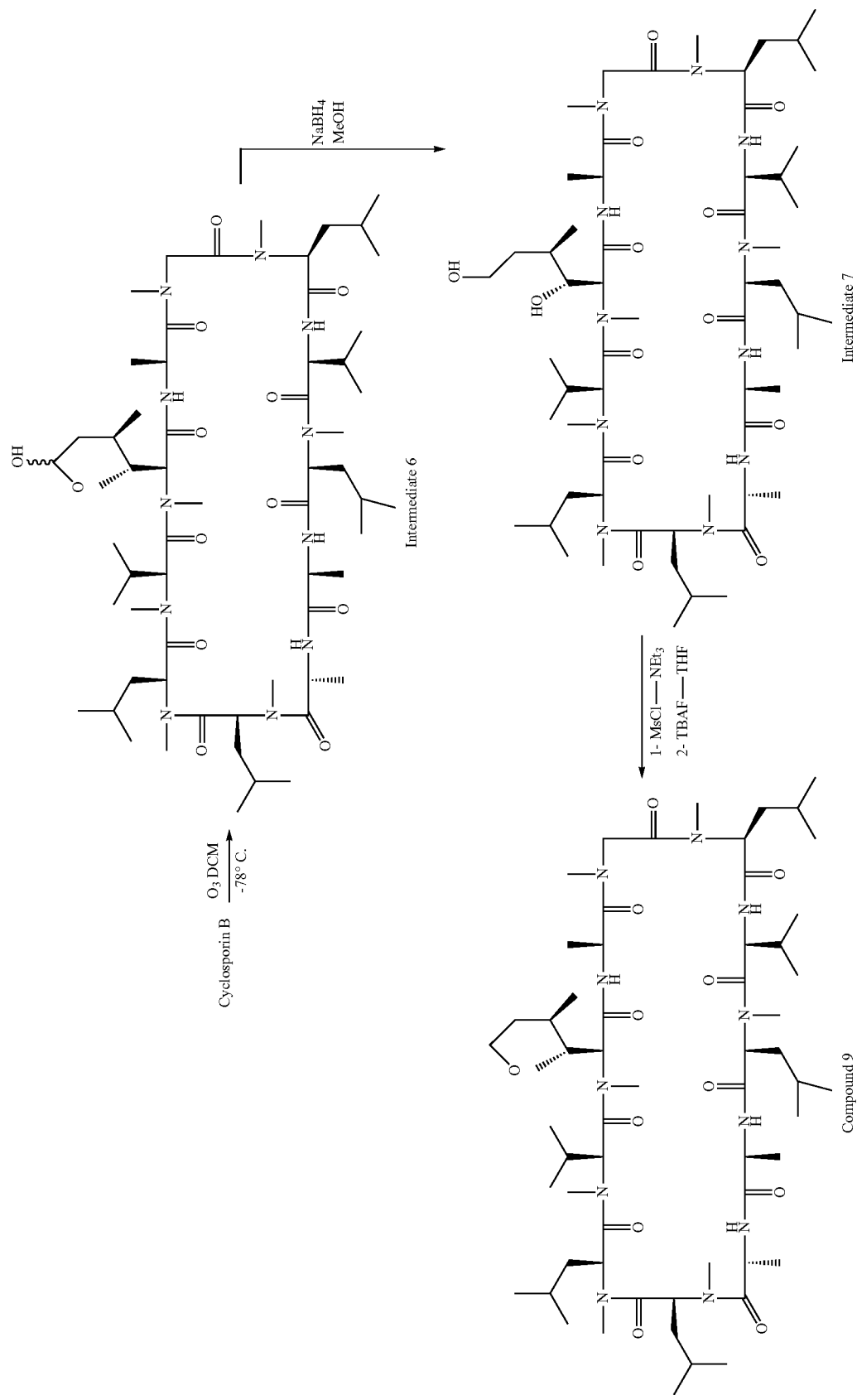

A. Preparation of Intermediate 6 from Cyclosporin B

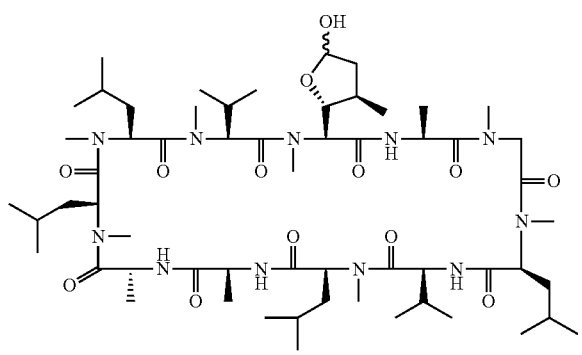

A solution of cyclosporin B (90 mg, 0.075 mmol) was dissolved in CH$_2$Cl$_2$ (15 ml) and added to a 3-neck flask equipped with inlet (for nitrogen/ozone addition) and outlet connected to a Dreschler bottle containing 2M KI solution. The reaction mixture was cooled to −78° C. in a solid CO$_2$/acetone bath, under a nitrogen atmosphere. When the temperature of the reaction vessel had established, the nitrogen was removed and ozone bubbled through the reaction mixture until it became a pale blue color. The ozone supply was removed and nitrogen bubbled through the reaction mixture until the blue color had gone, then dimethylsulphide (0.35 ml) was added, and the reaction mixture warmed to room temperature. After 5 hours, the reaction mixture was washed with H$_2$O, dried (Na$_2$SO$_4$), filtered and evaporated under reduced pressure to yield [(2S)-2-[(2R,3R)-5-hydroxy-3-methyl-tetrahydrofuran-2-yl]-2-(methylamino)acetic acid][1] cyclosporin B (Intermediate 6) as a white solid.

ES/MS: 1176.74 MH$^+$.

B. Preparation of Intermediate 7 from Intermediate 6.

Intermediate 7

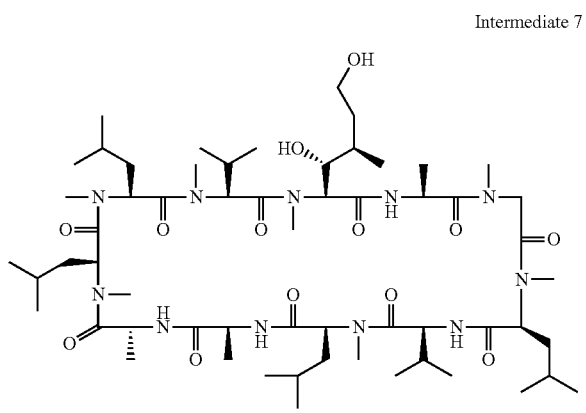 [SMILES: CC(C)C[C@@H]1C(=O)N(C)[C@H](CC(C)C)C(=O)N(C)[C@H](C(C)C)C(=O)N(C)[C@H]([C@H](O)[C@H](C)CCO)C(=O)N[C@H](C)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N1C]

[(2S)-2-[(2R,3R)-5-Hydroxy-3-methyl-tetrahydrofuran-2-yl]-2-(methylamino)acetic acid][1] cyclosporin B (Intermediate 6) (82 mg, 0.07 mmol) was dissolved in methanol (2 ml) then treated with sodium borohydride (27 mg, 0.7 mmol) under a nitrogen atmosphere. After 4.5 hours, the reaction mixture was concentrated, the residue was taken up in dichloromethane, washed with HCl 0.5M, a saturated solution of NaHCO$_3$, then brine. The solution was dried (Na$_2$SO$_4$), filtered and evaporated under reduced pressure to yield [(2S,3R,4R)-2-(methylamino)-3,6-dihydroxy-4-methyl-hexanoic acid][1] cyclosporin B (Intermediate 7) as a white solid.

ES/MS: 1178.7 MH$^+$
$^1$H NMR (CDCl$_3$, ppm) δ 7.29 (d, 1H, amide NH), 7.45 (d, 1H, amide NH), 7.82 (d, 1H, amide NH), 8.21 (d, 1H, amide NH).

C. Preparation of Compound 9 from Intermediate 7.

Compound 9

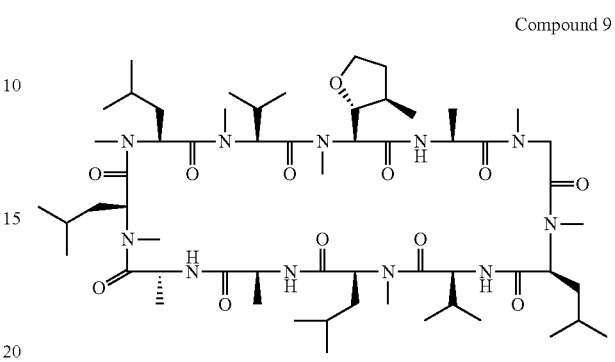

[(2S,3R,4R)-2-(Methylamino)-3,6-dihydroxy-4-methyl-hexanoic acid][1] cyclosporin B (Intermediate 7; 75 mg, 0.063 mmol) was dissolved in dry dichloromethane (1 mL) then treated with triethylamine (36 uL, 0.252 mmol). A dichloromethane solution (1 mL) containing mesyl chloride (7.5 μL, 0.096 mmol) was added and the reaction mixture was stirred at room temperature under a nitrogen atmosphere for 4.5 hours. Water was added and the organic phase was dried (Na$_2$SO$_4$), filtered and evaporated under reduced pressure. The residue was dissolved in tetrahydrofuran (2 mL) then treated with a 1M solution of TBAF (300 uL, 0.3 mmol). The reaction mixture was left to stand at room temperature over 18 hours. The reaction mixture was concentrated, the residue was taken up in ethyl acetate and washed with water. The organic phase was dried (Na$_2$SO$_4$), filtered and evaporated under reduced pressure to yield the crude product. Purification by PTLC using as solvent 45% acetone/55% hexane gave Compound 9 ([(2S)-2-(methylamino)-2-[(2R,3R)-3-methyltetrahydrofuran-2-yl]acetic acid][1] cyclosporin B) as a white solid.

ES/MS: 1160.83 MH$^+$
$^1$H NMR (CDCl$_3$, ppm) δ 7.42 (d, 1H, amide NH), 7.47 (d, 1H, amide NH), 8.12 (d, 1H, amide NH), 8.39 (d, 1H, amide NH).

Example 10

Preparation of Compound 10 ([(2S)-2-(methylamino)-2-[(2R,3R)-3-methyltetrahydrofuran-2-yl] acetic acid][1] [(R)-methyl-Sar][3] cyclosporin B) from Compound 9

Compound 10

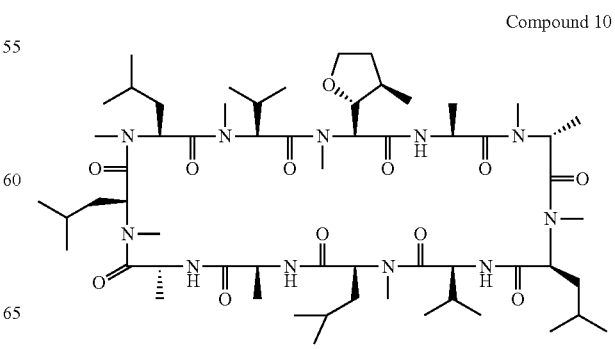

Compound 10 was prepared from Compound 9 using the procedure described in Scheme 1 to prepare Intermediate 1. The anion formed was quenched with methyl iodide to give Compound 10 as shown in Scheme 3.
Scheme 3
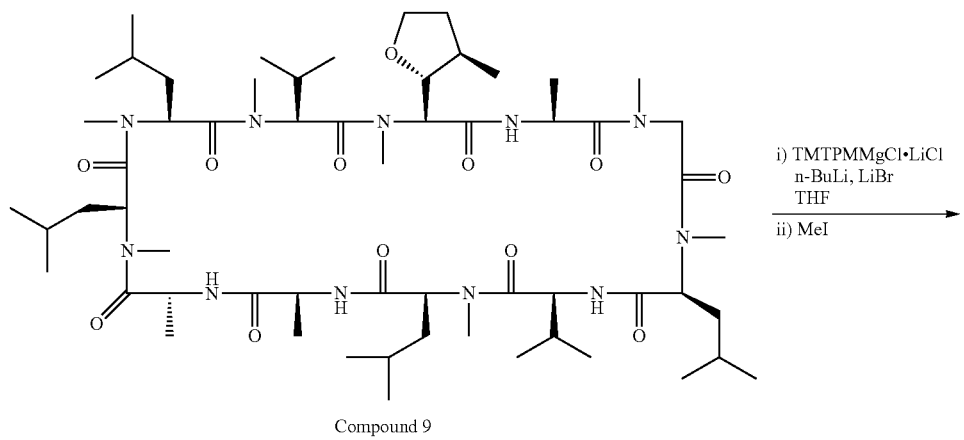
i) TMTPMMgCl·LiCl
   n-BuLi, LiBr
   THF
ii) MeI
Compound 9
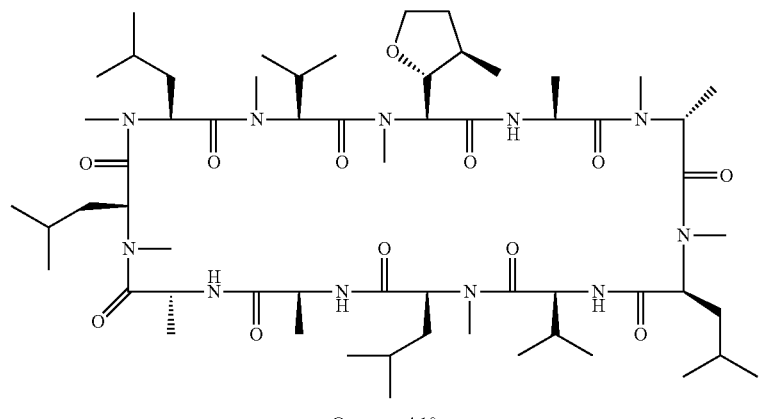
Compound 10

ES/MS: 1174.77 MH+

$^1$H NMR (CDCl$_3$, ppm) δ 7.43 (d, 1H, amide NH), 7.47 (d, 1H, amide NH), 8.14 (d, 1H, amide NH), 8.43 (d, 1H, amide NH).

Example 11

Preparation of Compound 11 ([(2S)-2-(methyl-amino)-2-[(2R,3R)-3-methyltetrahydrofuran-2-yl] acetic acid]$^1$ [(R)-methyl-Sar]$^3$ cyclosporin C) from Compound 8

Compound 11

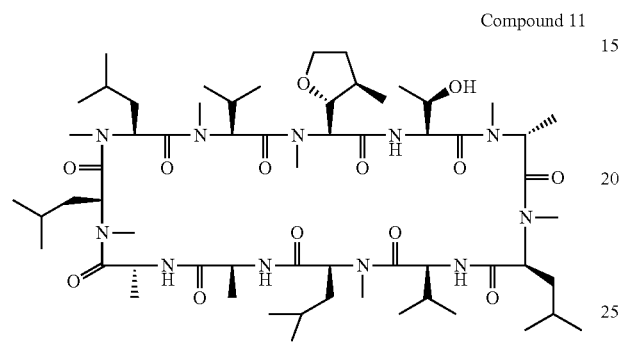

Compound 11 was prepared from Compound 8 by adapting the procedure described in Scheme 1 to prepare Intermediate 1. The anion formed was quenched with methyl iodide to give Compound 11.

ES/MS: 1204.72 MH+

$^1$H NMR (CDCl$_3$, ppm) δ 7.25 (d, 1H, amide NH), 7.48 (d, 1H, amide NH), 7.81 (d, 1H, amide NH), 8.67 (d, 1H, amide NH).

Example 12

Preparation of Compound 12 ([(2R)-2-[(2R,3R)-5-hydroxy-3-methyl-tetrahydrofuran-2-yl]-2-(methyl-amino)acetic acid]$^1$[(R)-methyl-Sar]$^3$ cyclosporin A) from Intermediate 3.3

Scheme 4

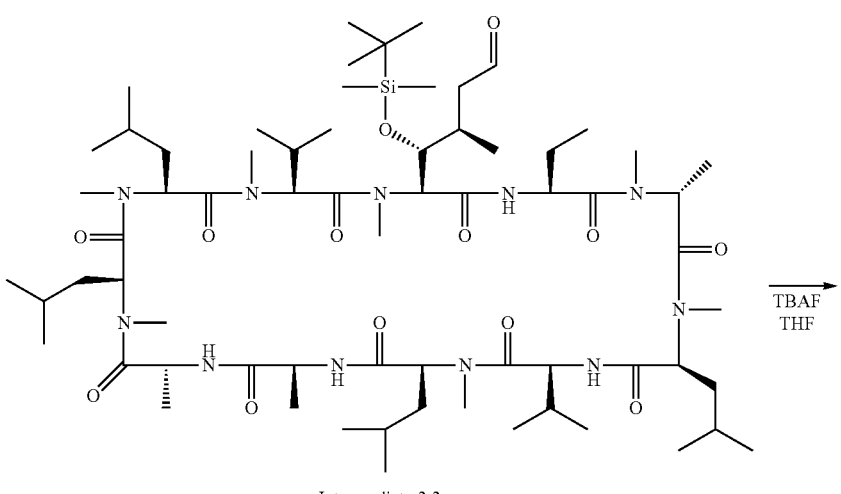

Intermediate 3.3

-continued

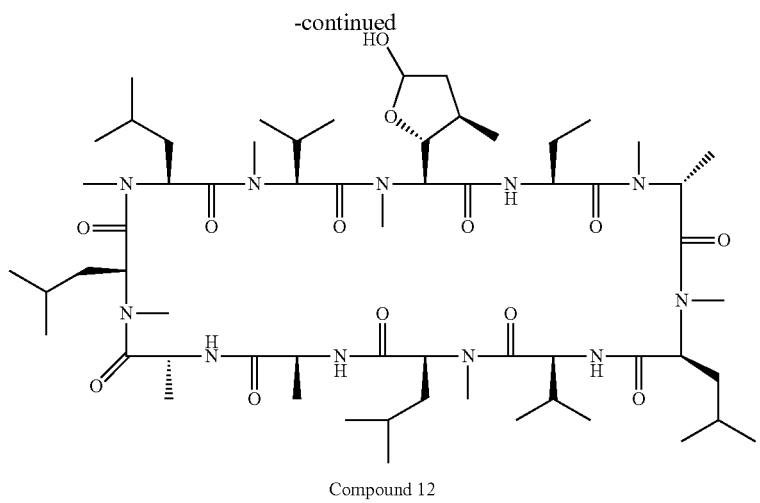

Compound 12

To a solution of [(2S,3R,4R)-3-[tert-butyl(dimethyl)silyl]oxy-4-methyl-2-(methylamino)-6-1-oxo-hexanoic acid][1] [(R)-ethyl-Sar][3] cyclosporin A (Intermediate 3.3) (121 mg, 0.091 mmol) in THF (3 ml) was added tetrabutylammonium fluoride solution in THF (1M, 0.27 ml, 0.27 mmol) and the solution was stirred at room temperature over 2 hours. The reaction mixture was evaporated under reduced pressure to a yellow gum. The gum was dissolved in DCM and washed with water then brine, dried (MgSO$_4$), filtered and evaporated under reduced pressure to yield the product Compound 12 as a white solid (mixture of isomers).

ES/MS: 1204.38 MH$^+$ $^1$H NMR (CDCl$_3$, ppm) δ 6.66 (d, 1H, amide NH), 6.99 (d, 1H, amide NH), 7.11 (d, 1H, amide NH), 7.24 (d, 1H, amide NH), δ 7.30 (d, 1H, amide NH), 7.44 (d, 1H, amide NH), 7.90 (d, 1H, amide NH), 8.24 (d, 1H, amide NH).

Compounds 13 and 14 were prepared as shown in Scheme 4.

Example 13

Preparation of Compound 13 ([(2S)-2-[(2R,3R)-5-Hydroxy-3-methyl-tetrahydrofuran-2-yl]-2-(methylamino)acetic acid][1] cyclosporin D) from Intermediate 7.3

Compound 13 was prepared as shown in Scheme 4 from [(2S,3R,4R)-3-[tert-butyl(dimethyl)silyl]oxy-4-methyl-2-(methylamino)-6-oxo-hexanoic acid][1] cyclosporin D (Intermediate 7.3).

ES/MS: 1204.92 MH$^+$ $^1$H NMR (CDCl$_3$, ppm) Mixture of two alcohol diastereoisomers in a ~80:20 ratio:

Major isomer δ 6.33 (d, 1H, amide NH), 6.74 (d, 1H, amide NH), 7.02 (d, 1H, amide NH), 7.10 (d, 1H, 1 amide NH);

Minor isomer δ 7.51 (d, 1H, amide NH), 7.93 (d, 1H, amide NH), 8.26 (d, 1H, amide NH), 8.72 (d, 1H, amide NH).

Example 14

Preparation of Compound 14 ([(2S)-2-[(2R,3R)-5-Hydroxy-3-methyl-tetrahydrofuran-2-yl]-2-(methylamino)acetic acid][1] [(R)-methyl-Sar][3] cyclosporin D) from Intermediate 6.3

Compound 13

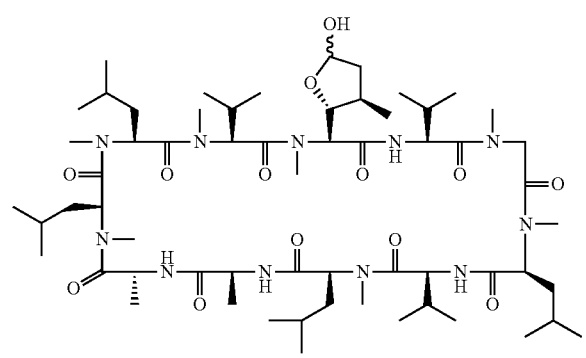

Compound 14

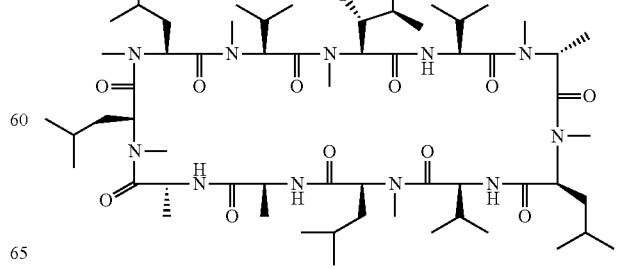

Compound 14 was prepared as shown in Scheme 4 from [(2S,3R,4R)-3-[tert-butyl(dimethyl)silyl]oxy-4-methyl-2-(methylamino)-6-oxo-hexanoic acid][1] [(R)-methyl-Sar][3] cyclosporin D (Intermediate 6.3)

ES/MS: 1218.78 MH+

$^1$H NMR (CDCl$_3$, ppm) Mixture of two alcohol diastereoisomers in a ~80:20 ratio Major isomer δ 6.59 (d, 1H, amide NH), 6.99 (d, 1H, amide NH), 7.10 (d, 1H, amide NH), 7.16 (d, 1H, 1 amide NH), Minor isomer δ 7.16 (d, 1H, 1 amide NH), 7.51 (d, 1H, amide NH), 7.97 (d, 1H, amide NH), 8.24 (d, 1H, amide NH).

Example 15

Preparation of Compound 15 ([(2S)-2-(methylamino)-2-[(2R,3R)-3-methyltetrahydropyran-2-yl] acetic acid][1] [(R)-methyl-Sar][3] cyclosporin A) commencing with Intermediate 3.3

Scheme 5

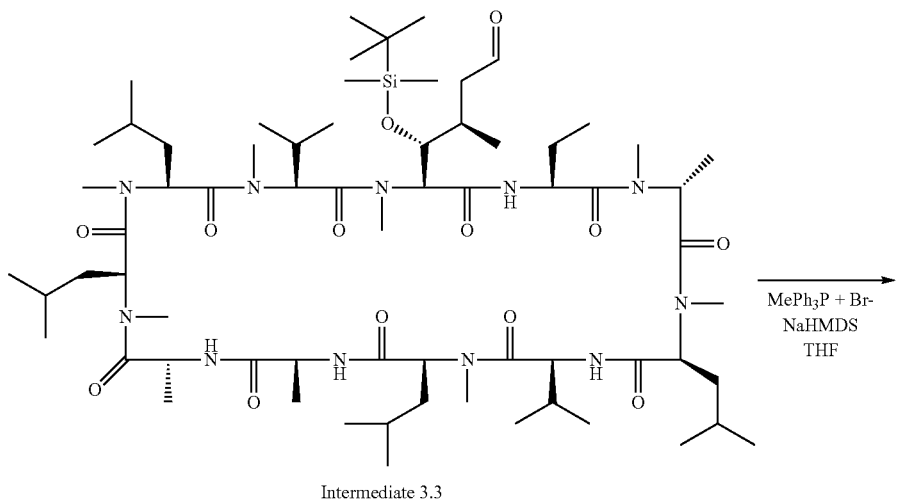

Intermediate 3.3

MePh$_3$P + Br-
NaHMDS
THF

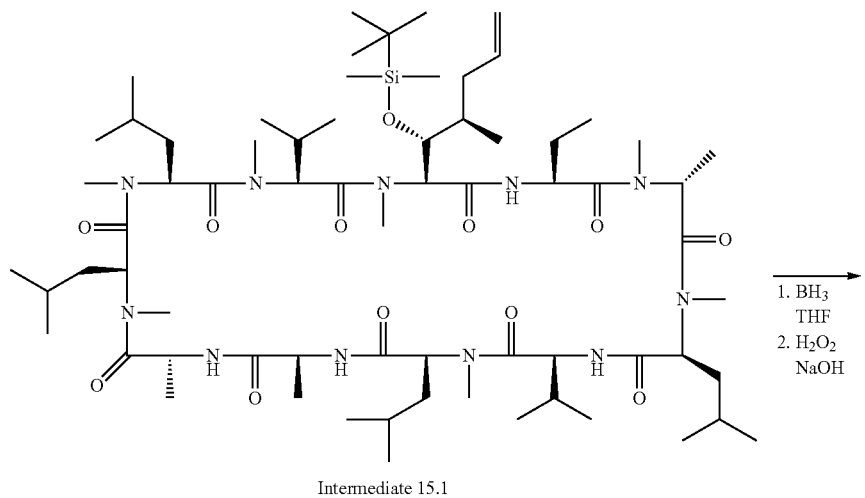

Intermediate 15.1

1. BH$_3$
   THF
2. H$_2$O$_2$
   NaOH

-continued
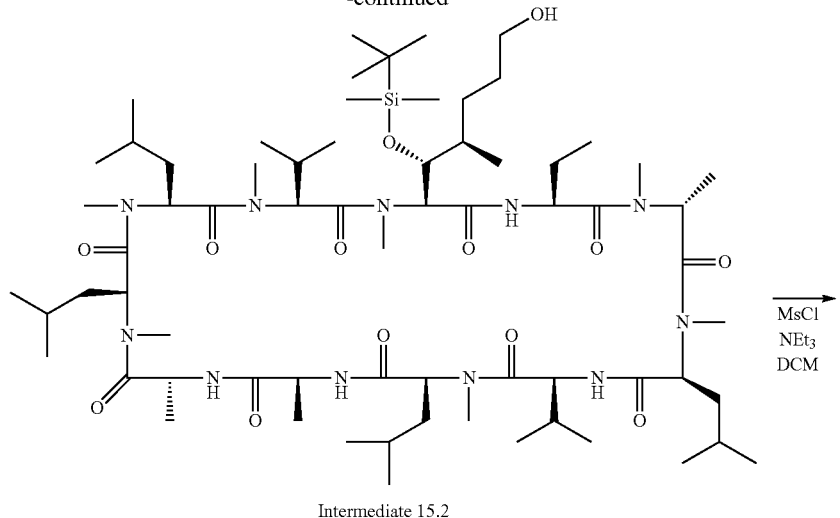
Intermediate 15.2
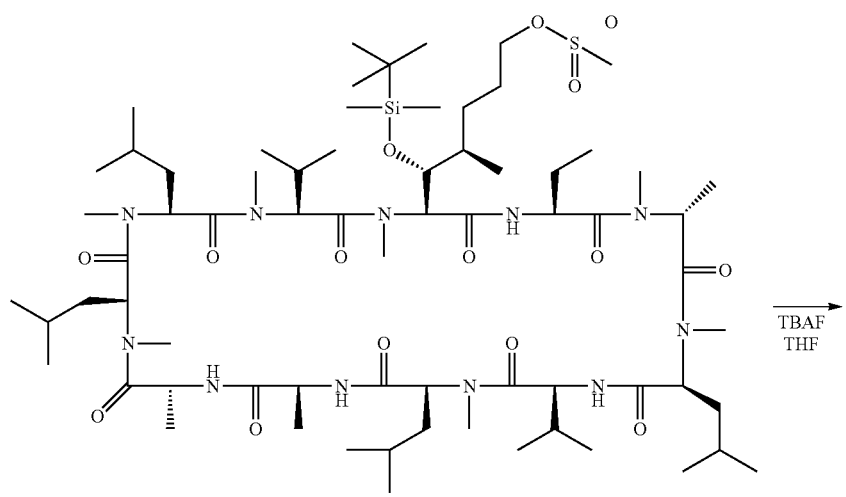
Intermediate 15.3
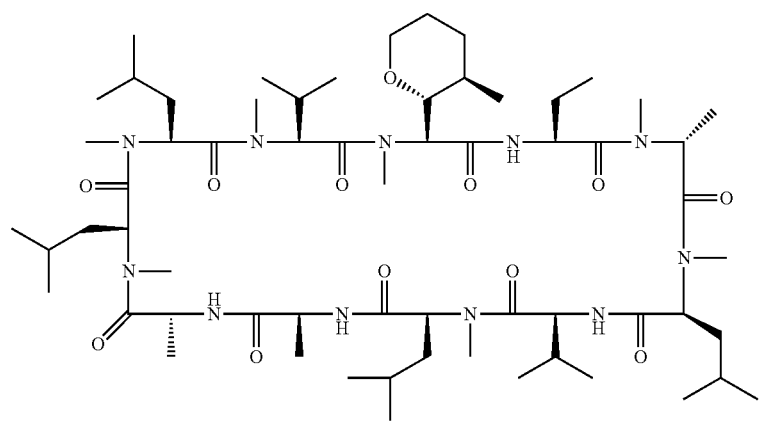
Compound 15

A. Preparation of Intermediate 15.1 from Intermediate 3.3

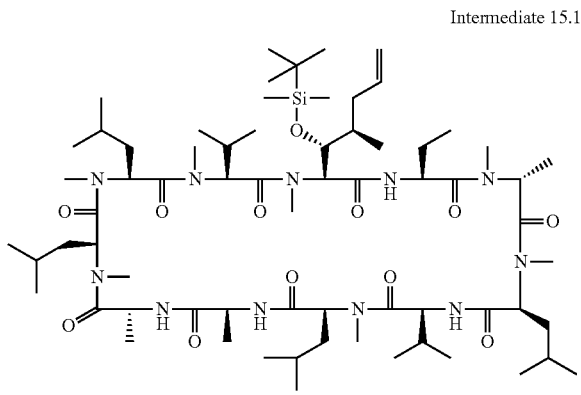 [SMILES: C=CC[C@@H](C)[C@@H](O[Si](C)(C)C(C)(C)C)[C@@H]1C(=O)N[C@H](CC)C(=O)N(C)[C@H](C)C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

Intermediate 15.1

To a suspension of methyltriphenylphosphonium bromide (1.08 g, 3.023 mmol) in THF (15 ml) at −78° C. under an atmosphere of nitrogen was added dropwise a solution of sodium hexamethyldisilazane in THF (2M, 1.33 ml, 2.66 mmol). The reaction mixture was stirred over 1 hour then warmed to 0° C. A solution of [(3R,4R,5S)-4-(t-butyldimethylsilanyloxy)-3-methyl-5-(methylamino)-1-oxo-hexanoic acid][1] [(R)-methyl-Sar][3] cyclosporin A (Intermediate 3.3) (500 mg, 0.379 mmol) in THF (5 ml) was added dropwise and the reaction mixture was allowed to warm to room temperature and stirred over 18 hours. The reaction mixture was diluted with water and extracted with ethyl acetate. The organic extract was dried (MgSO$_4$), filtered and evaporated under reduced pressure to yield the crude product as a yellow gum. The crude product was purified by column chromatography using a solvent gradient of 100% hexane to 50% acetone/50% hexane to give [(2S,3R,4R)-3-[tert-butyl(dimethyl)silyl]oxy-4-methyl-2-(methylamino)hept-6-enoic acid][1] [(R)-methyl-Sar][3] cyclosporin A (Intermediate 15.1) as a white solid.

$^1$H NMR (CDCl$_3$, ppm) δ 7.49 (d, 1H, amide NH), 7.59 (d, 1H, amide NH), 7.91 (d, 1H, amide NH), 8.51 (d, 1H, amide NH).

B. Preparation of Intermediate 15.2 from Intermediate 15.1

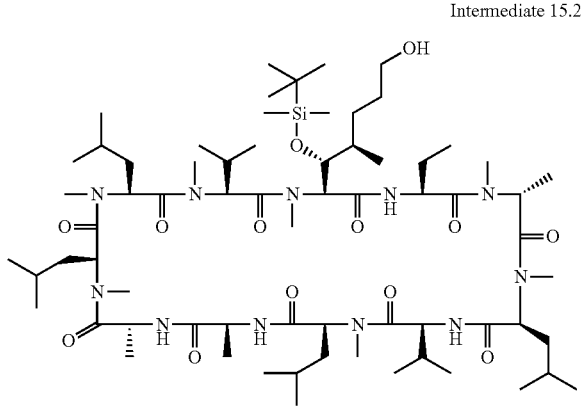 [SMILES: CC[C@H]1NC(=O)[C@@H]([C@H](O[Si](C)(C)C(C)(C)C)[C@H](C)CCCO)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Intermediate 15.2

To a solution of [(2S,3R,4R)-3-[tert-butyl(dimethyl)silyl]oxy-4-methyl-2-(methylamino)hept-6-enoic acid][1] [(R)-methyl-Sar][3] cyclosporin A (Intermediate 15.1) (200 mg, 0.152 mmol) in THF (4 ml) under an atmosphere of nitrogen was added borane tetrahydrofuran complex solution (1M, 0.76 ml, 0.760 mmol) and the reaction mixture was stirred at room temperature over 18 hours. A further portion of borane tetrahydrofuran solution (1M, 0.76 ml, 0.760 mmol) was added and the mixture stirred at room temperature for a further 4 hours. To the solution was added aq. sodium hydroxide (1M, 4 ml) followed by aq. hydrogen peroxide solution (30% w/v, 1.2 ml). The reaction mixture was stirred at room temperature over 70 hours. The reaction mixture was diluted with ethyl acetate and washed with water. The aqueous washing was extracted into ethyl acetate and the combined organics were washed with brine, dried (MgSO$_4$), filtered and evaporated under reduced pressure to yield Intermediate 15.2 as a white solid.

$^1$H NMR (CDCl$_3$, ppm) δ 7.55 (d, 1H, amide NH), 8.00 (m, 2H, amide NH), 8.54 (d, 1H, amide NH).

C. Preparation of Intermediate 15.3 from Intermediate 15.2

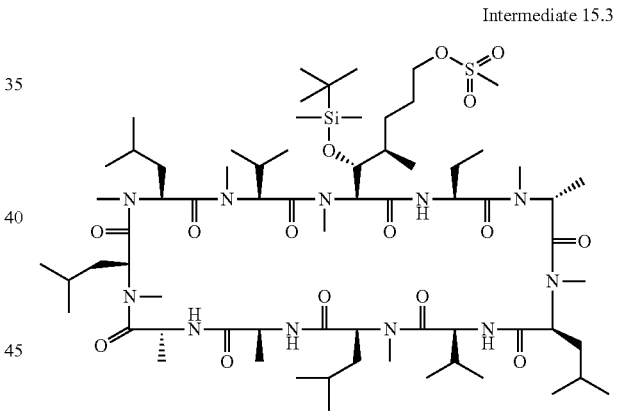

Intermediate 15.3

[(2S,3R,4R)-3-[tert-butyl(dimethyl)silyl]oxy-4-methyl-2-(methylamino)-7-methylsulfonyloxy-heptanoic acid][1] [(R)-methyl-Sar][3] cyclosporin A (Intermediate 15.3) was prepared in a similar manner to Intermediate 5 in Scheme 1 by condensing [(2S,3R,4R)-3-[tert-butyl(dimethyl)silyl]oxy-4-methyl-2-(methylamino)-7-oxy-heptanoic acid][1] [(R)-methyl-Sar][3] cyclosporin A (Intermediate 15.2) with methanesulphonyl chloride in DCM in the presence of triethylamine to give Intermediate 15.3.

$^1$H NMR (CDCl$_3$, ppm) δ 7.55 (d, 1H, amide NH), 7.64 (d, 1H, amide NH), 7.95 (d, 1H, amide NH), 8.40 (d, 1H, amide NH).

D. Preparation of Compound 15 ([(2S)-2-(methyl-amino)-2-[(2R,3R)-3-methyltetrahydropyran-2-yl]acetic acid]¹ [(R)-methyl-Sar]³ cyclosporin A) from Intermediate 15.3

[(2S,3R,4R)-3-[tert-butyl(dimethyl)silyl]oxy-4-methyl-2-(methylamino)-7-methylsulfonyloxy-heptanoic acid]¹ [(R)-methyl-Sar]³ cyclosporin A (Intermediate 15.3) was cyclized to give Compound 15 by stirring in the presence of TBAF in THF as described for the preparation of Compound 1 in Scheme 1.

ES/MS: 1203.06 MH⁺

¹H NMR (CDCl₃, ppm) δ 7.19 (d, 1H, amide NH), 7.47 (d, 1H, amide NH), 7.79 (d, 1H, amide NH), 7.88 (d, 1H, amide NH).

Compound 15

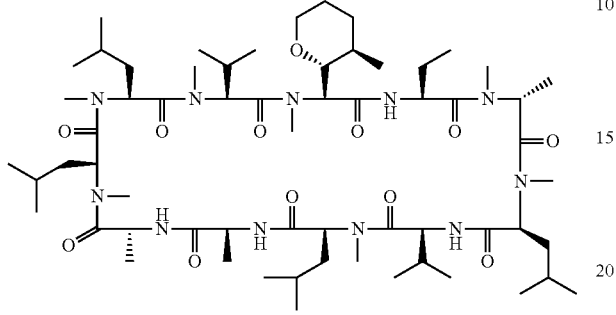

Example 16

Preparation of Compound 16 ([(2S)-2-(methyl-amino)-2-[(2R,3R)-3-methyloxepan-2-yl]acetic acid]¹ cyclosporin A) commencing with CsA Scheme 5

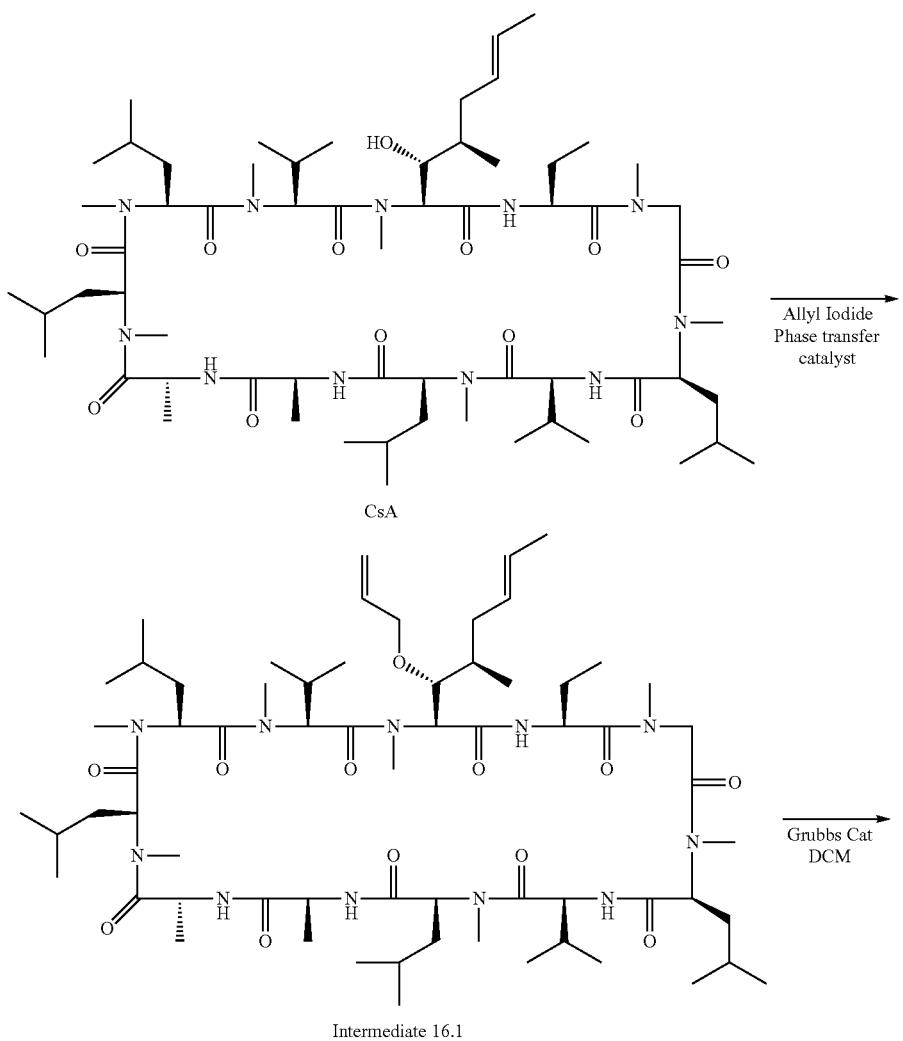

Intermediate 16.1

-continued

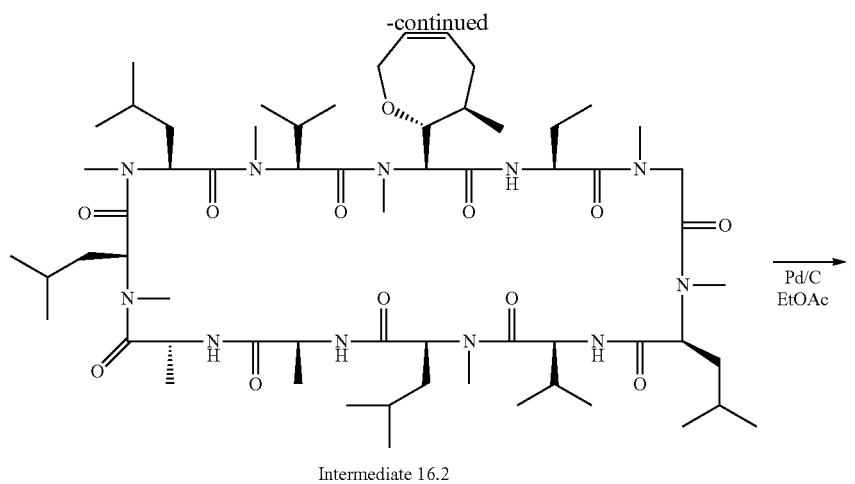

Intermediate 16.2

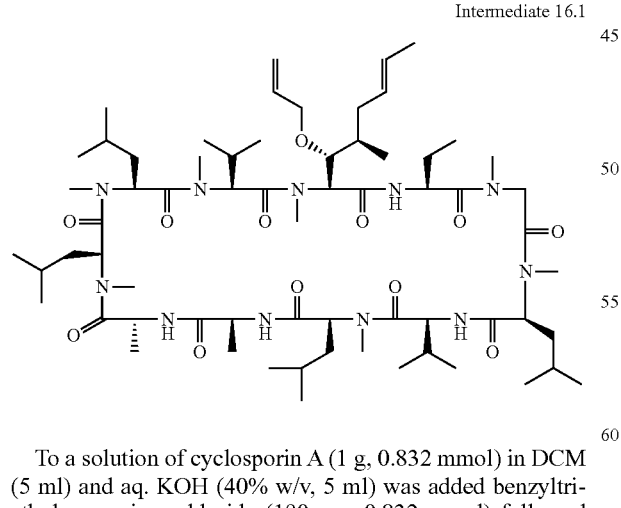

Compound 16

A. Preparation of Intermediate 16.1 from Cyclosporin A

Intermediate 16.1

To a solution of cyclosporin A (1 g, 0.832 mmol) in DCM (5 ml) and aq. KOH (40% w/v, 5 ml) was added benzyltriethylammonium chloride (190 mg, 0.832 mmol) followed by allyl iodide (0.152 ml, 1.664 mmol) and the reaction mixture was stirred at room temperature over 18 hours.

A further portion of allyl iodide (0.152 ml, 1.664 mmol) was added and the mixture stirred at room temperature for a further 18 hours. The reaction mixture was diluted with water and extracted into DCM twice. The combined extracts were dried (MgSO$_4$), filtered and evaporated under reduced pressure to yield the crude product as a yellow gum. The crude product was purified by column chromatography using a solvent gradient of 100% hexane to 40% acetone/60% hexane to give Intermediate 16.1 as a yellow solid.

$^1$H NMR (CDCl$_3$, ppm) δ 7.44 (d, 1H, amide NH), 7.49 (d, 1H, amide NH), 8.08 (d, 1H, amide NH), 8.51 (d, 1H, amide NH).

B. Preparation of Intermediate 16.2 from Intermediate 16.1

Intermediate 16.2

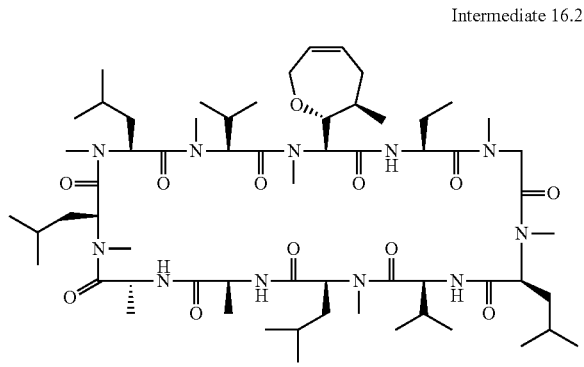 [SMILES: CC[C@H]1NC(=O)[C@@H]([C@@H]2OCC=CC[C@H]2C)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)CN(C)C1=O]

To a solution of [(E,2S,3R,4R)-3-allyloxy-4-methyl-2-(methylamino)oct-6-enoic acid][1] cyclosporin A (Intermediate 16.1) (100 mg, 0.0805 mmol) in DCM (10 ml) was added Grubb's catalyst, second generation (14 mg, 0.0161 mmol) and the reaction mixture was stirred at 45° C. over 70 hours. The reaction mixture was diluted with DCM and washed with water and aq. HCl (1M), dried (MgSO$_4$), filtered and evaporated under reduced pressure to yield the crude product as a brown gum. The crude product was purified by PTLC eluting with MTBE to give Intermediate 16.2 as a pale yellow solid.

ES/MS: 1200.80 MH$^+$ $^1$H NMR (CDCl$_3$, ppm) δ 7.44 (d, 1H, amide NH), 7.57 (d, 1H, amide NH), 8.12 (d, 1H, amide NH), 8.36 (d, 1H, amide NH).

C. Preparation of Compound 16 ([(2S)-2-(methylamino)-2-[(2R,3R)-3-methyloxepan-2-yl]acetic acid][1] cyclosporin A) from Intermediate 16.2

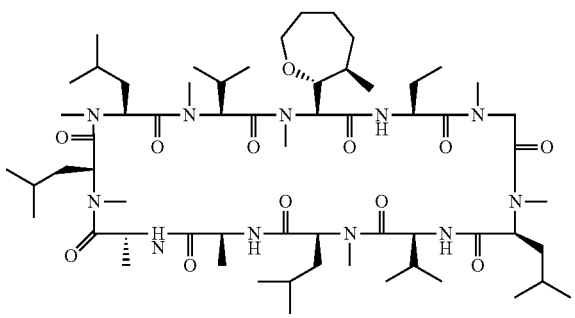

Compound 16

To a solution of [(2S)-2-(methylamino)-2-[(2R,3R)-3-methyl-2,3,4,7-tetrahydrooxepin-2-yl]acetic acid][1] cyclosporin A (Intermediate 16.2) (35 mg, 0.0292 mmol) in ethyl acetate (3 ml) was added 10% palladium on carbon (35 mg) and the reaction mixture was stirred under an atmosphere of hydrogen at room temperature over 18 hours. The reaction mixture was filtered over celite and the filtrate evaporated under reduced pressure to yield Compound 16 as a colorless gum.

ES/MS: 1202.88 MH$^+$ $^1$H NMR (CDCl$_3$, ppm) δ 7.36 (d, 1H, amide NH), 7.51 (d, 1H, amide NH), 8.02 (d, 1H, amide NH), 8.17 (d, 1H, amide NH).

Example 17

Preparation of Compound 17 ([(2S)-2-(methylamino)-2-[(2R,3R)-3-methyloxepan-2-yl]acetic acid][1] [(R)-methyl-Sar][3] cyclosporin A) commencing from [(R)-methyl-Sar][3] Cyclosporin A A. Preparation of Intermediate 17.1 from [(R)-methyl-Sar][3] Cyclosporin A

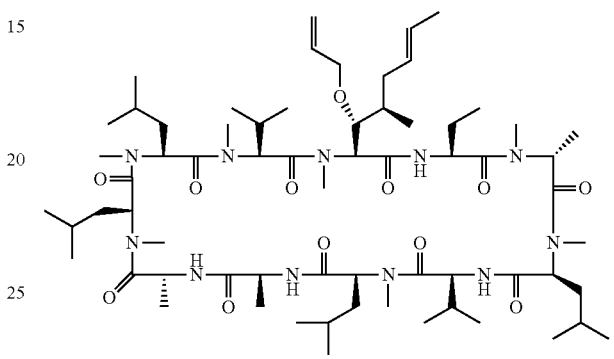

Intermediate 17.1

Using the above procedure shown in Scheme 5, [(E,2S,3R,4R)-3-allyloxy-4-methyl-2-(methylamino)oct-6-enoic acid][1] [(R)-methyl-Sar][3] cyclosporin A (Intermediate 17.1) was prepared from [(R)-methyl-Sar][3] cyclosporin A (preparation described in WO2013181339).

$^1$H NMR (CDCl$_3$, ppm) δ 7.42 (d, 1H, amide NH), 7.47 (d, 1H, amide NH), 8.07 (d, 1H, amide NH), 8.48 (d, 1H, amide NH).

B. Preparation of Intermediate 17.2 from Intermediate 17.1.

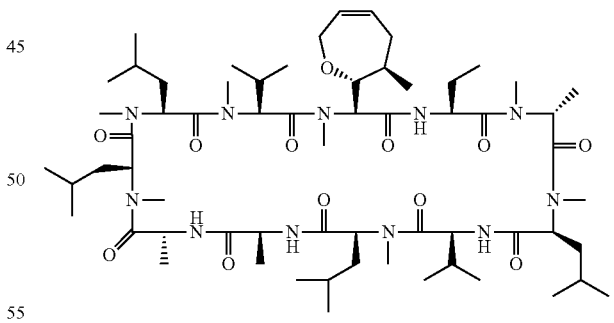

Intermediate 17.2

Using the above procedure shown in Scheme 5, [(2S)-2-(methylamino)-2-[(2R,3R)-3-methyl-2,3,4,7-tetrahydrooxepin-2-yl]acetic acid][1] [(R)-methyl-Sar][3] cyclosporin A (Intermediate 17.2) was prepared from [(E,2S,3R,4R)-3-allyloxy-4-methyl-2-(methylamino)oct-6-enoic acid][1] [(R)-methyl-Sar][3] cyclosporin A (Intermediate 17.1).

ES/MS: 1214.91 MH$^+$ $^1$H NMR (CDCl$_3$, ppm) δ 7.45 (d, 1H, amide NH), 7.55 (d, 1H, amide NH), 8.12 (d, 1H, amide NH), 8.37 (d, 1H, amide NH).

C. Preparation of Compound 17 from Intermediate 17.2.

Compound 17

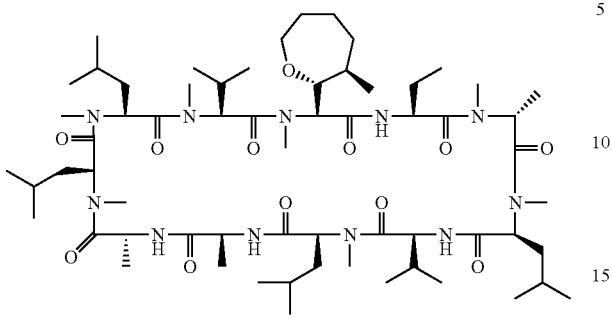

Using the above procedure shown in Scheme 5, [(2S)-2-(methylamino)-2-[(2R,3R)-3-methyloxepan-2-yl]acetic acid]$^1$ [(R)-methyl-Sar]$^3$ cyclosporin A (Compound 17) was prepared from [(2S)-2-(methylamino)-2-[(2R,3R)-3-methyl-2,3,4,7-tetrahydrooxepin-2-yl]acetic acid]$^1$ [(R)-methyl-Sar]$^3$ cyclosporin A (Intermediate 17.2).

ES/MS: 1216.76 MH$^+$ $^1$H NMR (CDCl$_3$, ppm) δ 7.38 (d, 1H, amide NH), 7.52 (d, 1H, amide NH), 8.06 (d, 1H, amide NH), 8.23 (d, 1H, amide NH).

Example 18

Preparation of Compound 18 ([(2S)-2-(methylamino)-2-[(2S,3R)-3-methyltetrahydrofuran-2-yl]acetic acid]$^1$ [(R)-methyl-Sar]$^3$ cyclosporin A) commencing with Intermediate 18.1

Scheme 6

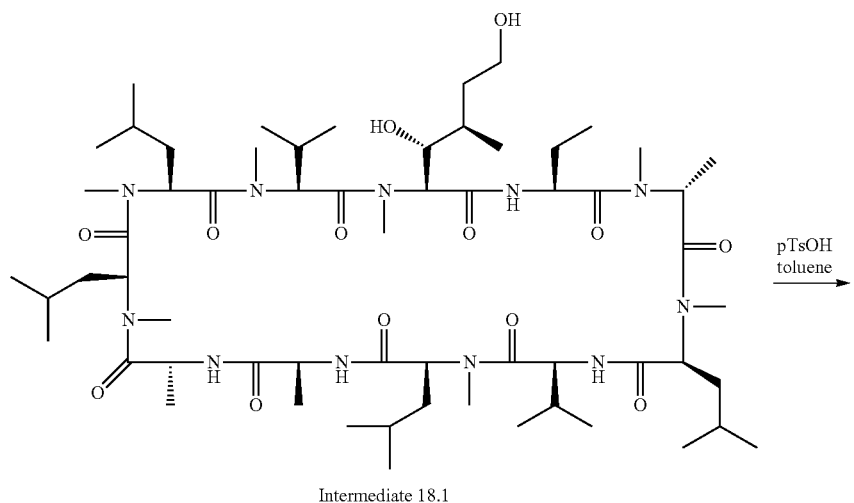

Intermediate 18.1

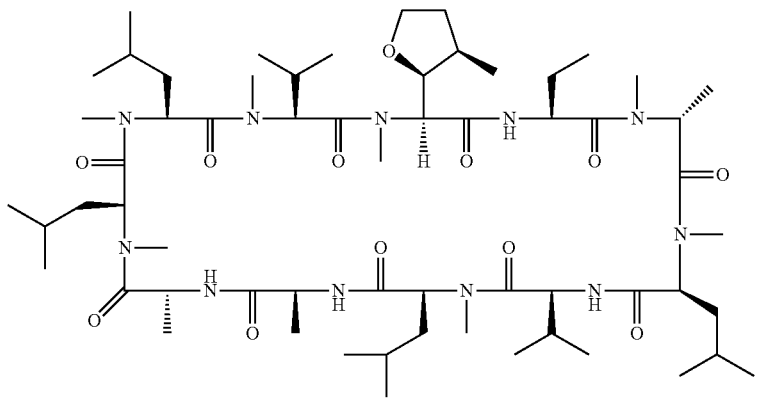

Compound 18

The preparation of [(2S,3R,4R)-3,6-dihydroxy-4-methyl-2-(methylamino) hexanoic acid]¹ [(R)-methyl-Sar]³ cyclosporin A (Intermediate 18.1) was described in WO2013181339.

To a solution of [(2S,3R,4R)-3,6-dihydroxy-4-methyl-2-(methylamino) hexanoic acid]¹ [(R)-methyl-Sar]³ cyclosporin A (Intermediate 18.1) (121 mg, 0.1 mmol) in toluene (3 ml) was added p-toluenesulphonic acid (5 mg) and the solution was stirred at reflux for 3 h. The reaction mixture was evaporated under reduced pressure to a yellow gum. The gum was dissolved in DCM purified by PTLC, eluting with 30% acetone/70% hexane to give Compound 18 as a white solid.

ES/MS: 1188.84 MH⁺
¹H NMR (CDCl₃, ppm) δ 7.29 (d, 1H, amide NH), 7.58 (d, 1H, amide NH), 7.75 (d, 1H, amide NH), 8.01 (d, 1H, amide NH).

Example 19

Preparation of Compound 19 ([(2S)-2-[(2S,3R)-1,3-dimethylpyrrolidin-2-yl]-2-(methylamino)acetic acid]¹ [(R)-methyl-Sar]³ cyclosporin A) commencing with Intermediate 3.3

A. Preparation of Intermediate 19.1 from Intermediate 3.3

Scheme 7

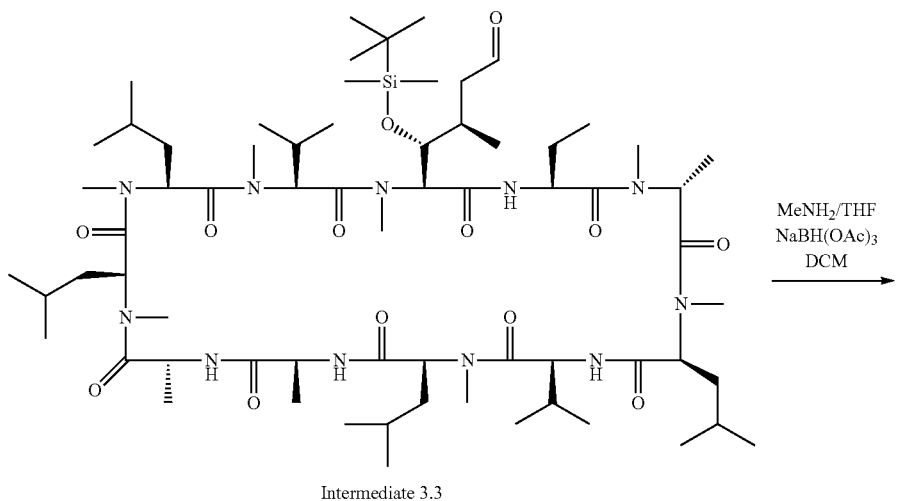

Intermediate 3.3

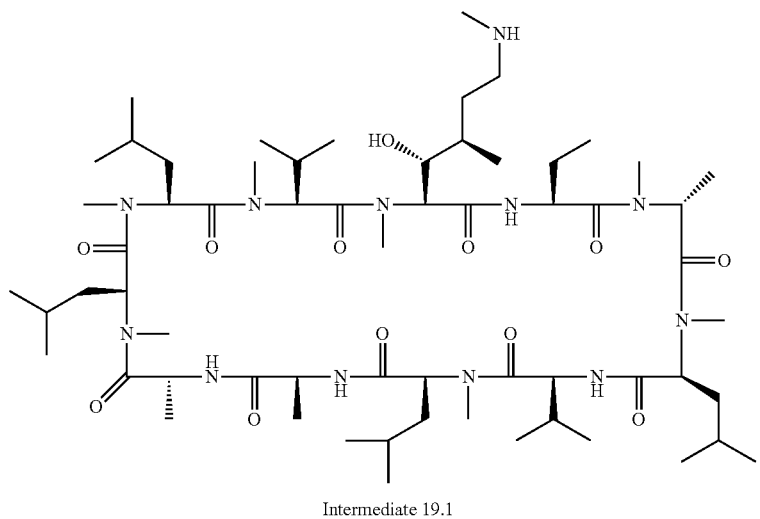

Intermediate 19.1

[(2S,3R,4R)-3-[tert-butyl(dimethyl)silyl]oxy-4-methyl-2-(methylamino)-6-oxy-hexanoic acid]¹ [(R)-methyl-Sar]³ cyclosporin A (Intermediate 3.3) was reacted with methylamine as described previously in WO2013181339 to give Intermediate 19.1 ([(2R,3R,4R)-3-[tert-butyl(dimethyl)si- lyl]oxy-4-methyl-2,6-bis(methylamino)hexanoic acid]¹ [(R)-methyl-Sar]³ cyclosporin A) as a white solid. ES/MS: 1333.93 MH⁺.

B. Preparation of Intermediate 19.2 from Intermediate 19.1

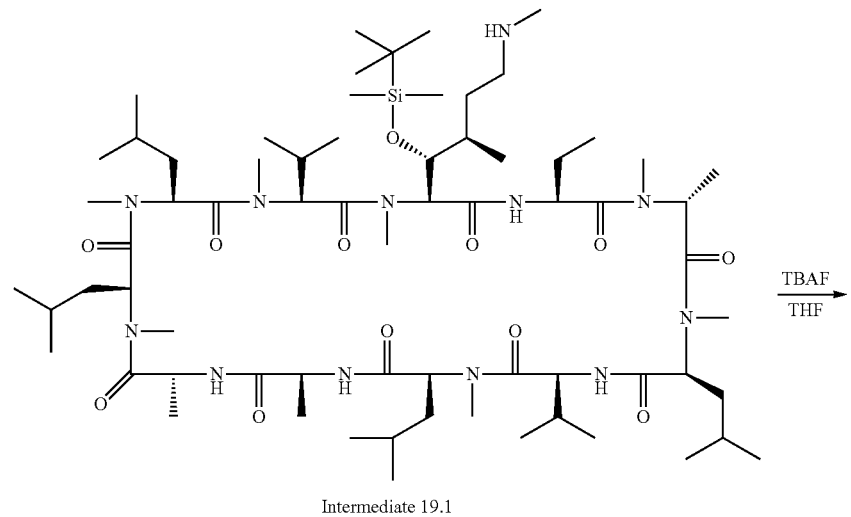

Intermediate 19.1

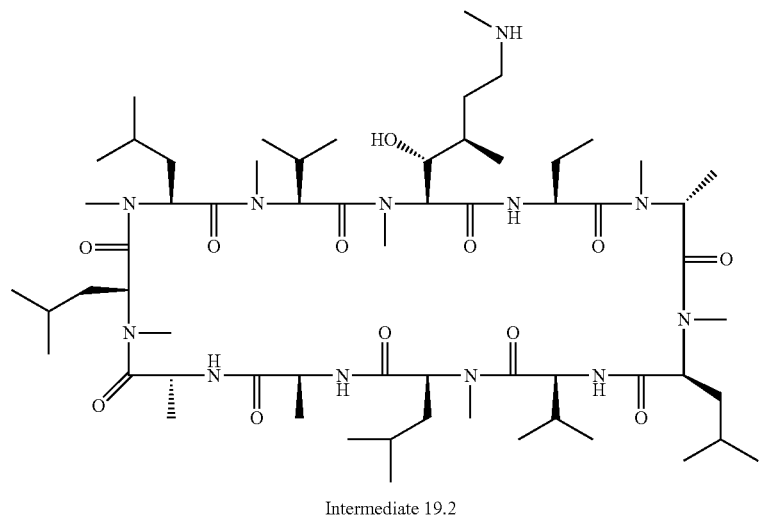

Intermediate 19.2

To a solution of [(2R,3R,4R)-3-[tert-butyl(dimethyl)silyl]oxy-4-methyl-2,6-bis(methylamino)hexanoic acid][1] [(R)-methyl-Sar][3] cyclosporin A (Intermediate 19.1) (0.26 g) was added TBAF (1.0M in THF, 0.4 ml) and the solution was stirred for 3 h. The reaction mixture was evaporated under reduced pressure to a yellow gum. The gum was purified by passing through an SCX column (MeOH—10% NH$_3$/MeOH as eluent). The basic fractions were collected to give Intermediate 19.2 as a white solid.

ES/MS: 1219.85 MH$^+$ $^1$H NMR (CDCl$_3$, ppm) δ 7.26 (d, 1H, amide NH), 7.44 (d, 1H, amide NH), 7.90 (d, 1H, amide NH), 7.97 (d, 1H, amide NH).

C. Preparation of Compound 19 ([(2S)-2-[(2S,3R)-1,3-dimethylpyrrolidin-2-yl]-2-(methylamino)acetic acid][1] [(R)-methyl-Sar][3] cyclosporin A) from Intermediate 19.2

Scheme 9

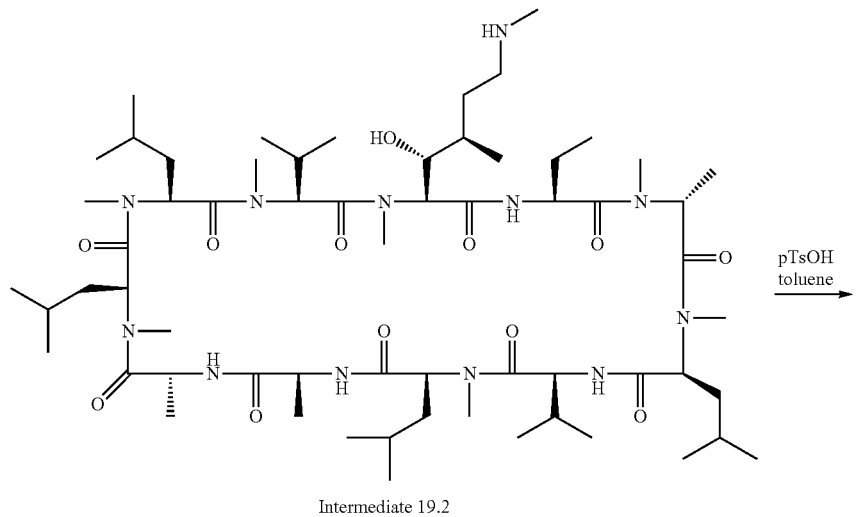

Intermediate 19.2

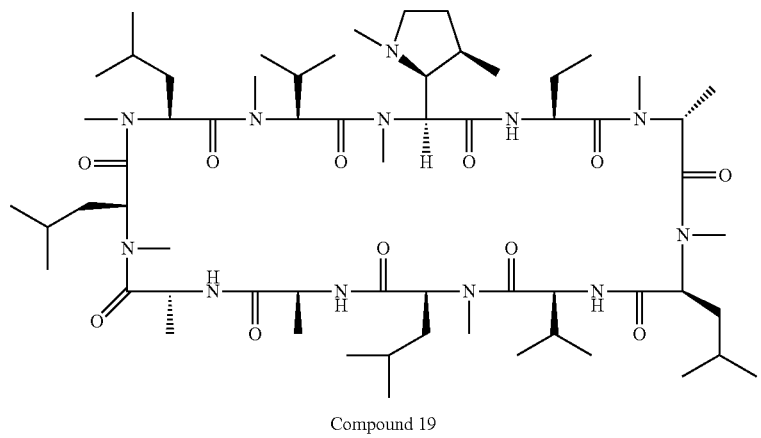

Compound 19

To a solution of [(2R,3R,4R)-3-hydroxy-4-methyl-2,6-bis(methylamino)hexanoic acid][1] [(R)-methyl-Sar][3] cyclosporin A (Intermediate 19.2) was added pTsOH (5 mg) and the reaction mixture heated at reflux for 2 h. The reaction mixture was diluted with ethyl acetate then washed with H$_2$O, NaHCO3 (sat. soln.) and brine. The organic phase was dried, filtered and evaporated. The crude product was dissolved in DCM and purified by PTLC, eluting with 10% MeOH/90% DCM to give Compound 19 as a white solid.

ES/MS: 1201.87 MH$^+$ $^1$H NMR (CDCl$_3$, ppm) δ 7.18 (d, 1H, amide NH), 7.58 (d, 1H, amide NH), 7.76 (d, 1H, amide NH), 7.95 (d, 1H, amide NH).

Example 20

Preparation of Compound 20 ([(2S)-2-(methylamino)-2-[(2S,3R)-3-methylpyrrolidin-2-yl]acetic acid][1] [(R)-methyl-Sar][3] cyclosporin A) from Intermediate 20.1

Scheme 10

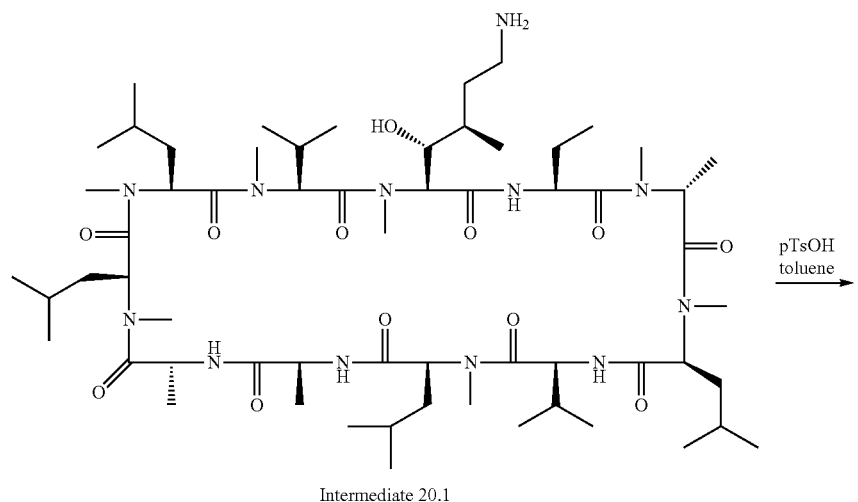

Intermediate 20.1

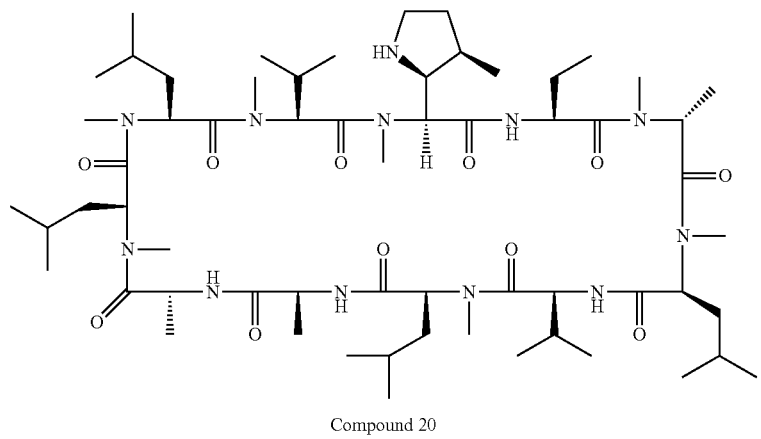

Compound 20

[(2R,3R,4R)-3-[tert-butyl(dimethyl)silyl]oxy-4-methyl-2,6-bis(methylamino)hexanoic acid]¹ [(R)-methyl-Sar]³ cyclosporin A (Intermediate 20.1) was prepared from Intermediate 3.3 by reaction with ammonia and sodium triacetoxyborohydride as described previously in WO2013181339. [(2R,3R,4R)-6-amino-3-hydroxy-4-methyl-2-(methylamino)hexanoic acid]¹ [(R)-methyl-Sar]³ cyclosporin A (Intermediate 20.1) was cyclized by heating with pTSA in toluene to give Compound 20 as a white solid.

ES/MS: 1187.79 MH⁺

¹H NMR (CDCl₃, ppm) δ 7.22 (d, 1H, amide NH), 7.62 (d, 1H, amide NH), 7.80 (d, 1H, amide NH), 8.18 (d, 1H, amide NH).

Example 21

Preparation of Compound 21 ([(2R)-2-[(5R,6R)-3,5-dimethyl-2-oxo-1,3-oxazinan-6-yl]-2-(methylamino)acetic acid]¹ cyclosporin A) commencing with Intermediate 21.1

Scheme 11

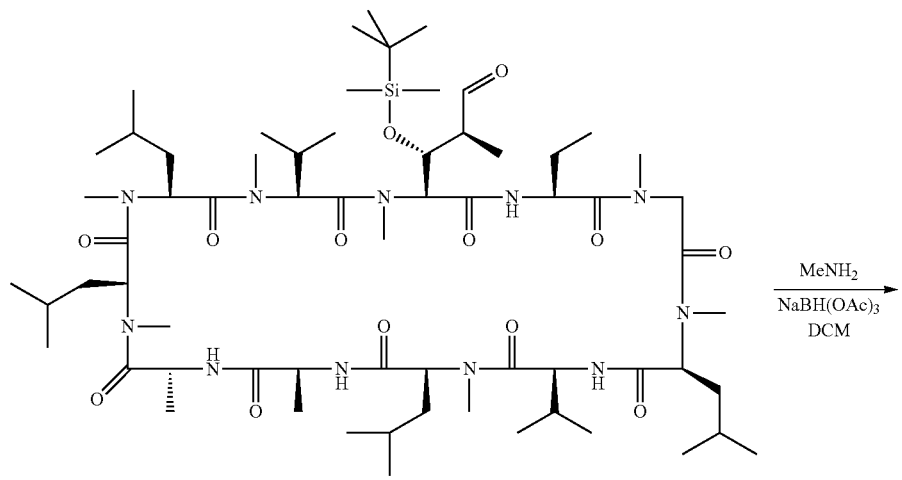

Intermediate 21.1

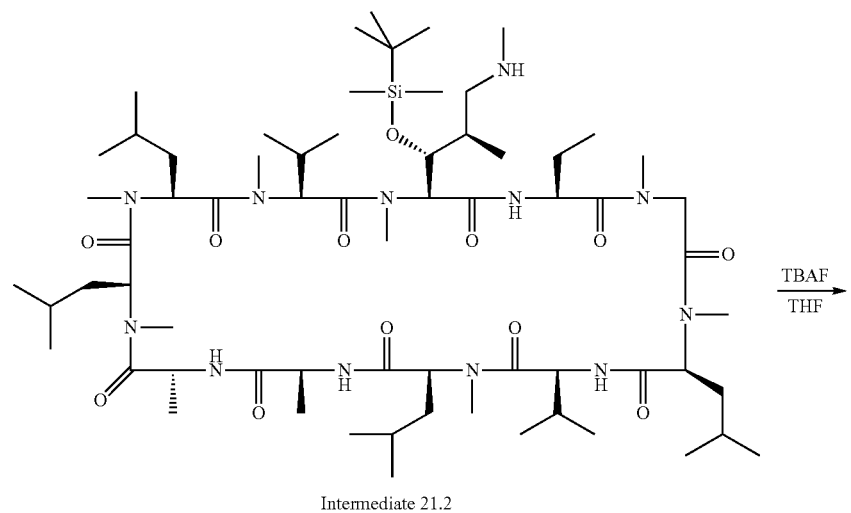

Intermediate 21.2

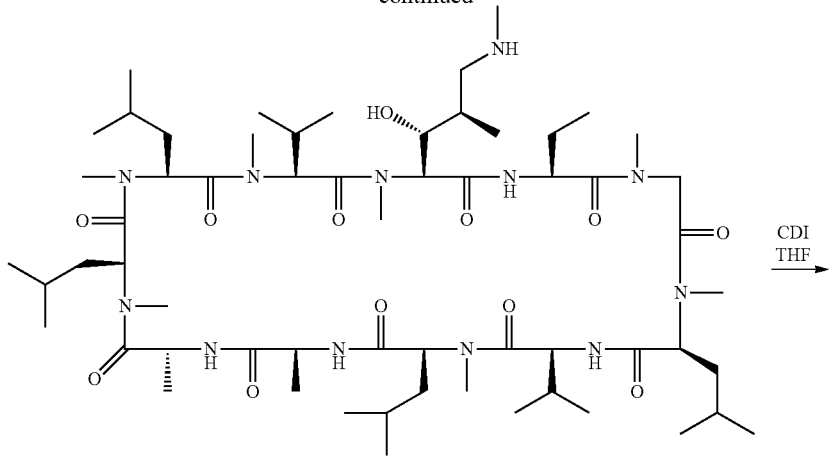

Intermediate 21.3

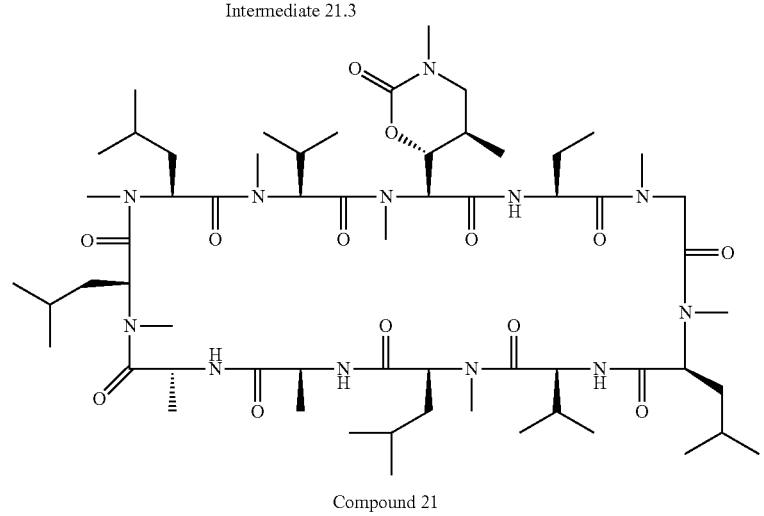

Compound 21

A. Preparation of Intermediate 21.2 from Intermediate 21.1.

[(2R,3R,4R)-3-[tert-butyl(dimethyl)silyl]oxy-4-methyl-2-(methylamino)-5-oxo-pentanoic acid][1] cyclosporin A (Intermediate 21.1) was prepared as described in WO2013181339.

To a solution of [(2R,3R,4R)-3-[tert-butyl(dimethyl)silyl]oxy-4-methyl-2-(methylamino)-5-oxo-pentanoic acid][1] cyclosporin A (Intermediate 21.1) (0.1 mmol) in DCM (2 ml) was added sodium triacetoxyborohydride (0.2 mmol) and methylamine (2.0M in THF, 1 ml) and the reaction mixture stirred for 20 h. The reaction mixture was diluted with $H_2O$, then extracted with DCM, dried, filtered and evaporated to give Intermediate 21.2 as a gum.

ES/MS: 1305.98 MH+

$^1$H NMR (CDCl$_3$, ppm) δ 7.62 (d, 1H, amide NH), 7.65 (d, 1H, amide NH), 7.81 (d, 1H, amide NH), 8.37 (d, 1H, amide NH).

B. Preparation of Intermediate 21.3 from Intermediate 21.2.

[(2S,3R,4R)-3-[tert-butyl(dimethyl)silyl]oxy-4-methyl-2,5-bis(methylamino)pentanoic acid][1] cyclosporin A (Intermediate 21.2) was deprotected by stirring with TBAF and THF to give Intermediate 21.3 as a white solid.

ES/MS: 1192.00 MH+

$^1$H NMR (CDCl$_3$, ppm) δ 7.42 (d, 1H, amide NH), 7.49 (d, 1H, amide NH), 8.05 (d, 1H, amide NH), 8.40 (d, 1H, amide NH).

C. Preparation of Compound 21 from Intermediate 21.3.

[(2S,3R,4R)-3-hydroxy-4-methyl-2,5-bis(methylamino)pentanoic acid][1] cyclosporin A (Intermediate 21.3) (0.05 mmol) in THF was treated with carbonyl diimidazole CDI (0.02 g) and the mixture stirred for 18 h. The reaction mixture was diluted with $H_2O$ then extracted with ethyl acetate and the organic phase dried, filtered and evaporated to yield Compound 21 ([(2R)-2-[(5R,6R)-3,5-dimethyl-2-oxo-1,3-oxazinan-6-yl]-2-(methylamino)acetic acid][1] cyclosporin A) as a white solid.

ES/MS: 1217.81 MH+

$^1$H NMR (CDCl$_3$, ppm) δ 7.39 (d, 1H, amide NH), 7.60 (d, 1H, amide NH), 7.89 (d, 1H, amide NH), 8.42 (d, 1H, amide NH).

Example 22
Preparation of Compound 22 ((2S)-2-[5R,6R)-3,5-Dimethyl-2-oxo-1,3-oxazinan-6-yl]-2-(methyl-amino)acetic acid]¹ [(R)-methyl-Sar]³ cyclosporin A) commencing with Intermediate 22.1
Scheme 12
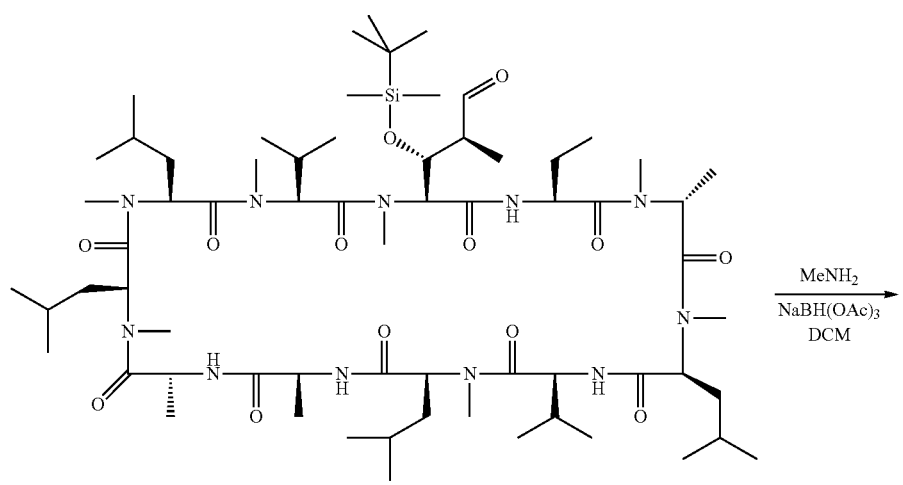
Intermediate 22.1
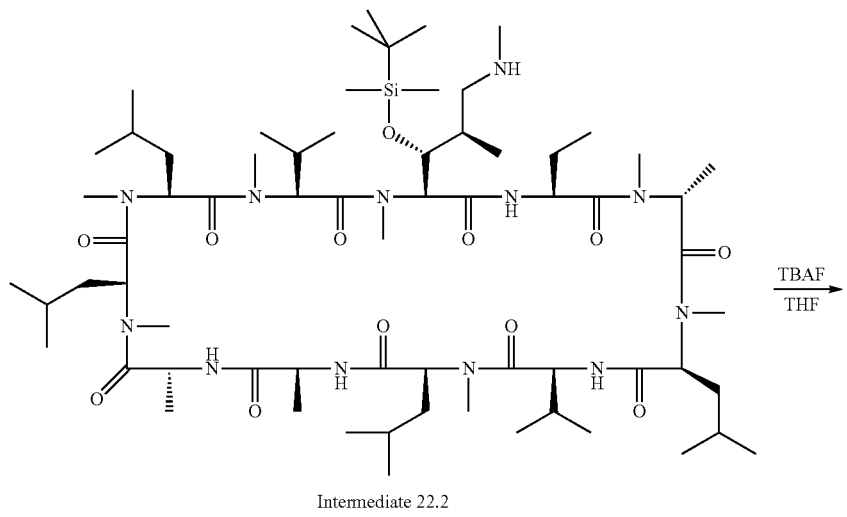
Intermediate 22.2

-continued

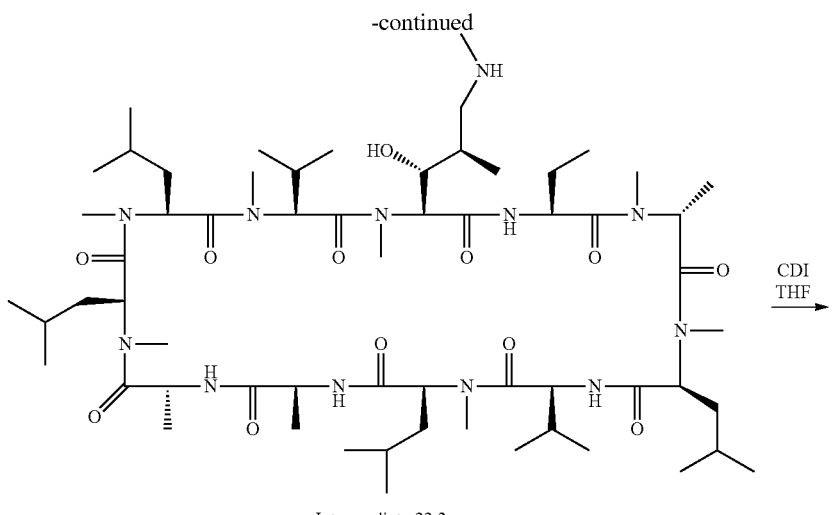

Intermediate 22.3

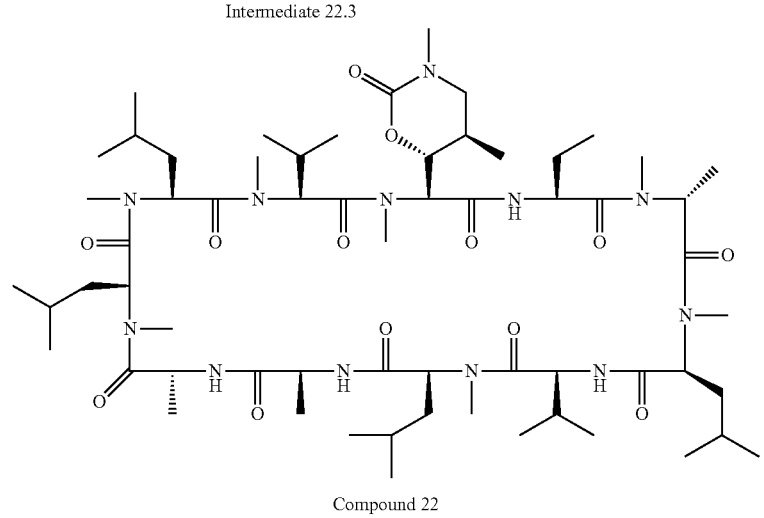

Compound 22

A. Preparation of Intermediate 22.1.

[(2R,3R,4R)-3-[tert-butyl(dimethyl)silyl]oxy-4-methyl-2-(methylamino)-5-oxo-pentanoic acid][1] [(R)-methyl-Sar][3] cyclosporin A (Intermediate 22.1) was prepared as described in WO2013181339.

B. Preparation of Intermediate 22.2 from Intermediate 22.1.

[(2S,3R,4R)-[tert-butyl(dimethyl)silyl]oxy-4-methyl-2,5-bis(methylamino)pentanoic acid][1] [(R)-methyl-Sar][3] cyclosporin A (Intermediate 22.2) was prepared by condensing Intermediate 22.1 with methylamine in the presence of sodium triacetoxyborohydride in DCM as described for the preparation of Intermediate 21.2.

ES/MS: 1319.89 MH+

C. Preparation of Intermediate 22.3 from Intermediate 22.2.

[(2S,3R,4R)-3-hydroxy-4-methyl-2, 5-bis(methylamino)pentanoic acid][1] [(R)-methyl-Sar][3] cyclosporin A (Intermediate 22.2) was deprotected by stirring with TBAF and THF to give Intermediate 22.3 ([(2S,3R,4R)-3-hydroxy-4-methyl-2, 5-bis(methylamino)pentanoic acid][1] [(R)-methyl-Sar][3] cyclosporin A) as a white solid.

ES/MS: 1205.86 MH+

$^1$H NMR (CDCl$_3$, ppm) δ 7.48 (d, 1H, amide NH), 7.57 (d, 1H, amide NH), 7.93 (d, 1H, amide NH), 8.22 (d, 1H, amide NH).

Preparation of Compound 22 ((2S)-2-[5R,6R)-3,5-Dimethyl-2-oxo-1,3-oxazinan-6-yl]-2-(methylamino)acetic acid][1] [(R)-methyl-Sar][3] cyclosporin A) from Intermediate 22.3

Compound 22

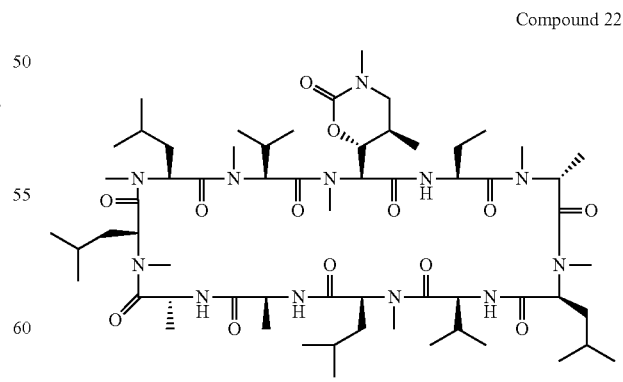

[(2S,3R,4R)-3-hydroxy-4-methyl-2,5-bis(methylamino) pentanoic acid][1] [(R)-methyl-Sar][3] cyclosporin A (Intermediate 22.3) was cyclized with CDI, as described for the synthesis of Compound 21, to give Compound 22.

ES/MS: 1231.8 MH+
$^1$H NMR (CDCl$_3$, ppm) δ 7.41 (d, 1H, amide NH), 7.59 (d, 1H, amide NH), 7.91 (d, 1H, amide NH), 8.42 (d, 1H, amide NH).
Example 23
Preparation of Compound 23 ([(2R)-2-[(5R,6R)-3,5-dimethyl-1,3-oxazinan-6-yl]-2-(methylamino)acetic acid]$^1$ cyclosporin A) from Intermediate 21.3
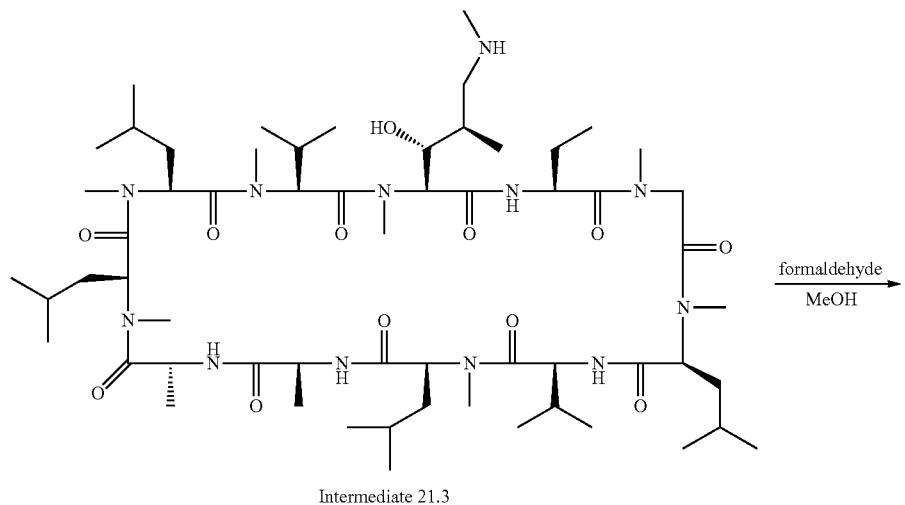
Intermediate 21.3
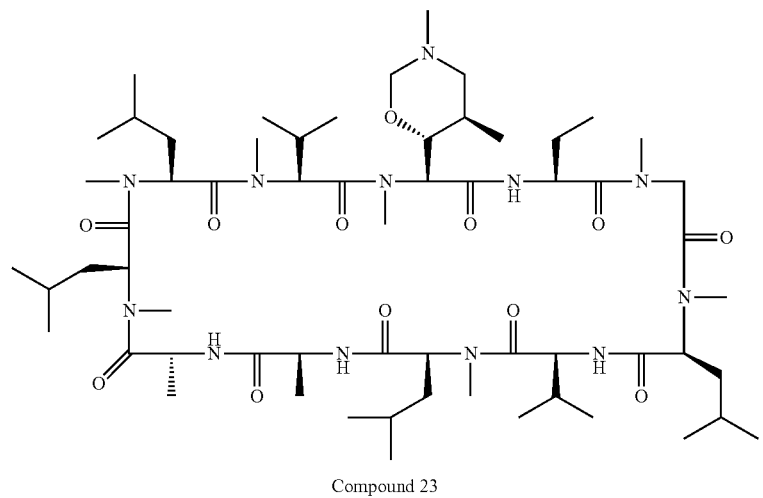
Compound 23

[(2S,3R,4R)-3-hydroxy-4-methyl-2,5-bis(methylamino)pentanoic acid][1] cyclosporin A (Intermediate 21.3) (0.1 g, 0.08 mmol) in MeOH (2 ml) was treated with formaldehyde (36% aq. soln., 0.5 ml) and the mixture stirred for 18 h. The reaction mixture was diluted with H$_2$O then extracted with ethyl acetate and the organic phase dried, filtered and evaporated to yield Compound 23 as a white solid.

ES/MS: 1203.87 MH$^+$

$^1$H NMR (CDCl$_3$, ppm) δ 7.08 (d, 1H, amide NH), 7.35 (d, 1H, amide NH), 7.74 (d, 2H, amide NH).

Example 24

Preparation of Compound 24 ((2S)-2-[5R,6R)-3,5-Dimethyl-1,3-oxazinan-6-yl]-2-(methylamino)acetic acid][1] [(R)-methyl-Sar][3] cyclosporin A) from Intermediate 22.2

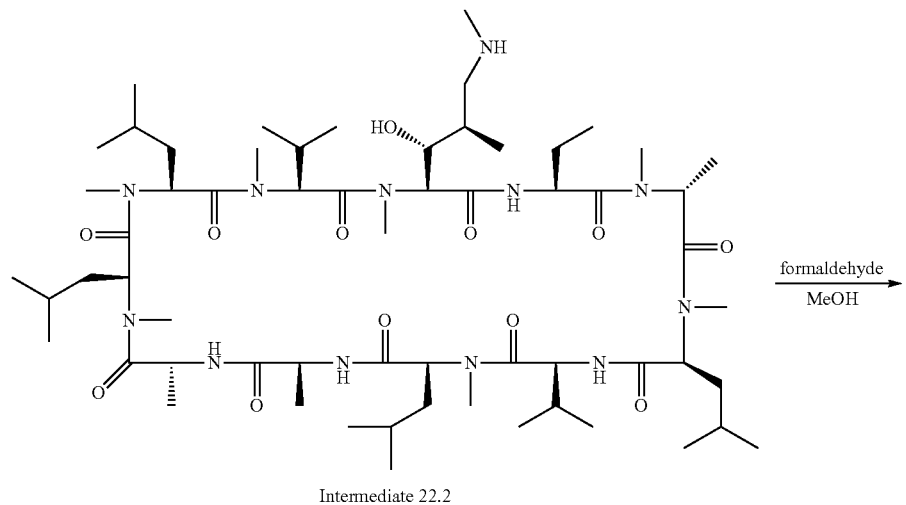

Intermediate 22.2

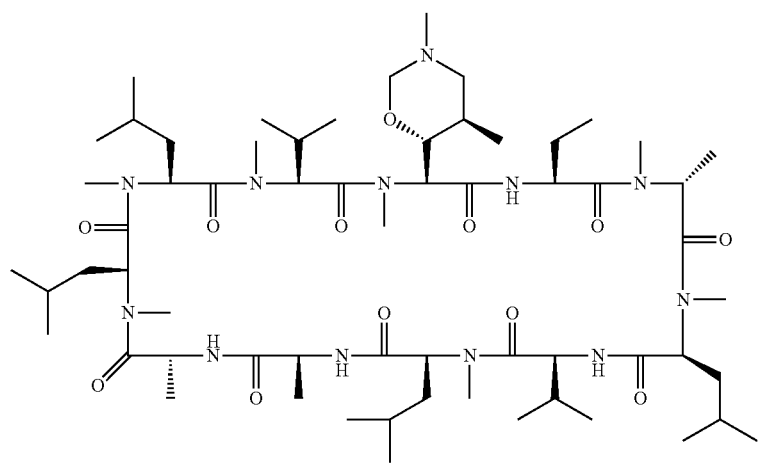

Compound 24

Compound 24 was prepared in a similar manner to Compound 23.
ES/MS: 1218.0 MH+
$^1$H NMR (CDCl$_3$, ppm) δ 7.16 (d, 1H, amide NH), 7.38 (d, 1H, amide NH), 7.78 (d, 1H, amide NH), 7.83 (d, 1H, amide NH).
Example 25
Preparation of Compound 25 ([(2S)-2-(methylamino)-2-[(2R,3R)-3-methyl-2,3-dihydrofuran-2-yl] acetic acid]$^1$ [(R)-methyl-Sar]$^3$ cyclosporin A) from Compound 12
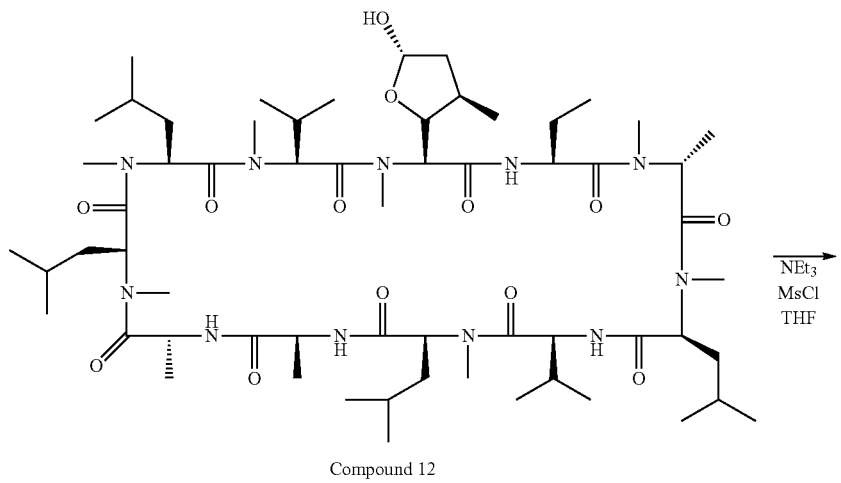
Compound 12
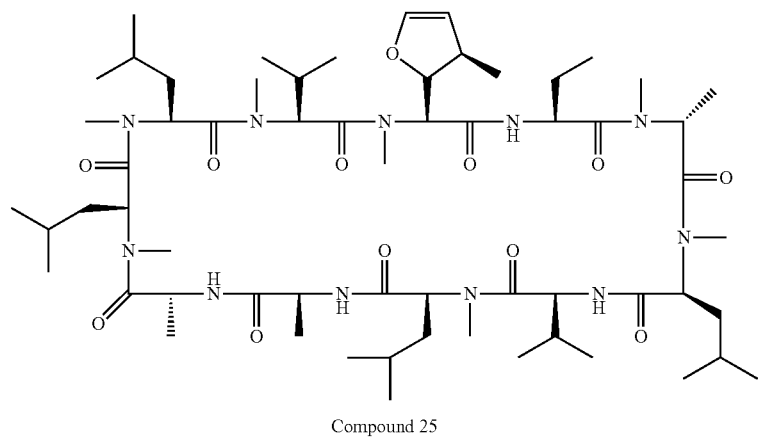
Compound 25

To a solution of [(2S)-2-[(2R,3R)-5-hydroxy-3-methyl-tetrahydrofuran-2-yl]-2-(methylamino)acetic acid]¹ [(R)-methyl-Sar]³ cyclosporin A (Compound 12) (200 mg, 0.166 mmol) in THF (5 ml) was added triethylamine (0.136 ml, 0.976 mmol) followed by methanesulfonyl chloride (0.040 ml, 0.517 mmol) and the reaction mixture was stirred at room temperature over 18 hours. The reaction mixture was evaporated under reduced pressure to a colourless gum. The gum was dissolved in DCM and washed with 1M HCl then sat. aq. sodium bicarbonate, dried (MgSO₄), filtered and evaporated under reduced pressure to yield the crude product as a white solid. The crude product was purified by PTLC eluting with MTBE to give Compound 25 as a white solid.

ES/MS: 1186.81 MH⁺

¹H NMR (CDCl₃, ppm) δ 6.06 (m, 1H, double-bond CH), 7.40 (d, 1H, amide NH), 7.53 (d, 1H, amide NH), 7.99 (d, 1H, amide NH), 8.50 (d, 1H, amide NH)

Example 26

Preparation of Compound 26 ([(2S)-2-[(2R,3R)-3,5-dimethyltetrahydrofuran-2-yl]-2-(methylamino)acetic acid]¹ [(R)-methyl-Sar]³ cyclosporin A) commencing with Intermediate 3.3

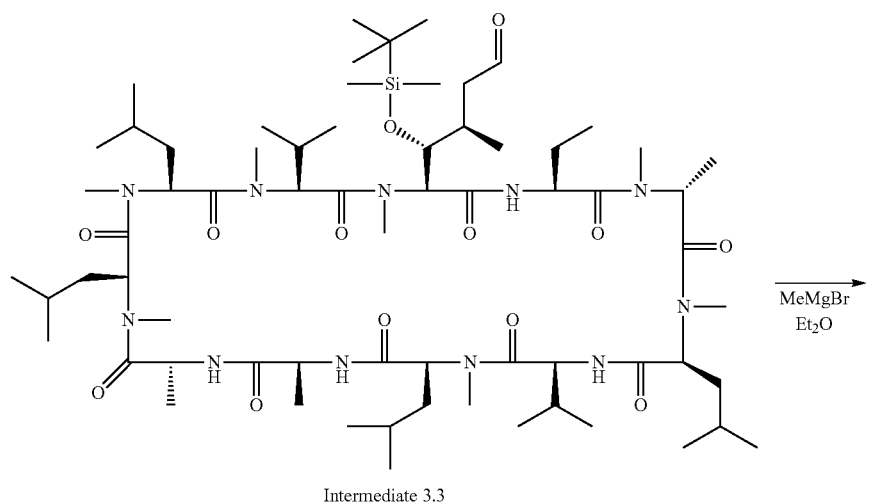

Intermediate 3.3

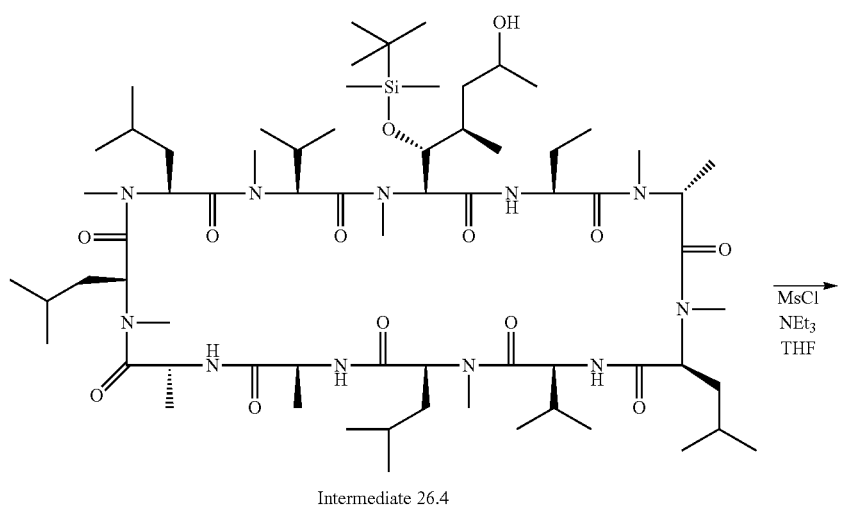

Intermediate 26.4

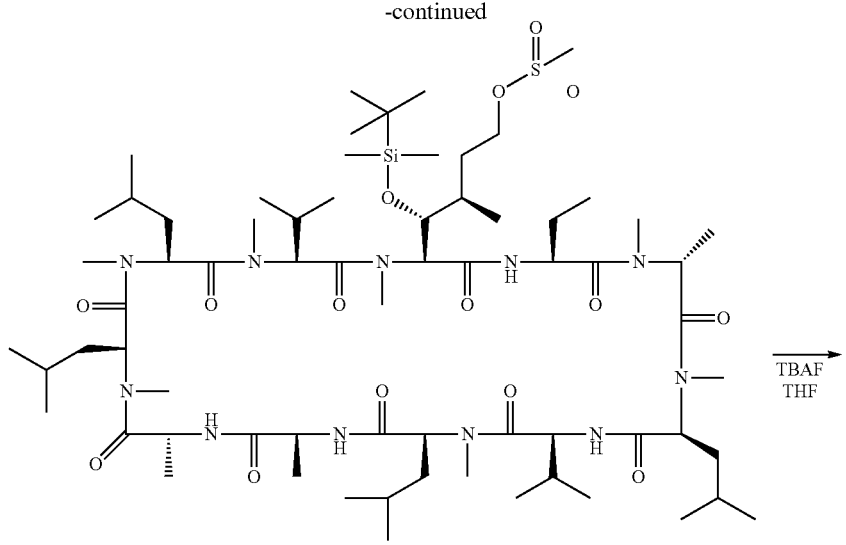

Intermediate 26.5

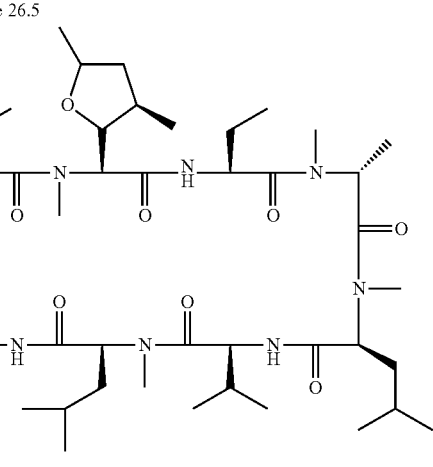

Compound 26

A. Preparation of Intermediate 26.4 from Intermediate 3.3.

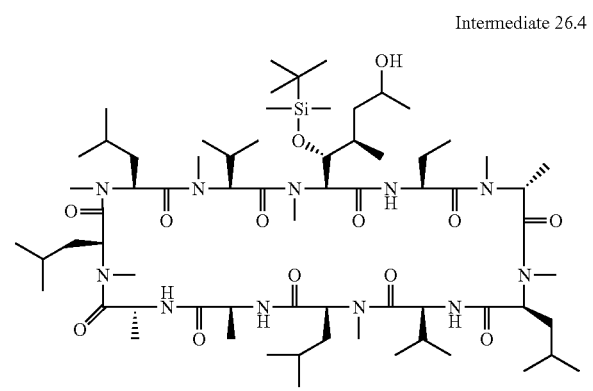 [SMILES: CC[C@H]1NC(=O)[C@@H]([C@H](O[Si](C)(C)C(C)(C)C)[C@H](C)CC(C)O)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Intermediate 26.4

To a solution of [(3R,4R,5 S)-4-(t-butyldimethyl silanyloxy)-3-methyl-5-(methylamino)-1-oxo-hexanoic acid][1] [(R)-methyl-Sar][3] cyclosporin A (Intermediate 3.3) (100 mg, 0.0758 mmol) in diethyl ether (2 ml) under nitrogen atmosphere at −78° C. was added methylmagnesium bromide solution in diethyl ether (3M, 0.507 ml, 1.516 mmol) and the reaction mixture was stirred at −78° C. for over 1 hour, then at room temperature over 70 hours. The reaction mixture was quenched with 1M HCl (5 ml) and extracted into ethyl acetate (2×20 ml). The combined extracts were dried (MgSO$_4$), filtered and evaporated under reduced pressure to yield the crude product as a white solid. Purification by PTLC eluting with 30% acetone/70% hexane gave Intermediate 26.4 as a white solid.

ES/MS: 1334.88 MH$^+$ $^1$H NMR (CDCl$_3$, ppm) Mixture of two isomers in 2:1 ratio.

Major isomer: δ 7.61 (d, 1H, amide NH), 7.76 (d, 1H, amide NH), 7.92 (d, 1H, amide NH), 8.34 (d, 1H, amide NH). Minor isomer: δ 7.51 (d, 1H, amide NH), 7.70 (d, 1H, amide NH), 7.83 (d, 1H, amide NH), 8.27 (d, 1H, amide NH)

B. Preparation of Intermediate 26.5 from Intermediate 26.4.

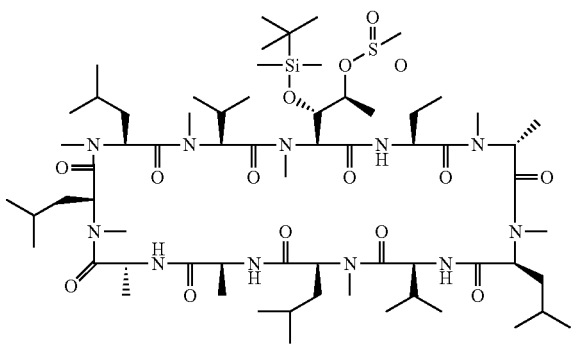

Intermediate 26.5

Intermediate 26.5 was prepared in a similar manner to Intermediate 5 in Scheme 1 by condensing Intermediate 26.4 with methanesulphonyl chloride in DCM in the presence of triethylamine to give Intermediate 26.5.

$^1$H NMR (CDCl$_3$, ppm) Mixture of two isomers. δ 7.58 (m, 1H, amide NH), 7.72 (d, 1H, amide NH), 7.90 (m, 1H, amide NH), 8.32 (m, 1H, amide NH).

C. Preparation of Compound 26 from Intermediate 26.5.

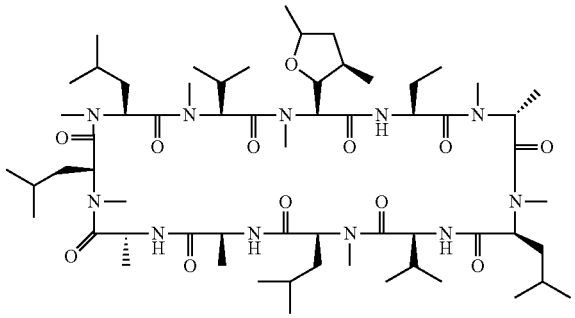

Compound 26

Intermediate 26.5 was cyclized to give Compound 26 by stirring in the presence of TBAF in THF as described for the preparation of Compound 1 in Scheme 1.

ES/MS: 1202.84 MH$^+$ $^1$H NMR (CDCl$_3$, ppm) Mixture of two isomers in approx. 1:1 ratio. δ 7.37-7.60 (m, 2H, amide NH), 8.06 (m, 1H, amide NH), 8.32 (m, 1H, amide NH)

Example 27

Preparation of compounds of Formula I wherein R$^2$ is methyl are prepared from Cyclosporin B by adapting one or more of the schemes and/or procedures disclosed herein.

Example 28

Preparation of compounds of Formula I wherein R$^2$ is n-propyl are prepared from Cyclosporin G by adapting one or more of the schemes and/or procedures disclosed herein.

Example 29

Preparation of compounds of Formula I wherein R$^2$ is isopropyl are prepared from Cyclosporin D by adapting one or more of the schemes and/or procedures disclosed herein.

Example 30

Preparation of compounds of Formula I wherein R$^2$ is —CH$_2$(CH$_3$)OH are prepared from Cyclosporin C by adapting one or more of the schemes and/or procedures disclosed herein.

Example 31

Preparation of compounds of Formula I wherein R$^3$ is —CH$_2$OH or CH$_2$OCH$_3$. Compounds of Formula I wherein R$^3$ is —CH$_2$OH are prepared essentially as described by D. Seebach et al. (1993) *Helvetica Chimica Acta* 73(4): 1564-1590. The resulting compound when subsequently methylated using methods known to those skilled in the art of synthetic organic chemistry provides a compound wherein R$^3$ is —CH$_2$OCH$_3$.

Example 32

Preparation of compounds of Formula I wherein R$^3$ is —OC$_{1-6}$alkyl or —SC$_{1-6}$alkyl are prepared essentially as described in US 2010/0167996.

Example 33

Preparation of compounds of Formula I wherein R$^3$ is

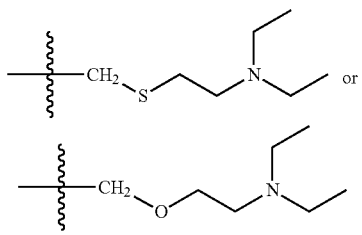

are prepared essentially as described in WO2012/051194 or WO2013/181339.

Example 34

Preparation of compounds of Formula I wherein is R$^4$ ethyl are prepared as described in *J. Med. Chem.* 2014, 57(17) 7145-7159, and *Org. Process Res. Dev.* 2014, 18, 1763-1770.

Example 35

Preparation of compounds of Formula I wherein R$^5$ is isopropyl are prepared as described in *J. Med. Chem.* 2014, 57(17) 7145-7159, and *Org. Process Res. Dev.* 2014, 18, 1763-1770.

Example 36

Preparation of compounds of Formula I wherein R$^5$ is —CH$_2$C(CH$_3$)$_2$(OH), —CH(CH$_3$)(CH$_2$CH$_3$) or —CH$_2$CH(R$^7$)(CH$_2$CH$_3$) are prepared essentially as described in *J. Med. Chem.* 2014, 57, 8503-8516 and WO2014/049540. In one embodiment, there are provided compounds of Formula I wherein:

$R^1$ is

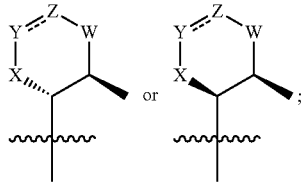

$R^2$ is —$CH_2CH_3$;
$R^3$ is H;
$R^4$ is —$CH_3$;
$R^5$ is —$CH_2C(CH_3)_2(OH)$, —$CH(CH_3)(CH_2CH_3)$ or —$CH_2CH(R^7)(CH_2CH_3)$;
$R^6$ is —$CH_3$;
$R^8$ is —H or —$CH_3$;
$R^9$ is —H, —$CH_3$ or —OH;
$R^{10}$ is —H;
$R^{11}$ is —H;
$R^{12}$ is —H;
$R^{13}$—$CH_3$; and
Z is $(CH_2)_m$, $CR^{12}$ or $NR^{13}$.

Example 37

Preparation of compounds of Formula I wherein $R^6$ is —$CH_2OH$ are prepared by biotransformation, as described in *Journal of Antibiotics*, 1989, 42(4), 591-597.

Example 38

Biological and Physical Properties of Compounds of the Invention

Data showing cyclophilin A (CypA) inhibitory activity, cyclophilin D (CypD) inhibitory activity, immunosuppressive potential, and aqueous solubility for select compounds of Formula I are described in Table 6. General procedures and assays used to obtain the data are given below.

General Procedures and Assays

Protease-Free PPIase Assay

The protease-free PPIase assay measures the rate of cis to trans conversion of a peptide substrate catalyzed by the enzyme cyclophilin A or D. Addition of a cyclophilin inhibitor (e.g., a test compound) slows the catalyzed rate and a $K_i$ value is obtained.

Materials

Assay Buffer:
35 mM HEPES pH 7.8, filtered through a 0.2 μm filter. 50 μM DTT was added prior to use each day and then the buffer was stored on ice.

Enzymes:
Human recombinant cyclophilin A (CypA) (Sigma C3805) enzyme was diluted to 1 μM with enzyme dilution buffer (20 mM HEPES pH 7.8, 40% glycerol, 50 μM DTT and 1 μM BSA) and stored at −20° C. Recombinant 6-His tagged CypA, prepared by the Univ. of Edinburgh, was also used and gave identical results. Human recombinant 6-His tagged cyclophilin D (CypD), prepared by the University of Edinburgh, was used to generate CypD inhibition data.

Substrate:
Succinimide-Ala-Ala-Pro-Phe-p-nitroanilide (SUC-AAPF-pNA) (from Bachem AG, L-1400), 20 mg/ml prepared in 0.5 M LiCl in trifluoroethanol.

Method

All readings were taken with an Agilent 8453 Spectrophotometer which consisted of a cuvette holder, stirrer and chiller to maintain a stirred cuvette temperature of 10.0±0.1° C. The temperature was monitored by the use of temperature probe. To prevent UV degradation of test compounds, the light below 290 nm was blocked using a glass slide in the light path. 1.5 ml of assay buffer was put into a 3 ml quartz cuvette and cooled to 10.0±0.1° C. while stirring (vigorously, but not so fast as to produce cavitation). The inhibitor was diluted in 100% DMSO, and then added to the assay to a maximum final concentration of 0.5% DMSO in the assay. A blank spectrum was obtained, then 3 μL of enzyme was added (2 nM final concentration) and then 3 μL substrate (60 μM final concentration) added. The absorbance was measured at 330 nm for 300 s or 500 s for blank runs (NOTE: the substrate was added in one quick injection and the measurements started immediately to minimize mixing errors).

A first order rate equation was fitted to the absorbance data, for each concentration of inhibitor, to obtain the rate constant (the first 10 to 15 seconds were excluded, as mixing causes errors in this portion of the curve). The catalytic rate was calculated from the enzymatic rate constant minus the background rate constant. An exponential curve was generated using the catalytic rate constants versus the inhibitor concentration to obtain the $K_i$ value for the inhibitor. The $K_i$ value is indicative of the binding affinity between the test compound and cyclophilin A.

Calcineurin Phosphatase (CaN) Assay

The calcineurin phosphatase assay is a means for estimating the immunosuppressive potential of a test compound. Calcineurin is a serine-threonine protein phosphatase that on activation dephosphorylates members of the nuclear factor of activated T cells (NFAT), which are important in T lymphocyte activation. Cyclosporin A (CsA) bound to CypA inhibits calcineurin activity, thus resulting in immunosuppressive effects. Although CsA only inhibits calcineurin when bound to CypA, it is conceivable that some Cyclosporin A (CsA) analogs may also bind calcineurin in the absence of Cyp A. Alternatively, some CsA analogs may bind cyclophilin A without inhibiting calcineurin activity.

To investigate the immunosuppressive potential of exemplary compounds of Formula I, which are cyclosporin analogs, their ability to inhibit calcineurin activity was measured in the presence and absence of CypA.

The CaN assay kit used is based on a colorimetric assay for measuring calcineurin phosphatase activity, and it is commercially available (Enzo Life Sciences and Calbiochem). Calmodulin is also required for calcineurin activity, and RII phosphopeptide is used as an efficient peptide substrate for calcineurin. We have modified the method to enable measurement of CypA-dependent and CypA-independent inhibition of calcineurin through the addition of CypA in a 1:1 complex with the inhibitor. The detection of free phosphate released is based on the classic Malachite green assay.

Materials:
Enzo Life Sciences CaN Assay Kit: BML-AK804
2× Assay Buffer:
100 mM Tris, pH7.5, 200 mM NaCl, 12 mM $MgCl_2$, 1 mM DTT, 0.05% NP-40, 1 mM $CaCl_2$; Malachite Green: BIOMOL Green™ reagent; Calmodulin (Human, recombinant): was thawed on ice, diluted 1:50 with 2× assay buffer, and then stored on ice; Calcineurin: was thawed quickly, stored on ice immediately, diluted 1:12.5 with 1× assay buffer, and then stored on ice; R-II Substrate: 915 μL ultrapure water (UPW) was added to the 1.5 mg vial substrate to give a final concentration of 0.75 mM; Inhibitors: 2.5 mM inhibitor in 100% DMSO; CypA: recombinant human CypA (Sigma C3805), 1 mg/ml; Recombinant 6-His tagged CypA prepared by the University of Edinburgh was also used. Comparison of the results showed that both enzymes gave identical results.

Method

Inhibitor Dilutions:

test compounds (including CsA as control) were diluted in UPW in polypropylene low-binding 96 well plates at 5× the final assay concentration. For samples 'without CypA', a 4-point dilution series of the inhibitor was prepared in duplicate to obtain a final assay concentration of 10, 1, 0.1 and 0.01 μM. For samples 'with CypA', a 7-point dilution series was prepared to obtain a 1:1 complex of the inhibitor with CypA; the inhibitor and CypA final assay concentrations of 10, 3.33, 1.11, 0.37, 0.12, 0.04, 0.014 μM were prepared. CsA inhibitor controls were also prepared to obtain a final concentration of 10 μM CsA with and without 10 μM CypA.

Assay Setup:

using the half area 96 well plates supplied with the kit, 10 μl UPW was added to duplicate wells to provide the non-inhibited control. 10 μl of the inhibitor or the inhibitor/CypA complex was added to the appropriate sample wells. 25 μl of the 2× assay buffer with calmodulin (CaM) was added to all wells, then 5 μl of calcineurin phosphatase (CaN) was added to all wells (40 U per well final concentration) except duplicate 'no calcineurin blank' wells to which 5 μL 1× assay buffer was added. The assay plate was placed in an oven at 30° C. for 15 minutes to equilibrate to the reaction temperature. The reaction was started by the addition of 10 μl RII-peptide (0.15 mM final concentration). The reaction was allowed to proceed at 30° C. for a time period in which the reaction is linear for about 60 minutes. The reaction was then terminated by adding 100 μl of the Malachite Green reagent. The color was allowed to develop for 15-30 minutes at room temperature before the absorbance at 620 nm was measured using a plate reader (Molecular Devices—SpectraMax M5). The data were analyzed by subtracting 'no calcineurin blank' from all the absorbance readings and plotting the background corrected absorbances against $Log_{10}$ inhibitor concentration. A sigmoidal-dose response curve was fitted to the data using GraphPad Prism Software.

CsA is a potent inhibitor of calcineurin activity and therefore a potent immunosuppressive. It exerts its immunosuppressive activity by binding to CypA to form a complex, which then binds to calcineurin and thereby inhibits calcineurin activity. As shown in Table 6, CsA has a $IC_{50}$ value of 210 nM in the calcineurin/CypA assay. Thus, compounds with $IC_{50}$ values higher than 210 nM in this assay will be predictably less immunosuppressive than cyclosporin A. As can be seen from Table 6, compounds of Formula I exhibit much higher $IC_{50}$ values than 210 nM in the calcineurin/CypA assay and would therefore be expected to be much less immunosuppressive than CsA.

Mixed Lymphocyte Reaction ("MLR") Assay

The MLR assay is widely used in the field of immunology to measure T cell proliferation, and therefore is another means of estimating the immunosuppressive potential of test compounds. In the MLR assay, splenocytes isolated from two different strains of mice, termed Stimulator (e.g. BALB/c mice) and Responder (e.g. C57BL/6 mice), are mixed in cell culture, in turn eliciting an alloimmune response (immunity against antigens between individuals of the same species). Alloimmunity results in robust proliferation of T cells contained within the splenocyte cell population from both strains of mice. To ensure that T cell proliferation is restricted to only the Responder population (C57BL/6), the Stimulator cells (BALB/c) are first inactivated via X-irradiation before co-culture with Responder cells in the absence or presence of different concentrations of test compound. If the test compound present in the culture medium is immunosuppressive, the proliferation of the responder cells is reduced. Total proliferation is quantified by the cellular uptake of $[^3H]$-thymidine, which occurs during cell division. Therefore, compounds that are less immunosuppressive than CsA will require a higher concentration to reduce T cell proliferation; and compounds that are not immunosuppressive will not affect T cell proliferation even at the highest concentrations tested.

Female C57BL/6 and BALB/c mice, 6-8 weeks of age, were obtained from the Frederick Cancer Research and Development Center of the National Cancer Institute (Frederick, Md.). Spleens were harvested aseptically from all mice and single cell suspensions were prepared by disaggregating the cells with frosted glass slides, allowing the debris to settle, and washing the cells twice with complete medium. Complete medium consists of RPMI 1640 medium containing 25 mM HEPES buffer (HyClone, Logan, Utah) supplemented with 10% heat-inactivated fetal bovine serum (FBS; Atlanta Biologicals, Lawrenceville, Ga.), 100 μg/mL streptomycin, 100 U/mL penicillin G, 0.25 μg/mL amphotericin B (HyClone), 2 mM L-glutamine dipeptide (HyClone), and $2×10^{-5}$ M 2-mercaptoethanol (Sigma). Cells were washed twice and resuspended in complete medium. Cell counts were performed using a Beckman Coulter Z-1 particle counter (Fullerton, Calif.). Cell viability was determined by propidium iodide (PI) staining using an Accuri C6 flow cytometer (Ann Arbor, Mich.).

Spleen cells from C57BL/6 ($H-2^b$) and BALB/c ($H-2^d$) were used as responder (R) and stimulator (S) cells, respectively. Cells were plated in triplicate in 96-well flat microtiter plates (Costar, Cambridge, Mass.) such that each well contained $2×10^5$ R and $8×10^5$ S cells. Cultures were incubated in the absence or presence of various concentrations of CsA, test compounds (e.g., a compound of Formula I), or medium at 37° C. in humidified 5% $CO_2$ for five days, pulsed with $^3$H-thymidine ($^3$H-TdR) for the final 16 hours of incubation, and harvested using a Brandel 96-well cell harvester (Gaithersburg, Md.). Proliferation was measured by counting the radioactivity on filter mats in a Wallac 1450 Microbeta TriLux scintillation counter (Turku, Finland). Controls to demonstrate effective inactivation by the X-irradiation were performed by incubating the S cells with 5 μg/mL of PHA at $2×10^5$ cells/well. These control cultures were incubated for 3 days under the same conditions as those described for the MLR; lymphoproliferation was determined in the same manner as described above.

Water Solubility Assay (Measured in pH 7.8 Buffer)

The aqueous solubility of a compound of Formula I in buffer (pH 7.8) was measured by recording the onset of precipitation of the compound as a function of increasing concentration. The onset of precipitation, if it occurred, was detected by an increase in absorbance at 650 nm.

Materials
Assay Buffer:
35 mM HEPES pH 7.8.
Stock solutions of Control and Test Compounds: 10 mM in 100% DMSO.
Method 10 mM stock solutions of control and test compounds were prepared in 100% DMSO. A series of dilutions were prepared from the stock in DMSO so that the final concentrations in the assay were 0, 3.33, 10, 25, 50, 75 and 100 µM, and DMSO was limited to 1%.

Assay buffer (247.5 µl) was placed into a flat bottomed transparent 96-well plate. For blank samples, DMSO (2.5 µl) was added. For test and control samples, 2.5 µl of the appropriate DMSO dilution stocks were added to the appropriate well. All test and control compounds were performed in triplicate.

The plates were sealed with adhesive plate seal and shaken at 250 rpm at 25° C. for 18 h on a plate shaker. After incubation, the plate seals were taken off and any bubbles observed in wells removed. The plates were read on a SpectraMaxM5 with a 5 s pre-shake at 650 nm.

Data files were transferred to the appropriate worksheet and the solubility range of the compounds was calculated from the data.

The values shown in Table 6 indicate the concentration in µM (micromolar) at which the compound remains in solution.

TABLE 6

Cyp A inhibitory activity, Cyp D inhibitory activity, immunosuppressive potential, and aqueous solubility for CsA and select compounds of Formula I.

| Compound | CypA Protease-free PPIase Assay* $K_i$ (nM) | CypD Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Aqueous Solubility pH7.4 (µM) |
|---|---|---|---|---|---|
| CsA | 1.5 | 15 | 210 | 1 | 25 |
| 1 | 81 | 9.7 | >10,000 | 377 | 75 |
| 2 | 237 | 39 | >10,000 | | 50 |
| 3 | 95 | 4.4 | >10,000 | 300 | >100 |
| 4 | 509 | 920 | >10,000 | | — |
| 5 | 198 | 14.5 | >10,000 | | 50 |
| 6 | 5.6 | 1.9 | >10,000 | | 50 |
| 7 | 400 | 81 | >10,000 | | 75 |
| 8 | 1,500 | 105 | >10,000 | | >100 |
| 9 | 8,600 | 200 | >10,000 | | >100 |
| 10 | 2,000 | 680 | >10,000 | | >100 |
| 11 | 270 | 18 | >10,000 | | — |
| 12 | 49 | 12 | >10,000 | | — |
| 13 | 414 | 840 | >10,000 | | — |
| 14 | 20.4 | 8.4 | >10,000 | | >100 |
| 15 | 38 | 46 | 5,286 | | — |
| 16 | 386 | 560 | 6,670 | | — |
| 17 | 105 | 85 | 7,736 | | — |
| 18 | 79 | 15 | >10,000 | | 25 |
| 19 | 404 | 130 | 8,986 | | >100 |
| 20 | 149 | 36 | >10,000 | | >100 |
| 21 | 304 | 42 | 8,158 | | >100 |
| 22 | 315 | 160 | >10,000 | | >100 |
| 23 | 754 | 280 | >10,000 | | — |
| 24 | 550 | 79 | >10,000 | | >100 |
| 25 | 67 | 9.4 | >10,000 | | 50 |
| 26 | 275 | 64 | >10,000 | | 75 |

*Data generated using the protease-free PPIase assay.

** Data generated using the Calcineurin Phosphatase (CaN) Assay. No significant inhibition of CaN was observed in the absence or presence of CypA. Data obtained in the presence of Cyp A (+CypA) are reported in the table.

*** Data generated using the Mixed Lymphocyte Reaction ("MLR") Assay. The values shown are expressed as the $IC_{50}$ for the compound relative to the $IC_{50}$ for CsA. Thus, a value of 10, for example, indicates that the compound is about ten times less immunosuppressive than CsA.

In general, compounds having Formula I are potent inhibitors of cyclophilins, particularly CyD; and have low immunosuppressive activity as measured by the calcineurin phosphatase assay ($IC_{50}$>5 µM) and mixed lymphocyte reaction (MLR) assay (>50-fold less active than CsA).

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, those skilled in the art could make numerous and various modifications or changes to or alternative configurations of the disclosed subject matter can be made in accordance with the teachings herein without departing from the spirit of the present specification. Changes in detail may be made without departing from the spirit of the invention as defined in the appended claims. Lastly, the terminology used herein is for the purpose of describing particular embodiments only, and is not intended to limit the scope of the present invention, which is defined solely by the claims. In addition, it is intended that all matter contained in the above description or shown in the accompanying drawings shall be interpreted as illustrative only and not limiting. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term.

Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

What is claimed is:

1. A compound of Formula I:

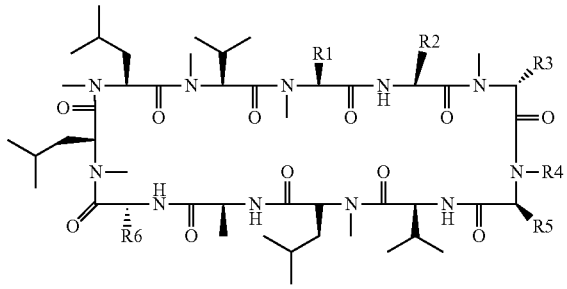

Formula I wherein:

$R^1$ is

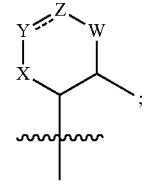

;

$R^2$ is —CH$_3$, —CH$_2$CH$_3$, —CH(CH$_3$)(OH), —CH(CH$_3$)$_2$ or —CH$_2$CH$_2$CH$_3$;

$R^3$ is —H, —C$_{1-6}$alkyl, —OC$_{1-6}$alkyl, —C$_{1-6}$haloalkyl, —SC$_{1-6}$ alkyl, —CH$_2$OH, —CH$_2$OCH$_3$,

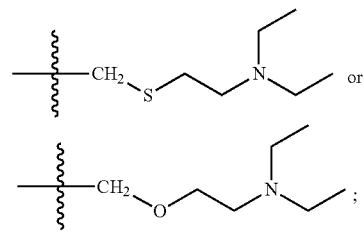

or

;

$R^4$ is —CH$_3$, —CH$_2$CH$_3$ or —CH$_2$CH$_2$CH$_3$;

$R^5$ is —CH(CH$_3$)$_2$, —CH$_2$CH(CH$_3$)$_2$, —CH$_2$C(CH$_3$)$_2$(OH), —CH(CH$_3$)(CH$_2$CH$_3$) or —CH$_2$CH(R$^7$)(CH$_2$CH$_3$);

$R^6$ is —CH$_3$ or —CH$_2$OH;

$R^7$ is —OC$_{1-6}$alkyl;

$R^9$ is —H;

$R^{10}$ is —H;

X is O;

Y is CR$^9$R$^{10}$;

Z is (CH$_2$)$_m$;

W is (CH$_2$)$_n$;

m is 1;

n is 0; and the dashed line indicates that the bond joining Y and Z is a single bond;

or a pharmaceutically acceptable salt thereof.

2. The compound of claim 1, wherein $R^1$ is:

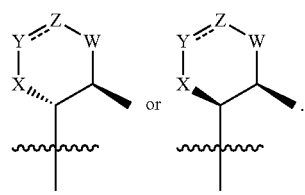

3. The compound of claim 1, wherein $R^2$ is —CH$_3$, —CH$_2$CH$_3$, —CH(CH$_3$)(OH) or —CH(CH$_3$)$_2$.

4. The compound of claim 1, wherein $R^3$ is H, —C$_{1-3}$alkyl or —C$_{1-3}$haloalkyl.

5. The compound of claim 1, wherein $R^4$ is —CH$_3$; $R^5$ is —CH$_2$CH(CH$_3$)$_2$; and $R^6$ is —CH$_3$.

6. The compound of claim 1, wherein:
$R^1$ is

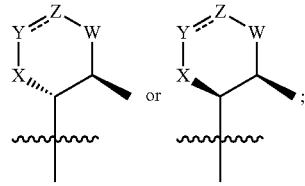

$R^2$ is —CH$_3$, —CH$_2$CH$_3$, —CH(CH$_3$)(OH) or —CH(CH$_3$)$_2$;
$R^3$ is H, —C$_{1-3}$alkyl or —C$_{1-3}$haloalkyl;
$R^4$ is —CH$_3$;
$R^5$ is —CH$_2$CH(CH$_3$)$_2$; and
$R^6$ is —CH$_3$.

7. A compound of claim 1 selected from the group consisting of:

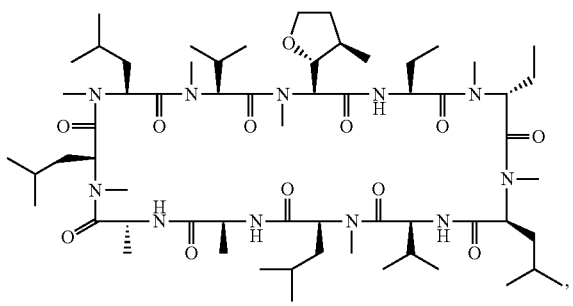

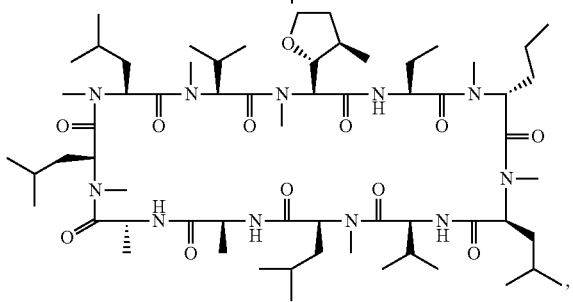

-continued

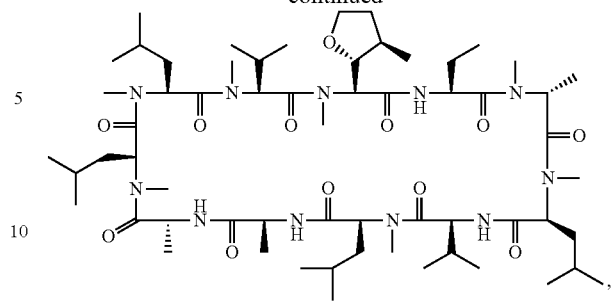

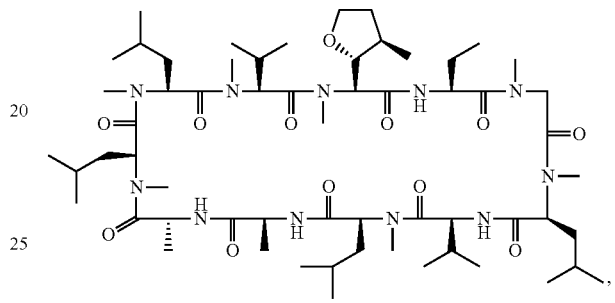

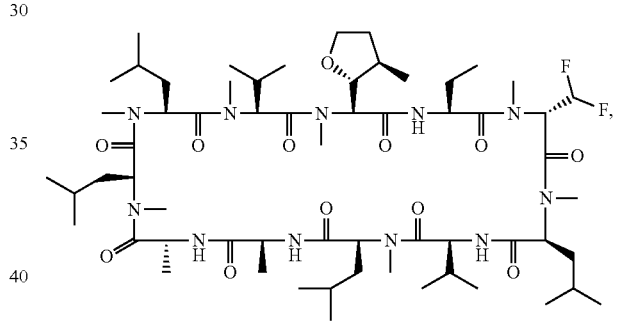

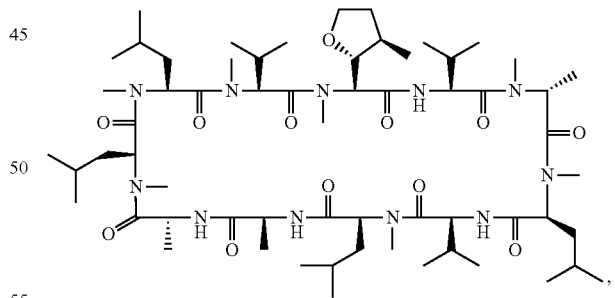

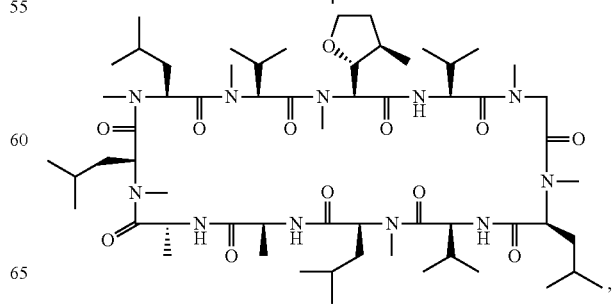

-continued
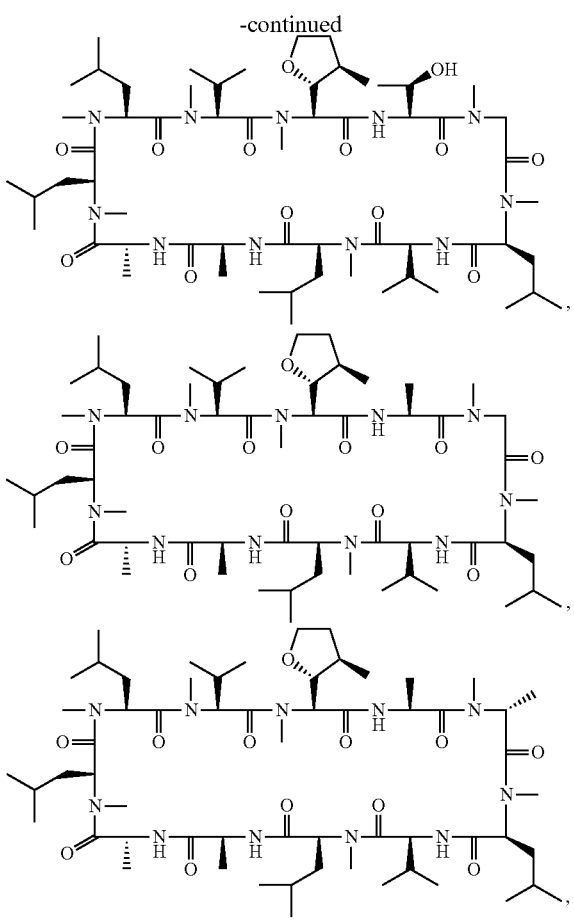
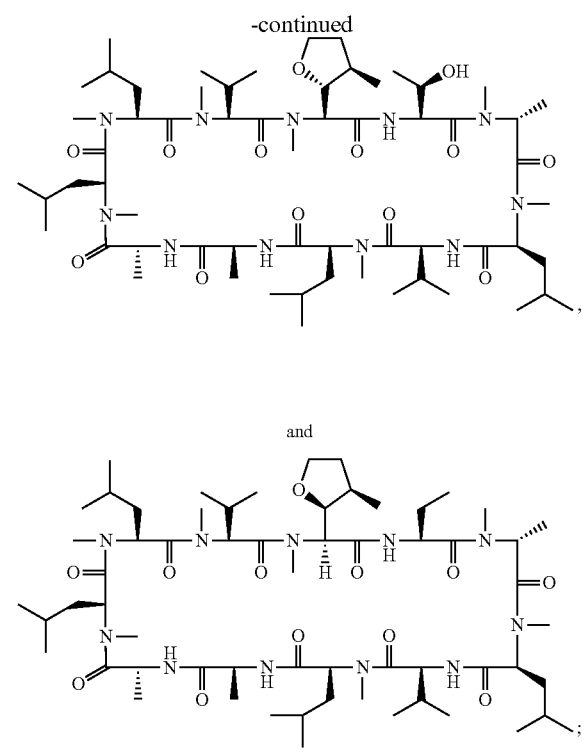
and pharmaceutically acceptable salts thereof.
8. A pharmaceutical composition comprising a therapeutically effective amount of a compound of claim 1 or 7, and a pharmaceutically acceptable carrier.
* * * * *